US010568616B2

(12) United States Patent
Monllor et al.

(10) Patent No.: US 10,568,616 B2
(45) Date of Patent: Feb. 25, 2020

(54) INSTRUMENTS AND METHODS OF SOFT TISSUE FIXATION

(71) Applicant: Howmedica Osteonics Corp., Mahwah, NJ (US)

(72) Inventors: Carlos Benitez Monllor, Ponce, PR (US); Logan Renwick, Denver, CO (US); Michael Taylor White, Denver, CO (US); Kyle Craig Pilgeram, San Jose, CA (US); Ross Callison, Denver, CO (US); Benjamin Yore, Castle Rock, CO (US); José Raúl Marchand, San Juan, PR (US); Jaime Genuario, Lone Tree, CO (US); Keith Taylor, Parker, CO (US)

(73) Assignee: Howmedica Osteonics Corp., Mahwah, NJ (US)

( * ) Notice: Subject to any disclaimer, the term of this patent is extended or adjusted under 35 U.S.C. 154(b) by 504 days.

(21) Appl. No.: 15/185,985

(22) Filed: Jun. 17, 2016

(65) Prior Publication Data
US 2016/0296223 A1 Oct. 13, 2016

Related U.S. Application Data

(63) Continuation-in-part of application No. 14/573,538, filed on Dec. 17, 2014, now abandoned.

(51) Int. Cl.
*A61B 17/04* (2006.01)

(52) U.S. Cl.
CPC .. *A61B 17/0401* (2013.01); *A61B 2017/0409* (2013.01); *A61B 2017/0464* (2013.01)

(58) Field of Classification Search
CPC ............ A61B 17/0401; A61B 17/0057; A61B 17/0467; A61B 17/0469; A61B 17/0482;
(Continued)

(56) References Cited

U.S. PATENT DOCUMENTS

| 749,624 A | 1/1904 | Mc Cullough |
| 1,308,798 A | 7/1919 | Masland |

(Continued)

FOREIGN PATENT DOCUMENTS

| DE | 3131496 A1 | 2/1983 |
| DE | 4231101 A1 | 3/1994 |

(Continued)

OTHER PUBLICATIONS

BIOMET Sports Medicine: Micromax Flex Suture Anchor, (2008).
(Continued)

*Primary Examiner* — Vi X Nguyen
(74) *Attorney, Agent, or Firm* — Lerner, David, Littenberg, Krumholz & Mentlik, LLP

(57) ABSTRACT

An inserter assembly for inserting anchors into bone includes a handle having a handle body. A first inserter is disposed within the handle body and is fixedly connected thereto. The first inserter has an insertion end configured to retain a first anchor for insertion thereof into bone. A second inserter is slidably disposed within the handle body and has an insertion end configured to retain a second anchor for insertion thereof into bone. A sleeve is slidably disposed within the handle body and is releasably connected to the second inserter.

20 Claims, 31 Drawing Sheets

(58) Field of Classification Search
CPC ........ A61B 17/0483; A61B 2017/0464; A61B
2017/0446; A61B 2017/0409; A61B
17/04; A61B 17/487; A61B 17/3468;
A61B 2017/0414
See application file for complete search history.

(56) References Cited

U.S. PATENT DOCUMENTS

| | | |
|---|---|---|
| 1,624,530 A | 4/1927 | Caruso |
| 2,073,903 A | 3/1937 | O'Neil |
| 2,267,925 A | 12/1941 | Johnston |
| 2,382,019 A | 8/1945 | Miller |
| 2,494,229 A | 1/1950 | Collison |
| 2,515,365 A | 7/1950 | Zublin |
| 2,547,571 A | 4/1951 | Ettinger |
| 2,808,632 A | 10/1957 | Cline |
| 2,833,284 A | 5/1958 | Springer |
| 3,384,085 A | 5/1968 | Hall |
| 3,461,875 A | 8/1969 | Hall |
| 3,554,192 A | 1/1971 | Isbemer |
| 3,580,256 A | 5/1971 | Wilkinson et al. |
| 3,608,095 A | 9/1971 | Barry |
| 3,659,597 A | 5/1972 | Wolfers |
| 3,750,671 A | 8/1973 | Hedrick |
| 3,810,456 A | 5/1974 | Karman |
| 3,845,772 A | 11/1974 | Smith |
| 3,867,932 A | 2/1975 | Huene |
| 3,892,232 A | 7/1975 | Neufeld |
| 3,976,079 A | 8/1976 | Samuels et al. |
| 4,265,231 A | 5/1981 | Scheller, Jr. et al. |
| 4,328,839 A | 5/1982 | Lyons et al. |
| 4,483,562 A | 11/1984 | Schoolman |
| 4,489,446 A | 12/1984 | Reed |
| 4,541,423 A | 9/1985 | Barber |
| 4,608,972 A | 9/1986 | Small |
| 4,611,515 A | 9/1986 | Marbourg, Jr. |
| 4,646,738 A | 3/1987 | Trott |
| 4,706,659 A | 11/1987 | Matthews et al. |
| 4,741,330 A | 5/1988 | Hayhurst |
| 4,748,872 A | 6/1988 | Brown |
| 4,751,922 A | 6/1988 | DiPietropolo |
| 4,781,182 A | 11/1988 | Purnell et al. |
| 4,823,780 A | 4/1989 | Odensten et al. |
| 4,863,471 A | 9/1989 | Mansat |
| 4,872,451 A | 10/1989 | Moore et al. |
| 4,946,462 A | 8/1990 | Watanabe |
| 5,002,546 A | 3/1991 | Romano |
| 5,021,059 A | 6/1991 | Kensey et al. |
| 5,030,219 A | 7/1991 | Matsen, III et al. |
| 5,037,422 A | 8/1991 | Hayhurst et al. |
| 5,037,423 A | 8/1991 | Kenna |
| 5,061,277 A | 10/1991 | Carpentier et al. |
| 5,064,431 A | 11/1991 | Gilbertson et al. |
| 5,122,134 A | 6/1992 | Borzone et al. |
| 5,123,914 A | 6/1992 | Cope |
| 5,133,720 A | 7/1992 | Greenberg |
| 5,139,520 A | 8/1992 | Rosenberg |
| 5,141,520 A | 8/1992 | Goble et al. |
| 5,163,940 A | 11/1992 | Bourque |
| 5,190,548 A | 3/1993 | Davis |
| 5,203,595 A | 4/1993 | Borzone et al. |
| 5,203,787 A | 4/1993 | Noblitt et al. |
| RE34,293 E | 6/1993 | Goble et al. |
| 5,234,435 A | 8/1993 | Seagrave, Jr. |
| 5,259,846 A | 11/1993 | Granger et al. |
| 5,269,785 A | 12/1993 | Bonutti |
| 5,269,809 A | 12/1993 | Hayhurst et al. |
| 5,300,077 A | 4/1994 | Howell |
| 5,314,429 A | 5/1994 | Goble |
| 5,320,115 A | 6/1994 | Kenna |
| 5,320,626 A | 6/1994 | Schmieding |
| 5,324,308 A | 6/1994 | Pierce |
| 5,350,383 A | 9/1994 | Schmieding et al. |
| RE34,762 E | 10/1994 | Goble et al. |
| 5,374,269 A | 12/1994 | Rosenberg |
| 5,385,567 A | 1/1995 | Goble |
| 5,391,170 A | 2/1995 | McGuire et al. |
| 5,391,171 A | 2/1995 | Schmieding |
| RE34,871 E | 3/1995 | McGuire et al. |
| 5,395,188 A | 3/1995 | Bailey et al. |
| 5,403,317 A | 4/1995 | Bonutti |
| 5,403,348 A | 4/1995 | Bonutti |
| 5,405,359 A | 4/1995 | Pierce |
| 5,409,494 A | 4/1995 | Morgan |
| 5,417,691 A | 5/1995 | Ayhurst |
| 5,423,860 A | 6/1995 | Lizardi et al. |
| 5,437,677 A | 8/1995 | Shearer et al. |
| 5,441,502 A | 8/1995 | Bartlett |
| 5,443,482 A | 8/1995 | Stone et al. |
| 5,458,604 A | 10/1995 | Schmieding |
| 5,464,407 A | 11/1995 | McGuire |
| 5,464,425 A | 11/1995 | Skiba |
| 5,464,426 A | 11/1995 | Bonutti |
| 5,466,243 A | 11/1995 | Schmieding et al. |
| 5,472,452 A | 12/1995 | Trott |
| 5,486,197 A | 1/1996 | Le et al. |
| 5,488,761 A | 2/1996 | Leone |
| 5,496,348 A | 3/1996 | Bonutti |
| 5,505,736 A | 4/1996 | Reimels et al. |
| 5,520,693 A | 5/1996 | McGuire et al. |
| 5,520,700 A | 5/1996 | Beyar et al. |
| 5,522,846 A | 6/1996 | Bonutti |
| 5,527,316 A | 6/1996 | Stone et al. |
| 5,527,343 A | 6/1996 | Bonutti |
| 5,529,580 A | 6/1996 | Kusunoki et al. |
| 5,531,759 A | 7/1996 | Kensey et al. |
| 5,534,012 A | 7/1996 | Bonutti |
| 5,540,703 A | 7/1996 | Barker, Jr. et al. |
| 5,545,178 A | 8/1996 | Kensey et al. |
| 5,548,862 A | 8/1996 | Curtis |
| 5,569,269 A | 10/1996 | Hart et al. |
| 5,569,306 A | 10/1996 | Thal |
| 5,570,706 A | 11/1996 | Howell |
| 5,571,111 A | 11/1996 | Aboczky |
| 5,573,542 A | 11/1996 | Stevens |
| 5,575,819 A | 11/1996 | Amis |
| 5,584,695 A | 12/1996 | Lal Sachdeva et al. |
| 5,584,835 A | 12/1996 | Greenfield |
| 5,601,557 A | 2/1997 | Hayhurst |
| 5,601,561 A | 2/1997 | Terry et al. |
| 5,618,314 A | 4/1997 | Harwin et al. |
| 5,645,545 A | 7/1997 | Bryant |
| 5,645,589 A | 7/1997 | Li |
| 5,647,874 A | 7/1997 | Hayhurst |
| 5,649,963 A | 7/1997 | McDevitt |
| 5,658,313 A | 8/1997 | Thal |
| 5,662,658 A | 9/1997 | Wenstrom, Jr. |
| 5,665,110 A | 9/1997 | Chervitz et al. |
| 5,665,111 A | 9/1997 | Ray et al. |
| 5,665,112 A | 9/1997 | Thal |
| 5,667,509 A | 9/1997 | Westin |
| 5,674,279 A | 10/1997 | Wright et al. |
| 5,681,320 A | 10/1997 | McGuire |
| 5,681,352 A | 10/1997 | Clancy, III et al. |
| 5,683,401 A | 11/1997 | Schmieding et al. |
| 5,683,418 A | 11/1997 | Luscombe et al. |
| 5,683,419 A | 11/1997 | Thal |
| 5,690,676 A | 11/1997 | DiPoto et al. |
| 5,690,677 A | 11/1997 | Schmieding et al. |
| 5,695,513 A | 12/1997 | Johnson et al. |
| 5,699,657 A | 12/1997 | Paulson |
| 5,709,708 A | 1/1998 | Thal |
| 5,713,905 A | 2/1998 | Goble et al. |
| 5,716,397 A | 2/1998 | Myers |
| 5,718,717 A | 2/1998 | Bonutti |
| 5,720,765 A | 2/1998 | Thal |
| 5,725,541 A | 3/1998 | Anspach, III et al. |
| 5,728,136 A | 3/1998 | Thal |
| 5,732,606 A | 3/1998 | Chiang |
| 5,733,306 A | 3/1998 | Bonutti |
| 5,733,307 A | 3/1998 | Dinsdale |
| 5,749,899 A | 5/1998 | Bardin et al. |
| 5,755,724 A | 5/1998 | Yoon |
| 5,755,731 A | 5/1998 | Grinberg |

(56) References Cited

U.S. PATENT DOCUMENTS

| | | |
|---|---|---|
| 5,766,221 A | 6/1998 | Benderev et al. |
| 5,782,862 A | 7/1998 | Bonutti |
| 5,782,864 A | 7/1998 | Lizardi |
| 5,782,866 A | 7/1998 | Wenstrom, Jr. |
| 5,797,918 A | 8/1998 | McGuire et al. |
| 5,810,825 A | 9/1998 | Huebner |
| 5,814,056 A | 9/1998 | Prosst et al. |
| 5,836,953 A | 11/1998 | Yoon |
| 5,851,208 A | 12/1998 | Trott |
| 5,885,294 A | 3/1999 | Pedlick et al. |
| 5,888,034 A | 3/1999 | Greenberg |
| 5,891,168 A | 4/1999 | Thal |
| 5,897,574 A | 4/1999 | Bonutti |
| 5,906,626 A | 5/1999 | Carrillo |
| 5,921,986 A | 7/1999 | Bonutti |
| 5,928,244 A | 7/1999 | Tovey et al. |
| 5,941,139 A | 8/1999 | Vodehnal |
| 5,948,002 A | 9/1999 | Bonutti |
| 5,951,559 A | 9/1999 | Burkhart |
| 5,968,078 A | 10/1999 | Grotz |
| 5,970,697 A | 10/1999 | Jacobs et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,993,451 A | 11/1999 | Burkhart |
| 5,997,541 A | 12/1999 | Schenk |
| 6,007,566 A | 12/1999 | Wenstrom, Jr. |
| 6,007,567 A | 12/1999 | Bonutti |
| 6,010,515 A | 1/2000 | Swain et al. |
| 6,010,525 A | 1/2000 | Bonutti et al. |
| 6,019,767 A | 2/2000 | Howell |
| 6,024,758 A | 2/2000 | Thal |
| 6,045,574 A | 4/2000 | Thal |
| 6,053,922 A | 4/2000 | Krause et al. |
| 6,068,642 A | 5/2000 | Johnson et al. |
| 6,077,292 A | 6/2000 | Bonutti |
| 6,083,522 A | 7/2000 | Chu et al. |
| 6,120,511 A | 9/2000 | Chan |
| 6,143,017 A | 11/2000 | Thal |
| 6,146,385 A | 11/2000 | Torrie et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,183,461 B1 | 2/2001 | Matsuura et al. |
| 6,187,011 B1 | 2/2001 | Torrie |
| 6,189,422 B1 | 2/2001 | Stihl |
| 6,210,415 B1 | 4/2001 | Bester |
| 6,224,608 B1 | 5/2001 | Ciccolella et al. |
| 6,245,081 B1 | 6/2001 | Bowman et al. |
| 6,254,604 B1 | 7/2001 | Howell |
| 6,306,138 B1 | 10/2001 | Clark et al. |
| 6,343,482 B1 | 2/2002 | Endo et al. |
| 6,352,538 B2 | 3/2002 | McGuire et al. |
| 6,358,253 B1 | 3/2002 | Torrie et al. |
| 6,419,678 B1 | 7/2002 | Asfora |
| 6,419,684 B1 | 7/2002 | Heisler et al. |
| 6,423,073 B2 | 7/2002 | Bowman |
| 6,436,100 B1 | 8/2002 | Berger |
| 6,436,124 B1 | 8/2002 | Anderson et al. |
| 6,440,138 B1 | 8/2002 | Reiley et al. |
| 6,440,141 B1 | 8/2002 | Philippon |
| 6,447,518 B1 | 9/2002 | Krause et al. |
| 6,464,713 B2 | 10/2002 | Bonutti |
| 6,475,230 B1 | 11/2002 | Bonutti et al. |
| 6,478,800 B1 | 11/2002 | Fraser et al. |
| 6,485,504 B1 | 11/2002 | Johnson et al. |
| 6,500,195 B2 | 12/2002 | Bonutti |
| RE37,963 E | 1/2003 | Thal |
| 6,508,830 B2 | 1/2003 | Steiner |
| 6,511,498 B1 | 1/2003 | Fumex |
| 6,517,578 B2 | 2/2003 | Hein |
| 6,544,281 B2 | 4/2003 | ElAttrache et al. |
| 6,554,852 B1 | 4/2003 | Oberlander |
| 6,558,386 B1 | 5/2003 | Cragg |
| 6,558,390 B2 | 5/2003 | Cragg |
| 6,569,187 B1 | 5/2003 | Bonutti et al. |
| 6,572,635 B1 | 6/2003 | Bonutti |
| 6,575,979 B1 | 6/2003 | Cragg |
| 6,610,080 B2 | 8/2003 | Morgan |
| 6,635,073 B2 | 10/2003 | Bonutti |
| 6,638,279 B2 | 10/2003 | Bonutti |
| 6,638,283 B2 | 10/2003 | Thal |
| 6,641,597 B2 | 11/2003 | Burkhart et al. |
| 6,660,023 B2 | 12/2003 | McDevitt et al. |
| 6,712,822 B2 | 3/2004 | Re et al. |
| 6,716,234 B2 | 4/2004 | Grafton et al. |
| 6,740,090 B1 | 5/2004 | Cragg et al. |
| 6,780,188 B2 | 8/2004 | Clark et al. |
| 6,790,210 B1 | 9/2004 | Cragg et al. |
| 6,805,697 B1 | 10/2004 | Helm et al. |
| 6,818,010 B2 | 11/2004 | Eichhorn et al. |
| 6,824,552 B2 | 11/2004 | Robison et al. |
| 6,830,570 B1 | 12/2004 | Frey et al. |
| 6,863,672 B2 | 3/2005 | Reiley et al. |
| 6,878,150 B1 | 4/2005 | McGuire et al. |
| 6,887,259 B2 | 5/2005 | Lizardi |
| 6,893,445 B1 | 5/2005 | Revie et al. |
| 6,899,716 B2 | 5/2005 | Cragg |
| 6,921,403 B2 | 7/2005 | Cragg et al. |
| 6,923,811 B1 | 8/2005 | Carl et al. |
| 6,923,814 B1 | 8/2005 | Hildebrand et al. |
| 6,936,052 B2 | 8/2005 | Gellman et al. |
| 6,955,683 B2 | 10/2005 | Bonutti |
| 6,960,214 B2 | 11/2005 | Burkinshaw |
| 6,972,027 B2 | 12/2005 | Fallin et al. |
| 6,991,636 B2 | 1/2006 | Rose |
| 6,994,719 B2 | 2/2006 | Grafton |
| 6,994,725 B1 | 2/2006 | Goble |
| 6,995,683 B2 | 2/2006 | Smithson et al. |
| 7,008,431 B2 | 3/2006 | Simonson |
| 7,025,770 B2 | 4/2006 | McGuire et al. |
| 7,029,490 B2 | 4/2006 | Grafton et al. |
| 7,048,754 B2 | 5/2006 | Martin et al. |
| 7,060,073 B2 | 6/2006 | Frey et al. |
| 7,067,132 B2 | 6/2006 | Grabstein et al. |
| 7,077,863 B2 | 7/2006 | Schmieding et al. |
| 7,087,058 B2 | 8/2006 | Cragg |
| 7,087,073 B2 | 8/2006 | Bonutti |
| 7,204,839 B2 | 4/2007 | Dreyfuss et al. |
| 7,214,232 B2 | 5/2007 | Bowman et al. |
| 7,217,279 B2 | 5/2007 | Reese |
| 7,217,290 B2 | 5/2007 | Bonutti |
| 7,235,091 B2 | 6/2007 | Thornes |
| 7,241,297 B2 | 7/2007 | Shaolian et al. |
| 7,258,692 B2 | 8/2007 | Thelen et al. |
| 7,261,016 B2 | 8/2007 | Miller |
| 7,309,338 B2 | 12/2007 | Cragg |
| 7,326,215 B2 | 2/2008 | Myers et al. |
| 7,331,263 B2 | 2/2008 | Erickson et al. |
| 7,488,322 B2 | 2/2009 | Brunnett et al. |
| 7,488,329 B2 | 2/2009 | Thelen et al. |
| 7,494,490 B2 | 2/2009 | Justin |
| 7,500,977 B2 | 3/2009 | Assell et al. |
| 7,503,920 B2 | 3/2009 | Siegal |
| 7,520,898 B2 | 4/2009 | Re et al. |
| 7,563,266 B2 | 7/2009 | Camino et al. |
| 7,578,836 B2 | 8/2009 | Justin et al. |
| 7,585,300 B2 | 9/2009 | Cha |
| 7,601,155 B2 | 10/2009 | Petersen |
| 7,601,165 B2 | 10/2009 | Stone |
| 7,604,636 B1 | 10/2009 | Walters et al. |
| 7,608,098 B1 | 10/2009 | Stone et al. |
| 7,608,108 B2 | 10/2009 | Bhatnagar et al. |
| 7,611,521 B2 | 11/2009 | Lubbers et al. |
| 7,621,912 B2 | 11/2009 | Harms et al. |
| 7,621,940 B2 | 11/2009 | Harms et al. |
| 7,651,509 B2 | 1/2010 | Bojarski et al. |
| 7,651,515 B2 | 1/2010 | Mack et al. |
| 7,658,751 B2 | 2/2010 | Stone et al. |
| 7,666,189 B2 | 2/2010 | Gerber et al. |
| 7,678,134 B2 | 3/2010 | Schmieding et al. |
| 7,749,250 B2 | 7/2010 | Stone et al. |

(56) References Cited

U.S. PATENT DOCUMENTS

| | | |
|---|---|---|
| 7,776,049 B1 | 8/2010 | Curran et al. |
| 7,803,173 B2 | 9/2010 | Burkhart et al. |
| 7,811,312 B2 | 10/2010 | Stevens et al. |
| 7,857,830 B2 | 12/2010 | Stone et al. |
| 7,875,057 B2 | 1/2011 | Cook et al. |
| 7,875,058 B2 | 1/2011 | Holmes, Jr. |
| 7,879,037 B2 | 2/2011 | Brunnett et al. |
| 7,887,551 B2 | 2/2011 | Bojarski et al. |
| 7,892,256 B2 | 2/2011 | Grafton et al. |
| 7,901,431 B2 | 3/2011 | Shumas |
| 7,905,903 B2 | 3/2011 | Stone et al. |
| 7,905,904 B2 | 3/2011 | Stone et al. |
| 7,909,851 B2 | 3/2011 | Stone et al. |
| 7,914,539 B2 | 3/2011 | Stone et al. |
| 7,918,874 B2 | 4/2011 | Siegal |
| 7,959,650 B2 | 6/2011 | Kaiser et al. |
| 7,963,972 B2 | 6/2011 | Foerster et al. |
| 7,981,117 B2 | 7/2011 | Newton et al. |
| 7,981,140 B2 | 7/2011 | Burkhart |
| 7,993,369 B2 | 8/2011 | Dreyfuss |
| 8,002,733 B2 | 8/2011 | Kraft et al. |
| 8,012,174 B2 | 9/2011 | ElAttrache et al. |
| 8,034,076 B2 | 10/2011 | Criscuolo et al. |
| 8,043,253 B2 | 10/2011 | Kraft et al. |
| 8,057,500 B2 | 11/2011 | Mitusina |
| 8,088,130 B2 | 1/2012 | Kaiser et al. |
| 8,114,088 B2 | 2/2012 | Miller |
| 8,118,836 B2 | 2/2012 | Denham et al. |
| 8,123,750 B2 | 2/2012 | Norton et al. |
| 8,128,640 B2 | 3/2012 | Harris et al. |
| 8,128,658 B2 | 3/2012 | Kaiser et al. |
| 8,128,669 B2 | 3/2012 | Bonutti |
| 8,133,231 B2 | 3/2012 | Martinek et al. |
| 8,137,382 B2 | 3/2012 | Denham et al. |
| 8,147,514 B2 | 4/2012 | Bonutti |
| 8,162,997 B2 | 4/2012 | Struhl |
| 8,172,846 B2 | 5/2012 | Brunnett et al. |
| 8,231,654 B2 | 7/2012 | Kaiser et al. |
| 8,231,674 B2 | 7/2012 | Albertorio et al. |
| 8,241,305 B2 | 8/2012 | Stone |
| 8,267,959 B2 | 9/2012 | Fallman |
| 8,273,106 B2 | 9/2012 | Stone et al. |
| 8,292,921 B2 | 10/2012 | Stone et al. |
| 8,298,262 B2 | 10/2012 | Stone et al. |
| 8,303,604 B2 | 11/2012 | Stone et al. |
| 8,317,825 B2 | 11/2012 | Stone |
| 8,337,525 B2 | 12/2012 | Stone et al. |
| 8,361,113 B2 | 1/2013 | Stone et al. |
| 8,372,124 B2 | 2/2013 | Paulk et al. |
| 8,398,678 B2 | 3/2013 | Baker et al. |
| 8,439,976 B2 | 5/2013 | Albertorio et al. |
| 8,512,375 B2 | 8/2013 | Torrie et al. |
| 8,591,578 B2 | 11/2013 | Albertorio et al. |
| 8,623,051 B2 | 1/2014 | Bojarski et al. |
| 8,632,569 B2 | 1/2014 | Stone et al. |
| 8,647,368 B2 | 2/2014 | Ducharme |
| 8,663,324 B2 | 3/2014 | Schmieding et al. |
| 8,668,718 B2 | 3/2014 | Euteneuer et al. |
| 8,702,718 B2 | 4/2014 | Bhatnagar et al. |
| 8,753,372 B2 | 6/2014 | Petros |
| 8,801,800 B2 | 8/2014 | Bagga et al. |
| 8,814,905 B2 | 8/2014 | Sengun et al. |
| 8,821,543 B2 | 9/2014 | Hernandez et al. |
| 8,821,544 B2 | 9/2014 | Sengun et al. |
| 8,821,545 B2 | 9/2014 | Sengun |
| 8,828,052 B2 | 9/2014 | Caborn et al. |
| 8,961,538 B2 | 2/2015 | Koogle, Jr. et al. |
| 9,173,652 B2 | 11/2015 | Lombardo et al. |
| 9,451,938 B2 * | 9/2016 | Overes ............... A61B 17/0057 |
| 2002/0019635 A1 | 2/2002 | Wenstrom et al. |
| 2002/0188301 A1 | 12/2002 | Dallara et al. |
| 2003/0032961 A1 | 2/2003 | Pelo et al. |
| 2003/0176919 A1 | 9/2003 | Schmieding |
| 2003/0195565 A1 | 10/2003 | Bonutti |
| 2003/0220646 A1 | 11/2003 | Thelen et al. |
| 2003/0233098 A1 | 12/2003 | Markworth |
| 2004/0010264 A1 | 1/2004 | Acker et al. |
| 2004/0010287 A1 | 1/2004 | Bonutti |
| 2004/0030346 A1 | 2/2004 | Frey et al. |
| 2004/0073227 A1 | 4/2004 | Dreyfuss et al. |
| 2004/0073306 A1 | 4/2004 | Eichhorn et al. |
| 2004/0092933 A1 | 5/2004 | Shaolian et al. |
| 2004/0138683 A1 | 7/2004 | Shelton et al. |
| 2004/0193217 A1 | 9/2004 | Lubbers et al. |
| 2004/0260300 A1 | 12/2004 | Gorensek et al. |
| 2004/0267277 A1 | 12/2004 | Zannis et al. |
| 2005/0015153 A1 | 1/2005 | Goble et al. |
| 2005/0033362 A1 | 2/2005 | Grafton |
| 2005/0070906 A1 | 3/2005 | Clark et al. |
| 2005/0137600 A1 | 6/2005 | Jacobs et al. |
| 2005/0137601 A1 | 6/2005 | Assell et al. |
| 2005/0143741 A1 | 6/2005 | Timmermans et al. |
| 2005/0177168 A1 | 8/2005 | Brunnett et al. |
| 2005/0187537 A1 | 8/2005 | Loeb et al. |
| 2005/0203527 A1 | 9/2005 | Carrison et al. |
| 2005/0228399 A1 | 10/2005 | Kubo et al. |
| 2005/0251159 A1 | 11/2005 | Ewers et al. |
| 2005/0251208 A1 | 11/2005 | Elmer et al. |
| 2006/0001518 A1 | 1/2006 | Hayashi et al. |
| 2006/0004369 A1 | 1/2006 | Patel et al. |
| 2006/0015108 A1 | 1/2006 | Bonutti |
| 2006/0074434 A1 | 4/2006 | Wenstrom et al. |
| 2006/0100631 A1 | 5/2006 | Sullivan et al. |
| 2006/0155329 A1 | 7/2006 | Grafton et al. |
| 2006/0178748 A1 | 8/2006 | Dinger et al. |
| 2006/0189993 A1 | 8/2006 | Stone |
| 2006/0190042 A1 | 8/2006 | Stone et al. |
| 2006/0212055 A1 | 9/2006 | Karabey et al. |
| 2006/0247641 A1 | 11/2006 | Re et al. |
| 2006/0247642 A1 | 11/2006 | Stone et al. |
| 2006/0282085 A1 | 12/2006 | Stone et al. |
| 2006/0293689 A1 | 12/2006 | Miller et al. |
| 2007/0010843 A1 | 1/2007 | Green |
| 2007/0010857 A1 | 1/2007 | Sugimoto et al. |
| 2007/0032800 A1 | 2/2007 | Ortiz et al. |
| 2007/0093840 A1 | 4/2007 | Pacelli et al. |
| 2007/0191853 A1 | 8/2007 | Stone |
| 2007/0213734 A1 | 9/2007 | Bleich et al. |
| 2007/0213735 A1 | 9/2007 | Saadat et al. |
| 2007/0225721 A1 | 9/2007 | Thelen et al. |
| 2007/0233151 A1 | 10/2007 | Chudik |
| 2007/0260259 A1 | 11/2007 | Fanton et al. |
| 2007/0288031 A1 | 12/2007 | Dreyfuss et al. |
| 2008/0027446 A1 | 1/2008 | Stone et al. |
| 2008/0027457 A1 | 1/2008 | Dienst et al. |
| 2008/0046009 A1 | 2/2008 | Albertorio et al. |
| 2008/0058816 A1 | 3/2008 | Philippon et al. |
| 2008/0065080 A1 | 3/2008 | Assell et al. |
| 2008/0065092 A1 | 3/2008 | Assell et al. |
| 2008/0071282 A1 | 3/2008 | Assell et al. |
| 2008/0109037 A1 | 5/2008 | Steiner et al. |
| 2008/0114399 A1 | 5/2008 | Bonutti |
| 2008/0132932 A1 | 6/2008 | Hoeppner et al. |
| 2008/0140078 A1 | 6/2008 | Nelson et al. |
| 2008/0140116 A1 | 6/2008 | Bonutti |
| 2008/0147063 A1 | 6/2008 | Cauldwell et al. |
| 2008/0154275 A1 | 6/2008 | Assell et al. |
| 2008/0161814 A1 | 7/2008 | McAllister et al. |
| 2008/0167660 A1 | 7/2008 | Moreau et al. |
| 2008/0188854 A1 | 8/2008 | Moser |
| 2008/0188935 A1 | 8/2008 | Saylor et al. |
| 2008/0208253 A1 | 8/2008 | Dreyfuss et al. |
| 2008/0249481 A1 | 10/2008 | Crainich et al. |
| 2008/0255613 A1 | 10/2008 | Kaiser et al. |
| 2008/0275431 A1 | 11/2008 | Stone et al. |
| 2008/0306483 A1 | 12/2008 | Iannarone |
| 2008/0312689 A1 | 12/2008 | Denham et al. |
| 2009/0012526 A1 | 1/2009 | Fletcher |
| 2009/0018654 A1 | 1/2009 | Schmieding et al. |
| 2009/0024130 A1 | 1/2009 | Lombardo |
| 2009/0054928 A1 | 2/2009 | Denham et al. |
| 2009/0062854 A1 | 3/2009 | Kaiser et al. |
| 2009/0076514 A1 | 3/2009 | Haines |
| 2009/0082805 A1 | 3/2009 | Kaiser et al. |

(56) References Cited

U.S. PATENT DOCUMENTS

| | | |
|---|---|---|
| 2009/0099554 A1 | 4/2009 | Forster et al. |
| 2009/0105775 A1 | 4/2009 | Mitchell et al. |
| 2009/0131940 A1 | 5/2009 | Brunnett et al. |
| 2009/0138015 A1 | 5/2009 | Conner et al. |
| 2009/0138042 A1 | 5/2009 | Thal |
| 2009/0143784 A1 | 6/2009 | Petersen et al. |
| 2009/0149858 A1 | 6/2009 | Fanelli |
| 2009/0157081 A1 | 6/2009 | Homan et al. |
| 2009/0160112 A1 | 6/2009 | Ostrovsky |
| 2009/0171359 A1 | 7/2009 | Sterrett |
| 2009/0192468 A1 | 7/2009 | Stone |
| 2009/0194446 A1 | 8/2009 | Miller et al. |
| 2009/0198258 A1 | 8/2009 | Workman |
| 2009/0216238 A1 | 8/2009 | Stark |
| 2009/0216243 A1 | 8/2009 | Re |
| 2009/0234451 A1 | 9/2009 | Manderson |
| 2009/0248029 A1 | 10/2009 | Paulos |
| 2009/0265002 A1 | 10/2009 | Re et al. |
| 2009/0306671 A1 | 12/2009 | McCormack et al. |
| 2009/0306711 A1 | 12/2009 | Stone et al. |
| 2009/0312763 A1 | 12/2009 | McCormack et al. |
| 2009/0312776 A1 | 12/2009 | Kaiser et al. |
| 2009/0312792 A1 | 12/2009 | Fallin et al. |
| 2009/0318961 A1 | 12/2009 | Stone et al. |
| 2009/0326538 A1 | 12/2009 | Sennett et al. |
| 2010/0049196 A1 | 2/2010 | Re |
| 2010/0057045 A1 | 3/2010 | Albritton, IV et al. |
| 2010/0076440 A1 | 3/2010 | Pamichev et al. |
| 2010/0082033 A1 | 4/2010 | Germain |
| 2010/0087857 A1 | 4/2010 | Stone et al. |
| 2010/0121332 A1 | 5/2010 | Crainich et al. |
| 2010/0121333 A1 | 5/2010 | Crainich et al. |
| 2010/0145384 A1 | 6/2010 | Stone et al. |
| 2010/0152739 A1 | 6/2010 | Sidebotham et al. |
| 2010/0160962 A1 | 6/2010 | Dreyfuss et al. |
| 2010/0185238 A1 | 7/2010 | Cauldwell et al. |
| 2010/0185283 A1 | 7/2010 | Baird et al. |
| 2010/0191241 A1 | 7/2010 | McCormack et al. |
| 2010/0211075 A1 | 8/2010 | Stone |
| 2010/0241121 A1 | 9/2010 | Logan et al. |
| 2010/0249786 A1 | 9/2010 | Schmieding et al. |
| 2010/0268275 A1 | 10/2010 | Stone et al. |
| 2010/0292732 A1 | 11/2010 | Hirotsuka et al. |
| 2010/0292792 A1 | 11/2010 | Stone et al. |
| 2010/0305709 A1 | 12/2010 | Metzger et al. |
| 2011/0015674 A1 | 1/2011 | Howard et al. |
| 2011/0015675 A1 | 1/2011 | Howard et al. |
| 2011/0022083 A1 | 1/2011 | DiMatteo et al. |
| 2011/0022084 A1 | 1/2011 | Sengun et al. |
| 2011/0046625 A1 | 2/2011 | Boileau et al. |
| 2011/0054526 A1 | 3/2011 | Stone et al. |
| 2011/0071551 A1 | 3/2011 | Singhatat et al. |
| 2011/0079627 A1 | 4/2011 | Cardinale et al. |
| 2011/0087247 A1 | 4/2011 | Fung et al. |
| 2011/0087280 A1 | 4/2011 | Albertorio |
| 2011/0087284 A1 | 4/2011 | Stone et al. |
| 2011/0098727 A1 | 4/2011 | Kaiser et al. |
| 2011/0106089 A1 | 5/2011 | Brunnett et al. |
| 2011/0106153 A1 | 5/2011 | Stone et al. |
| 2011/0125189 A1 | 5/2011 | Stoll, Jr. et al. |
| 2011/0152927 A1 | 6/2011 | Deng et al. |
| 2011/0160767 A1 | 6/2011 | Stone et al. |
| 2011/0160768 A1 | 6/2011 | Stone et al. |
| 2011/0184516 A1 | 7/2011 | Baird et al. |
| 2011/0208194 A1 | 8/2011 | Steiner et al. |
| 2011/0208239 A1 | 8/2011 | Stone et al. |
| 2011/0208240 A1 | 8/2011 | Stone et al. |
| 2011/0218538 A1 | 9/2011 | Sherman et al. |
| 2011/0218625 A1 | 9/2011 | Berelsman et al. |
| 2011/0224799 A1 | 9/2011 | Stone |
| 2011/0264141 A1 | 10/2011 | Denham et al. |
| 2011/0270278 A1 | 11/2011 | Overes et al. |
| 2011/0270293 A1 | 11/2011 | Malla et al. |
| 2011/0270306 A1 | 11/2011 | Denham et al. |
| 2011/0295279 A1 | 12/2011 | Stone et al. |
| 2011/0301708 A1 | 12/2011 | Stone et al. |
| 2011/0319896 A1 | 12/2011 | Papenfuss et al. |
| 2012/0004672 A1 | 1/2012 | Giap et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0053641 A1 | 3/2012 | Meridew |
| 2012/0059417 A1 | 3/2012 | Norton et al. |
| 2012/0059418 A1 | 3/2012 | Denham et al. |
| 2012/0071976 A1 | 3/2012 | May et al. |
| 2012/0089193 A1 | 4/2012 | Stone et al. |
| 2012/0095470 A1 | 4/2012 | Kaiser et al. |
| 2012/0095556 A1 | 4/2012 | Re et al. |
| 2012/0109142 A1 | 5/2012 | Dayan |
| 2012/0109156 A1 | 5/2012 | Overes et al. |
| 2012/0109194 A1 | 5/2012 | Miller et al. |
| 2012/0116452 A1 | 5/2012 | Stone et al. |
| 2012/0123474 A1 | 5/2012 | Zajac et al. |
| 2012/0150203 A1 | 6/2012 | Brady et al. |
| 2012/0150297 A1 | 6/2012 | Denham et al. |
| 2012/0150301 A1 | 6/2012 | Gamache et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0172986 A1 | 7/2012 | Stone et al. |
| 2012/0179254 A1 | 7/2012 | Saliman |
| 2012/0180291 A1 | 7/2012 | Oren et al. |
| 2012/0197271 A1 | 8/2012 | Astorino et al. |
| 2012/0203288 A1 | 8/2012 | Lange et al. |
| 2012/0209325 A1 | 8/2012 | Gagliano et al. |
| 2012/0245585 A1 | 9/2012 | Kaiser et al. |
| 2012/0253355 A1 | 10/2012 | Murray et al. |
| 2012/0290002 A1 | 11/2012 | Astorino |
| 2012/0290004 A1 | 11/2012 | Lombardo et al. |
| 2012/0290006 A1 | 11/2012 | Collins et al. |
| 2012/0296345 A1 | 11/2012 | Wack et al. |
| 2012/0296427 A1 | 11/2012 | Conner et al. |
| 2012/0303046 A1 | 11/2012 | Stone et al. |
| 2013/0012962 A1 | 1/2013 | Stone |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0046341 A1 | 2/2013 | Stone et al. |
| 2013/0053897 A1 | 2/2013 | Brown et al. |
| 2013/0072989 A1 | 3/2013 | Overes et al. |
| 2013/0085568 A1 | 4/2013 | Smith et al. |
| 2013/0096611 A1 | 4/2013 | Sullivan |
| 2013/0096612 A1 | 4/2013 | Zajac et al. |
| 2013/0110165 A1 | 5/2013 | Burkhart et al. |
| 2013/0131722 A1 | 5/2013 | Marchand et al. |
| 2013/0165972 A1 | 6/2013 | Sullivan |
| 2013/0190819 A1 | 7/2013 | Norton |
| 2013/0237997 A1 | 9/2013 | Arai et al. |
| 2013/0245700 A1 | 9/2013 | Choinski |
| 2013/0268000 A1 | 10/2013 | Harner et al. |
| 2013/0296931 A1 | 11/2013 | Sengun |
| 2013/0296936 A1 | 11/2013 | Burkhart |
| 2013/0317544 A1 | 11/2013 | Ferguson et al. |
| 2013/0325063 A1 | 12/2013 | Norton et al. |
| 2013/0345749 A1 | 12/2013 | Sullivan et al. |
| 2014/0005720 A1 | 1/2014 | Hirotsuka et al. |
| 2014/0025107 A1 | 1/2014 | Sack et al. |
| 2014/0163679 A1 | 6/2014 | Re et al. |
| 2014/0188163 A1 | 7/2014 | Sengun |
| 2016/0296223 A1 | 10/2016 | Monllor et al. |

FOREIGN PATENT DOCUMENTS

| | | |
|---|---|---|
| DE | 4243715 A1 | 7/1994 |
| DE | 19503504 A1 | 3/1996 |
| EA | 0611551 A1 | 8/1994 |
| EP | 153831 A2 | 9/1985 |
| EP | 253526 A1 | 1/1988 |
| EP | 0440371 A1 | 8/1991 |
| EP | 1155776 A2 | 11/2001 |
| EP | 1369089 A2 | 12/2003 |

(56) References Cited

FOREIGN PATENT DOCUMENTS

| EP | 2544607 A1 | 1/2013 |
|---|---|---|
| FR | 1166884 A | 11/1958 |
| FR | 2606996 A1 | 5/1988 |
| FR | 2676638 A1 | 11/1992 |
| GB | 2093353 A | 9/1982 |
| WO | 95011631 A1 | 5/1995 |
| WO | 9722301 A1 | 6/1997 |
| WO | 0044291 A | 8/2000 |
| WO | 0128457 A1 | 4/2001 |
| WO | 03007861 A1 | 1/2003 |
| WO | 2007/010389 A1 | 1/2007 |
| WO | 2008128075 A1 | 10/2008 |
| WO | 2009105880 A1 | 9/2009 |
| WO | 2011112371 A1 | 9/2011 |
| WO | 2012134999 A1 | 10/2012 |
| WO | 2012158583 A1 | 11/2012 |

OTHER PUBLICATIONS

Burkinshaw, U.S. Appl. No. 60/418,545, filed Oct. 15, 2002.
Chen et al., Journal of Orthopaedic Research, pp. 1432-1438, Nov. 2009.
Chen et al., Poster No. 538, 54th Annual Meeting of the Orthopaedic Research Society, San Francisco, CA Mar. 2008.
Cole et al., American Journal of Sports Medicine, vol. XX, No. X, 2011.
CONMED: Linvatec: Shoulder Restoration System Y-Knot 1.3mm All Suture Anchor, © 2011 Linvatec Corporation, a subsidiary of ConMed Corporation—CBR 3057 (4 pages).
European Search Report, EP 10173568, dated Nov. 30, 2010.
Extended European Search Report for Application No. EP 12164104 dated Jul. 11, 2012.
Extended European Search Report for Application No. EP14159656 dated Jun. 6, 2014.
HHS Tube, Fort Wayne Metals Research Products Corp., 2009.
International Search Report and Written Opinion for Application No. PCT/US2014/021231 dated Jun. 25, 2014.
International Search Report PCT/US2010/042264, dated Sep. 30, 2010.
Medtronic, The VISAO High-Speed Otologic Drill Catalog, 2007.
Perthes, German Surgery Periodical, vol. 85, Commermorative Publication, pp. 2-18, 1906.
Perthes, Ober Operationen bel habitueller Schulterluxaton, X, pp. 199-227, 85.
Sugaya et al., Journal of Bone and Joint Surgery, vol. 85-A, No. 5, pp. 878-884, May 2003.
U.S. Appl. No. 13/085,882, filed Apr. 13, 2011.
U.S. Appl. No. 13/303,849, filed Nov. 23, 2011.
U.S. Appl. No. 13/368,730, filed Feb. 8, 2012.
U.S. Appl. No. 13/588,586, filed Aug. 17, 2012.
U.S. Appl. No. 13/588,592, filed Aug. 17, 2012.
U.S. Appl. No. 13/783,804, filed Mar. 4, 2013.
U.S. Appl. No. 13/792,982, filed Mar. 11, 2013.
U.S. Appl. No. 61/679,336, filed Aug. 3, 2012.

* cited by examiner

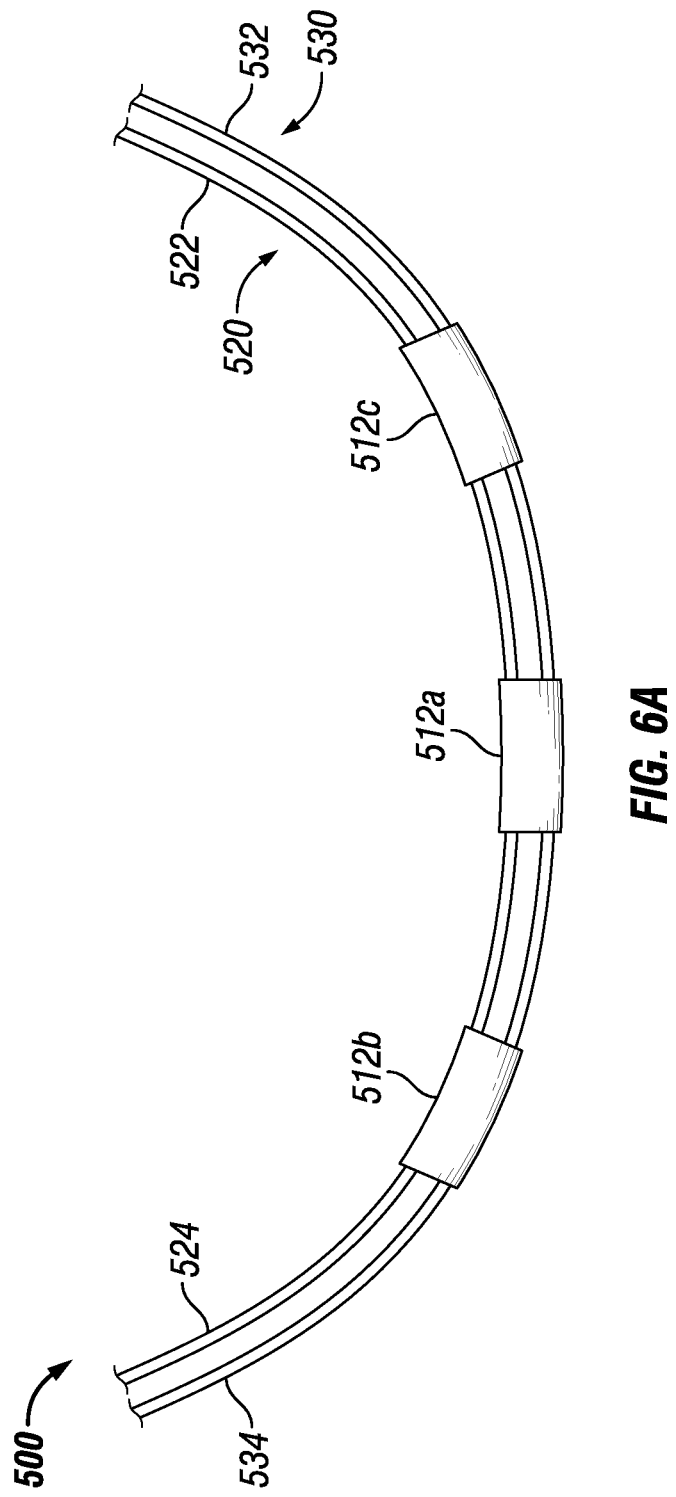

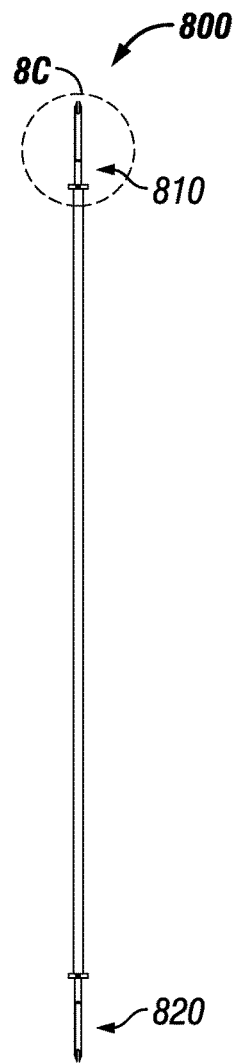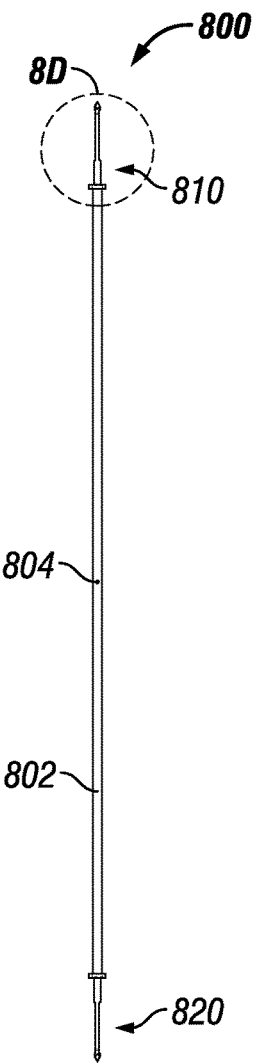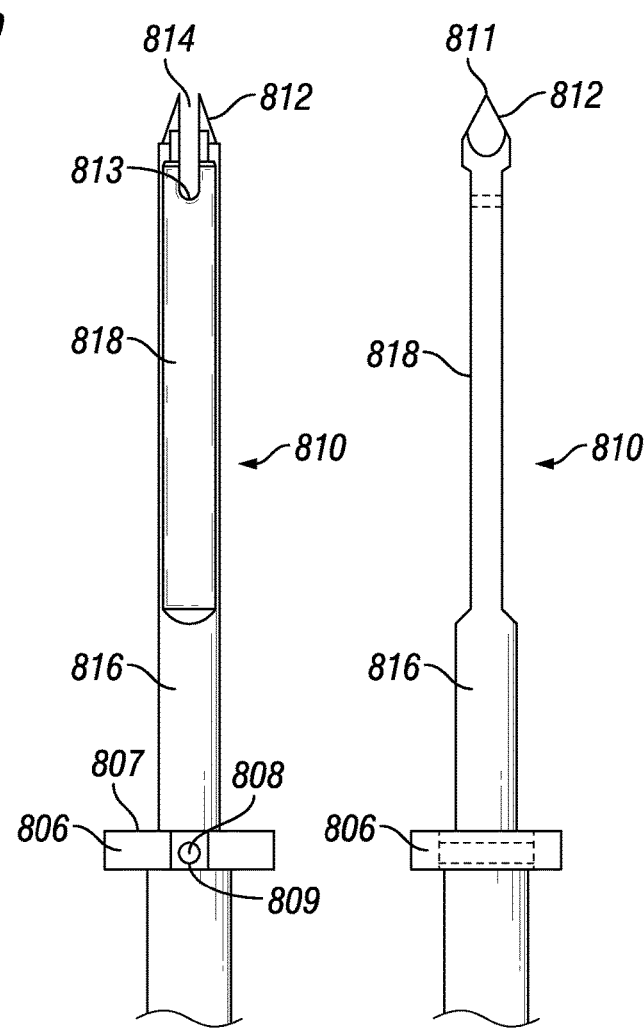
FIG. 8A          FIG. 8B          FIG. 8C          FIG. 8D

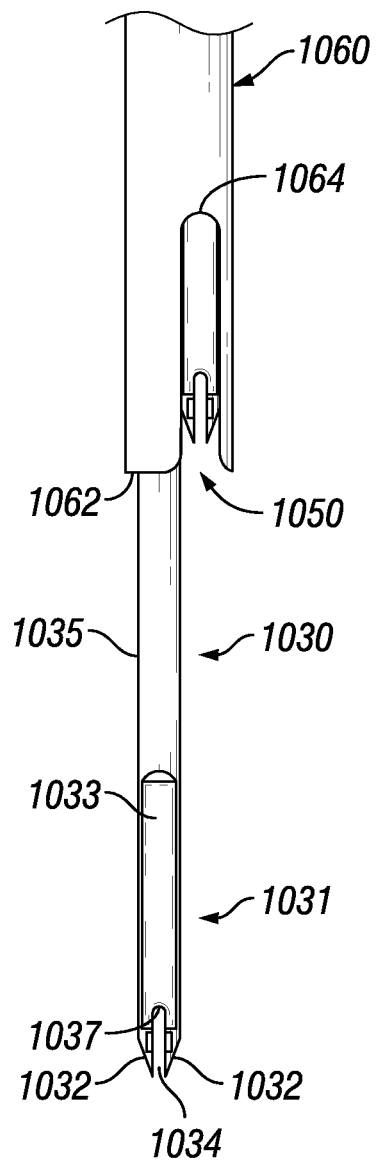
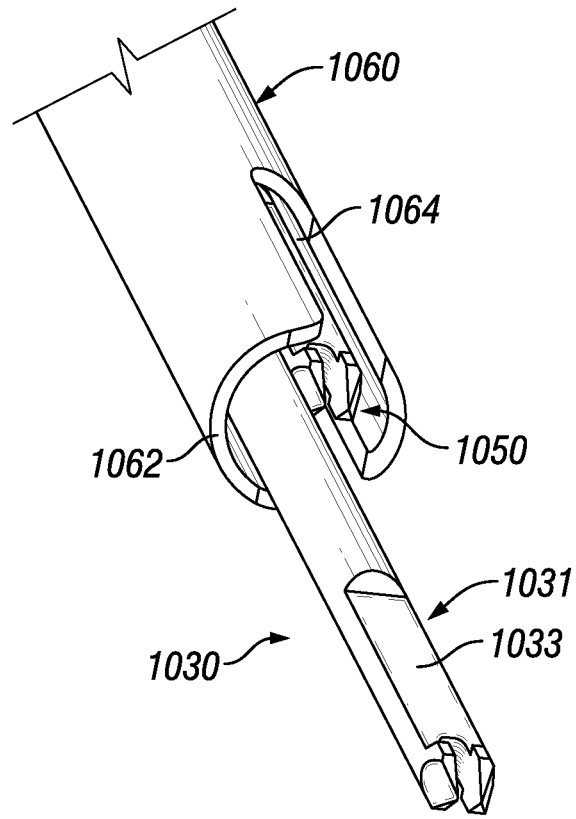
FIG. 11B
FIG. 11C

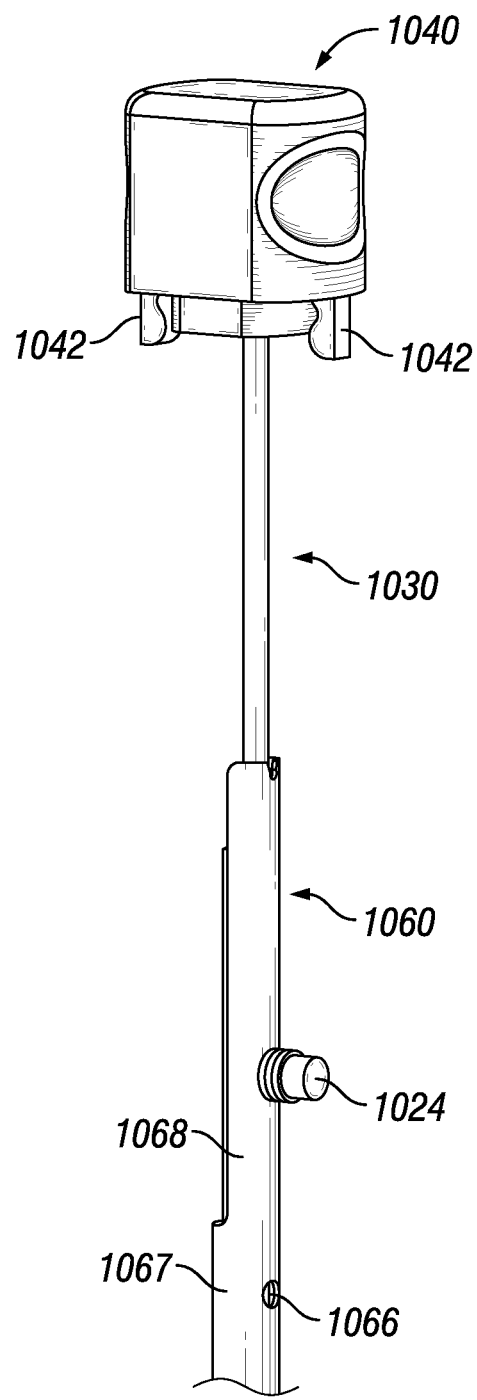 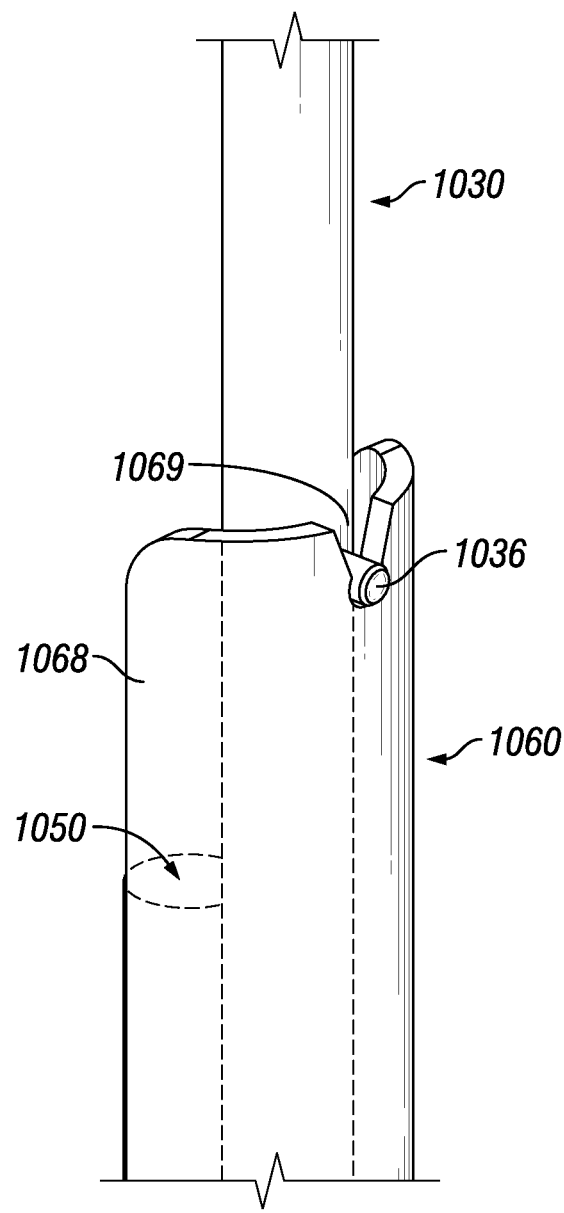
FIG. 11D     FIG. 11E

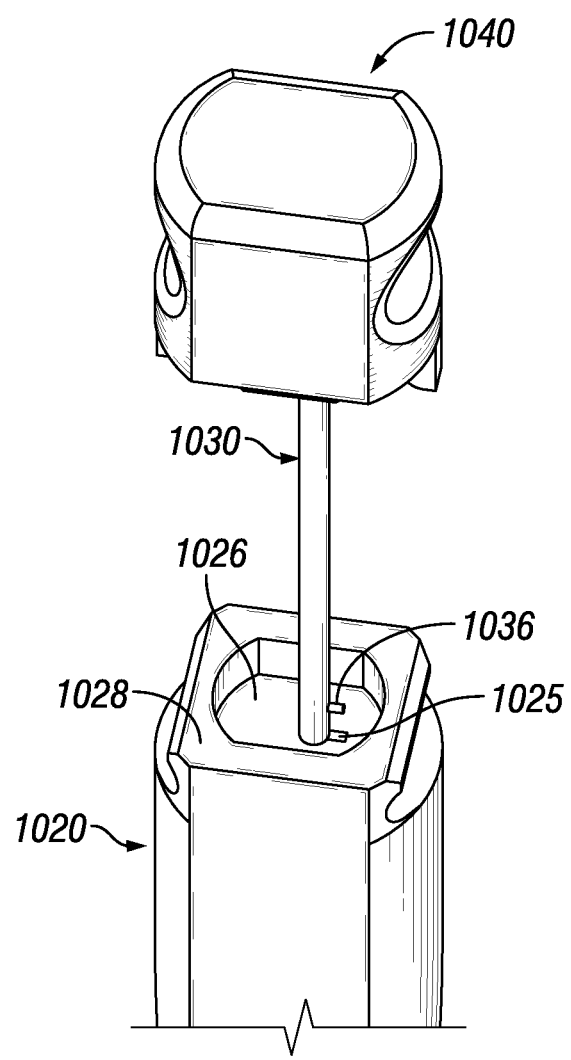
FIG. 13A
FIG. 13B

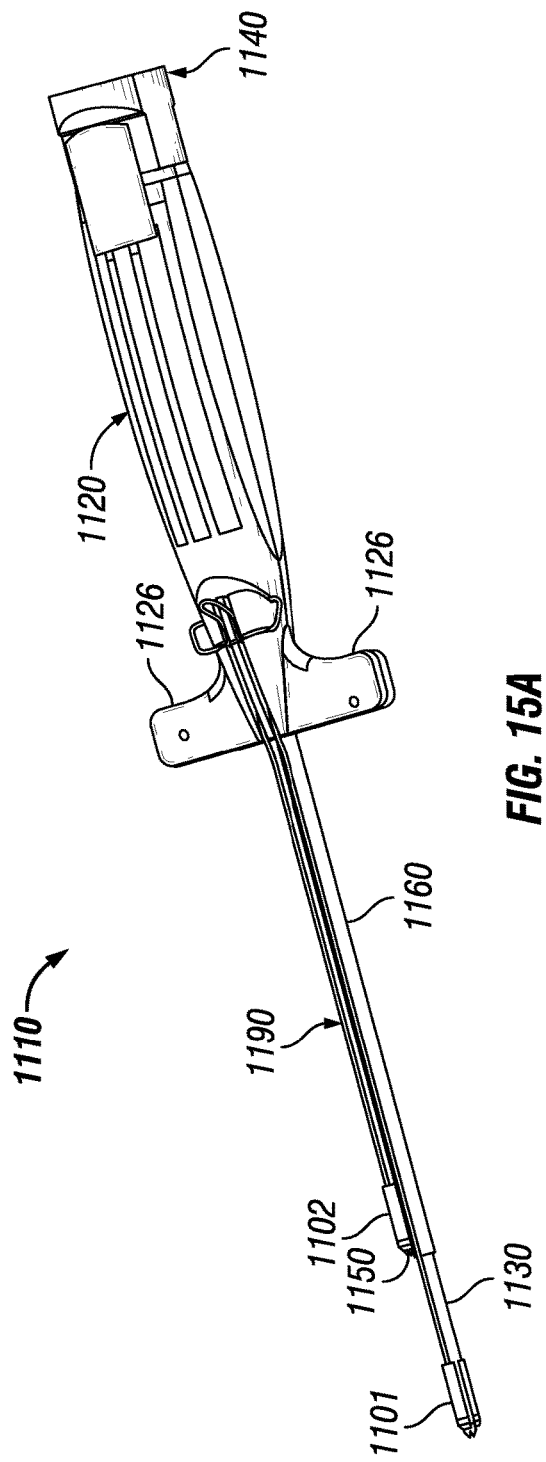
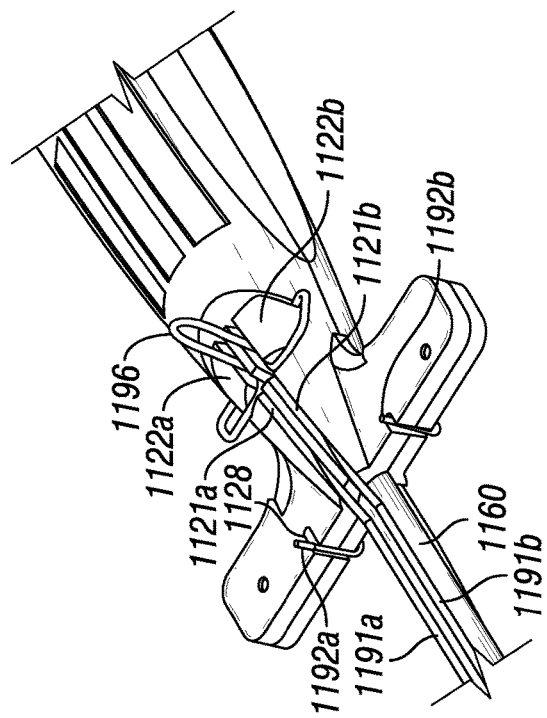
FIG. 15A
FIG. 15B

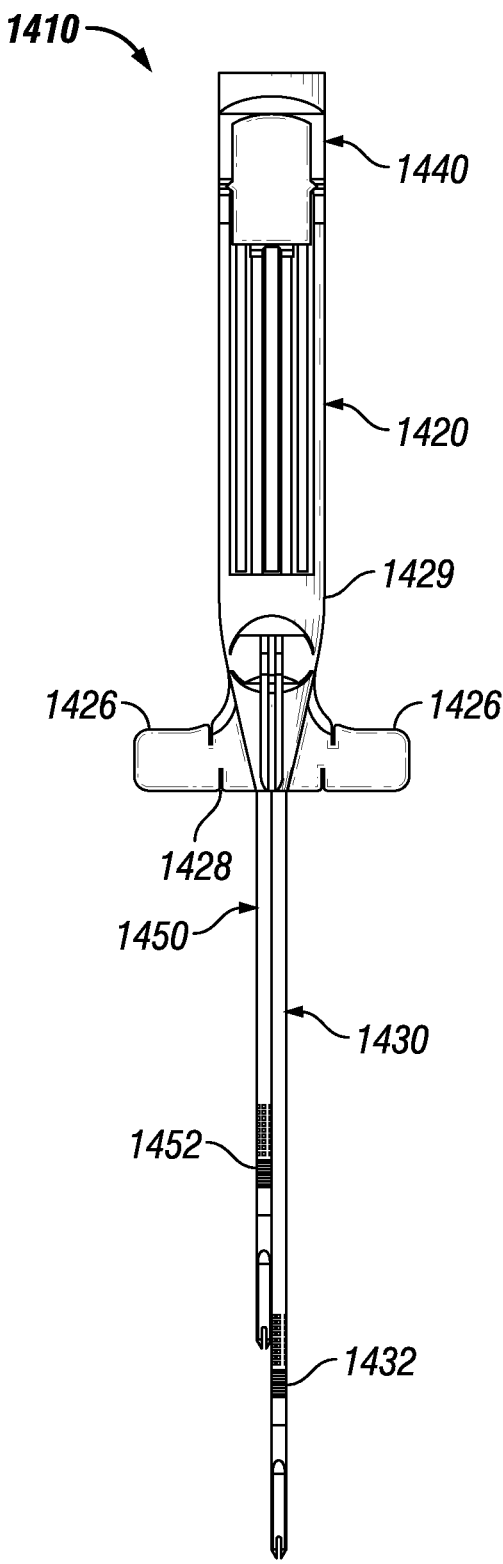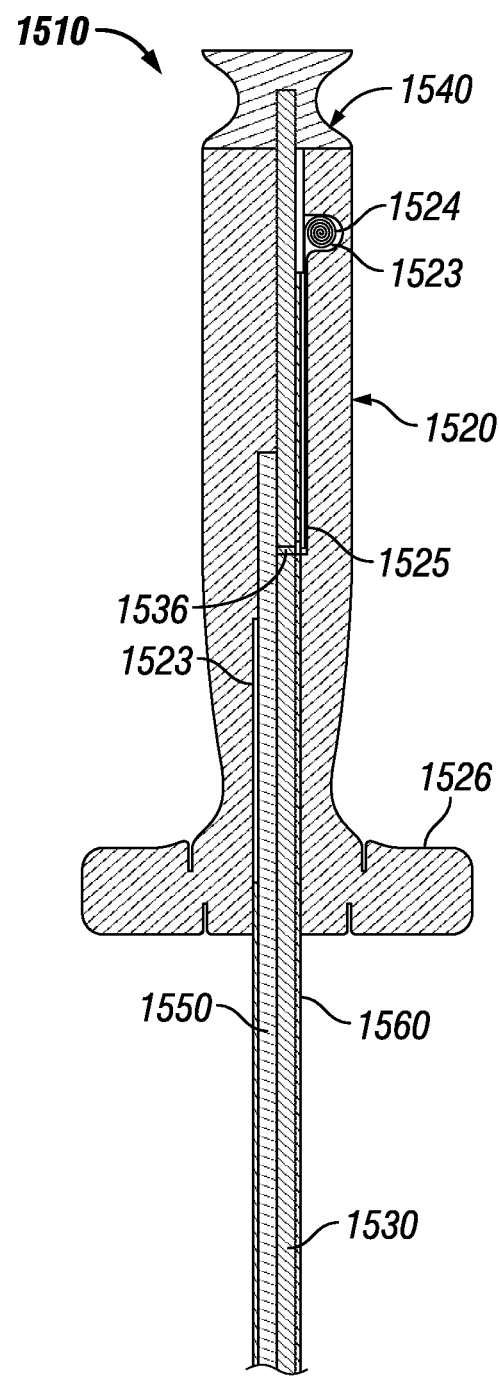
FIG. 18
FIG. 19

INSTRUMENTS AND METHODS OF SOFT TISSUE FIXATION

CROSS-REFERENCE TO RELATED APPLICATION

The present application is a continuation-in-part of U.S. patent application Ser. No. 14/573,538, filed Dec. 17, 2014, the disclosure of which is incorporated herein by referenced.

BACKGROUND OF THE INVENTION

Surgical repair of soft tissue often requires damaged soft tissue or replacement graft tissue to be positioned against adjacent soft tissue or hard tissue (e.g., bony structure). The objective is to form a healing interface so that microscopic connections can be formed during the healing process, thereby adjoining the contacting tissue structures. In order to achieve this objective, it is important to maintain and minimize disruptions at this interface. Otherwise these connections and ultimately the entire repair can be compromised.

In one example, a portion of torn tissue that is typically connected to a bony structure, such as a labrum, rotator cuff, Achilles tendon, patellar tendon, or the like may be connected or reconnected to the bony structure. This is typically achieved by positioning the torn tissue as close to its natural location as possible and anchoring the tissue to the bone. Compression between the bone and tissue is desirable to help maintain the healing interface and to instigate the healing process.

Generally, an anchoring support and a filament attached to the anchoring support are utilized in soft tissue reparation. A surgical knot is typically created to hold the tissue against the bone. However, these surgical knots are subject to loosening, which can reduce or eliminate desirable compression and can lead to undesirable movement of the healing interface, which may result in a suboptimal repair or total failure of the repair.

Despite the use and benefits of such devices and techniques, such devices and techniques can benefit from alternative devices and securement techniques.

BRIEF SUMMARY OF THE INVENTION

In one aspect of the present disclosure, an inserter assembly for inserting anchors into bone includes a handle having a handle body. A sleeve is partially disposed within the handle body and has a passageway extending through the sleeve in a proximal-distal direction. A first inserter is partially disposed within the handle body and the passageway of the sleeve. The first inserter is configured to retain a first anchor for insertion thereof into bone. A second inserter is partially disposed within the handle body and passageway of the sleeve. The first inserter is configured to retain a second anchor for insertion thereof into bone. The inserter assembly has a first configuration in which the sleeve is connected to the first inserter so that the first inserter and sleeve are moveable together relative to the handle body, and a second configuration in which the sleeve is connected to the handle body and disconnected from the first inserter so that the first inserter is moveable relative to the sleeve.

In another aspect of the present disclosure, an inserter assembly for inserting anchors into bone includes a handle having a handle body. A first inserter is disposed within the handle body and is fixedly connected thereto. The first inserter has an insertion end configured to retain a first anchor for insertion thereof into bone. A second inserter is slidably disposed within the handle body and has an insertion end configured to retain a second anchor for insertion thereof into bone.

In a further aspect of the present disclosure, an inserter assembly for soft tissue repair includes an inserter handle having a handle body. A first inserter is slidably disposed within the handle body and has an insertion end extending distally from the handle body. A first anchor defines a passageway extending therethrough and is mounted to the insertion end of the first inserter for insertion thereof into bone. A second inserter is fixedly connected to the handle body and has an insertion end extending distally from the handle body. A second anchor defines a passageway extending therethrough and is mounted to the insertion end of the second inserter for insertion thereof into bone. A sleeve is slidably disposed within the handle body and positioned about respective portions of the first and second inserters. The sleeve is moveable relative to the second inserter between a first and second position. A length of filament extends through the passageways of the first and second inserters.

BRIEF DESCRIPTION OF THE DRAWINGS

The features, aspects, and advantages of the present invention will become better understood with regard to the following description, appended claims, and accompanying drawings in which:

FIG. 6A illustrates yet a further embodiment of a tissue fixation assembly.

FIG. 8A is a front view of another embodiment inserter device.

FIG. 8B is a side view of the inserter device of FIG. 8A.

FIG. 8C is an enlarged view of dashed circle 8C of FIG. 8A.

FIG. 8D is an enlarged view of dashed circle 8D of FIG. 8B.

FIG. 11B is an enhanced front view of a distal end of the inserter assembly of FIG. 11A.

FIG. 11C is an enhanced bottom perspective view of the distal end of the inserter assembly of FIG. 11A.

FIG. 11D is a partial perspective view of first and second inserters, a sleeve, and a ball detent of inserter assembly of FIG. 11A.

FIG. 11E is an enhanced partial transparent view of the first and second inserters and sleeve of FIG. 11D.

FIG. 13A is a perspective view of the inserter assembly of FIG. 11A being depicted in another stage of the transition phase thereof.

FIG. 13B is an enhanced top perspective view of the inserter assembly of FIG. 13A.

FIG. 15A is a front perspective view of an inserter assembly according to a further embodiment of the present disclosure.

FIG. 15B is an enhanced perspective view of the inserter assembly of FIG. 15A.

FIG. 18 is a front view of an inserter assembly according to a still further embodiment of the present disclosure.

FIG. 19 is cross-sectional view an inserter assembly according to an even further embodiment of the present disclosure taken along a midline thereof.

DETAILED DESCRIPTION

The fixation devices, assemblies, systems, and associated methods of use of the present invention are intended for use in the repair, reattachment, replacement, or otherwise securement of tissue, including both hard tissue (e.g., bone or the like) and soft tissue. Soft tissue may be, for example, meniscus, cartilage, capsule, ligaments and tendons, replacement grafts of any of these soft tissues, or the like. While many of the exemplary methods disclosed herein are directed towards the use of fixation assemblies, systems, and methods involving a filament/suture anchor for implantation into a bone hole, it is envisioned that such assemblies, systems, and methods described herein can be utilized with a hard/solid anchor in lieu of or in conjunction with a filament/suture anchor. In addition, it should be understood that the following devices and methods may be utilized in both open surgery and arthroscopic surgery.

As used herein unless stated otherwise, the term "anterior" means toward the front part of the body or the face, the term "posterior" means toward the back of the body. The term "medial" means closer to or toward the midline of the body, and the term "lateral" means further from or away from the midline of the body.

Also, when referring to specific directions in the following discussion of certain device, the terms "proximal" and "distal" are to be understood in regard to the device's orientation and position during exemplary application to human body. Thus, as used herein, the term "proximal" means closer to the operator or in a direction toward the operator, and the term "distal" means more distant from the operator or in a direction away from the operator.

In addition, the terms "about," "generally" and "substantially" are intended to mean that slight deviations from absolute are included within the scope of the term so modified.

Also, as used herein, the term "filament" or "filamentary" is defined as a suture or other thread-like material. Such filaments may be constructed of synthetic material (e.g., PLGA, UHMWPE (ultra high molecular weight polyethylene), polyester, PEEK, nylon, polypropylene, aramids (for example Kevlar®-based fibers) or the like, or blends thereof), organic material (silk, animal tendon, or the like or blends thereof), or blends of both one or more organic materials and one or more synthetic materials. Alternatively, filaments may include thin metal wires. While any of these materials may be used, it is preferable, and is disclosed herein, that the various filaments or filamentary aspects of the present invention be constructed out of suture, such as UHMWPE, polyester or blends thereof.

Figure 1A:
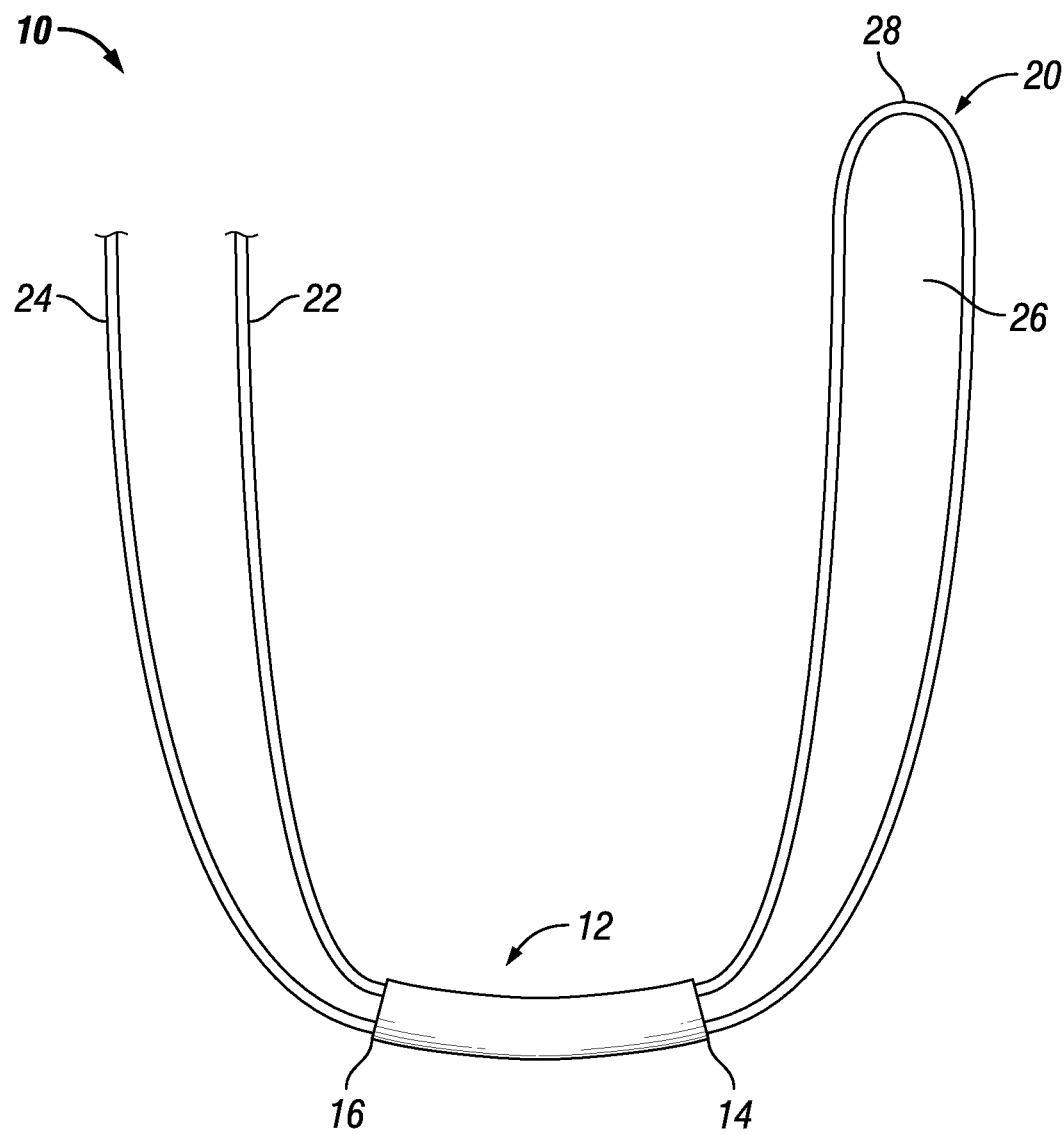
FIG. 1A illustrates one embodiment of a tissue fixation assembly.

FIG. 1A depicts an embodiment of a fixation assembly 10. Fixation assembly 10 includes a filamentary sleeve 12 and a length of filament 20. Sleeve 12 includes a first opening and a second opening 16 and a passageway extending therethrough. In one example, the sleeve 12 can be the Iconix® all suture anchor system (Stryker Corporation, Kalamazoo, Mich.). Other configurations are also envisioned, examples of which are disclosed in U.S. application Ser. No. 13/783, 804, filed Mar. 4, 2013; Ser. No. 13/303,849, filed Nov. 23, 2011; Ser. No. 13/588,586, filed Aug. 17, 2012; Ser. No. 13/588,592, filed Aug. 17, 2012; Ser. No. 14/104,677, filed Dec. 12, 2013; Ser. No. 14/298,295, filed Jun. 6, 2014; and U.S. Pat. Nos. 5,989,252 and 6,511,498, the entireties of which are incorporated by reference herein as if fully set forth herein and all of which are assigned to the same entity as the present invention.

Filament 20 is folded over itself at a location along its length to form a loop 26 that defines a loop-end of filament 20 and an apex 28. Filament 20 is disposed at least partially within the passageway of the sleeve 12 such that the loop-end extends from one end of sleeve 12 and first and second free ends 22 and 24 of filament 20 extend from the opposite end of sleeve 12.

Figure 1B:
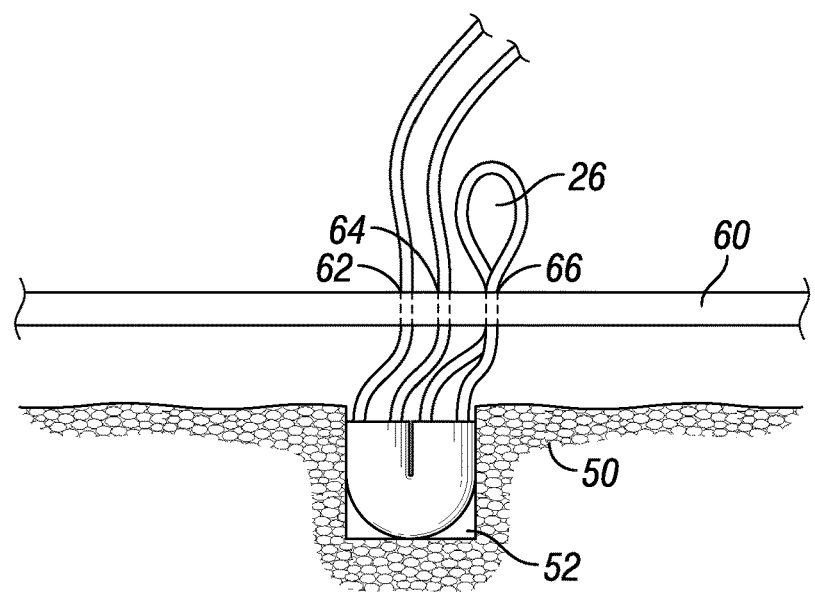
FIGS. 1B and 1C are schematic side views of a configuration of the fixation assembly of FIG. 1A.
Figure 1C:
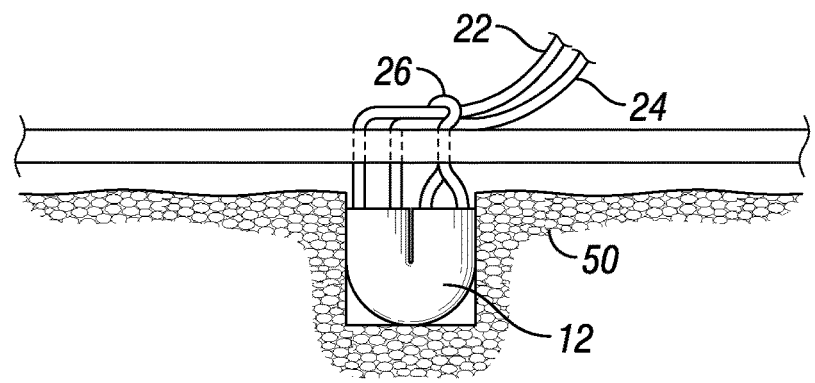
Figure 1D:
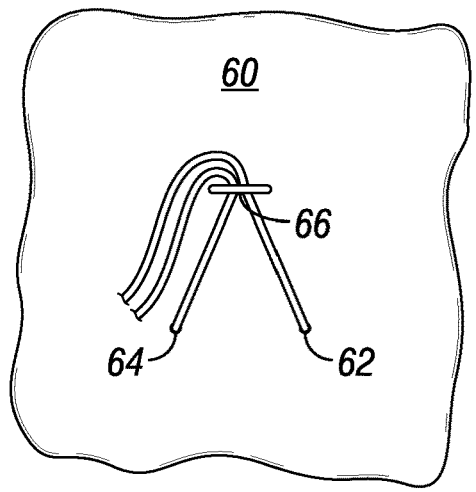
FIGS. 1D and 1E are schematic top views of the configuration of the fixation assembly of FIG. 1A.

FIGS. 1B-1D depict an embodiment method of using fixation assembly 10. This method may be utilized in many procedures in which soft tissue is to be attached or otherwise anchored to bone. For ease of illustration, the various disclosed exemplary methods and uses throughout will be described with reference to a rotator cuff repair, though these methods and uses may be translated to other soft tissue repairs. In such a method, a bone hole 52 is drilled or otherwise formed in bone 50. An inserter device (not shown) may be attached to sleeve 12 such that sleeve 12 and inserted into bone hole 52 as shown in FIGS. 1B and 1C. At this point, the loop-end and first and second free ends 22 and 24 extend from bone hole 52 and are tensioned to seat sleeve 12 into an anchoring position within bone hole 52.

With the loop-end and free ends 22, 24 extending from bone hole 52, first free end 22 is passed through tissue 60 at a first tissue penetration location 62, second free end 24 is passed through a second tissue penetration location 64, and the loop-end is passed through a third tissue penetration location 66. In some embodiments, free ends 22 and 24 may be passed through the same tissue penetration location. Free ends 22 and 24 are passed through loop 26 and continuously tensioned until loop 26 cinches down around free ends 22 and 24. As loop 26 is cinched, tissue 60 is drawn closer to and compressed against bone 50 surrounding hole 52.

Free ends 22 and 24 are available to be utilized in conjunction with at least one additional anchor (filamentary or the like), for example, in the formation of a suture bridge. As such, no knots need be formed and continuous tension may be applied to free ends 22 and 24 keeping loop 26 cinched and tissue 60 compressed against bone 50.

The tissue penetration locations 62, 64 and 66 can be arranged in any number of configurations and may generally form a triangular pattern as in FIG. 1D. For example, the first, second and third penetrations 62, 64, 66 can be situated to form an equilateral triangle. In another embodiment, an isosceles triangle may be formed in which first and second penetrations 62 and 64 are substantially equally spaced from third penetration 66. In a further embodiment, penetration 62, 64, 66 may be arranged in the form of a right triangle such that first or second penetration is closer to the third penetration 66 than the other penetration. Other triangular configurations may also be utilized. In addition, penetration locations 62, 64, 66 may be located all within an area directly above bore hole 52, or one or more penetration may be located beyond the periphery of bore hole 52.

Figure 1E:
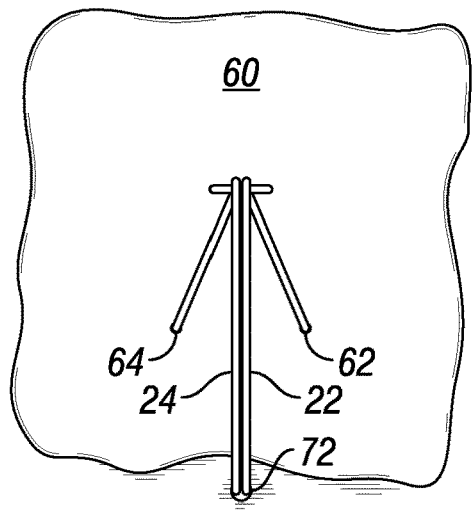

In some circumstances, a particular triangular configuration may be chosen to help direct tension applied to the tissue via filament 20. For example, as depicted in FIG. 1D, tissue 60 may be a rotator cuff. Third penetration 66, as depicted, is located medial of first and second penetrations 62 and 64, which are aligned in a row in an anterior/posterior direction. First and second penetrations 62 and 64 are equally spaced from third penetration 66 to form an isosceles or equilateral triangular pattern. Tension is applied to free ends 22 and 24 in either the lateral or medial direction, which cinches loop 26. As loop 26 becomes tighter, the resultant tension applied to the rotator cuff 60 is in a direction which substantially bisects first and second penetrations 62, 64, which is at least partially due to the symmetrical nature of the depicted triangular configuration. Thus, in the example provided in FIG. 1E, the rotator cuff 60 would be tensioned in substantially the medial/lateral direction toward the humerus. Free ends may then be directed over apex and fixed to a second and/or third bone anchor 72 that is disposed lateral to sleeve 12.

In another example, a right-triangular pattern may be formed in which first penetration 62 is closer to third penetration 66. When free ends 22 and 24 are advanced through loop 26 and tensioned, the resultant tension applied to the rotator cuff may be in both the lateral/medial and anterior/posterior directions.

It should be understood that a triangular configuration comprised of penetrations 62, 64 and 66 may have alternative orientations from that depicted in FIG. 1D. For instance, in one embodiment, the triangular pattern shown in FIG. 1D may be mirrored such that third penetration 66 is located lateral to first and second penetrations 62, 64. Alternatively, the triangular pattern may be oriented orthogonally from the depicted location such that third penetration 66 is located more anteriorly or more posteriorly than first and second penetrations 62, 64. The specific orientation and positioning of the penetration locations (indeed, the configuration of any of the disclosed devices and methods herein) may be dependent on the type of repair required. For example, for the rotator cuff, such positioning can be dependent on whether the injury is a full thickness, partial thickness, PASTA lesion, trans-tendinous, or the like.

Figure 2A:
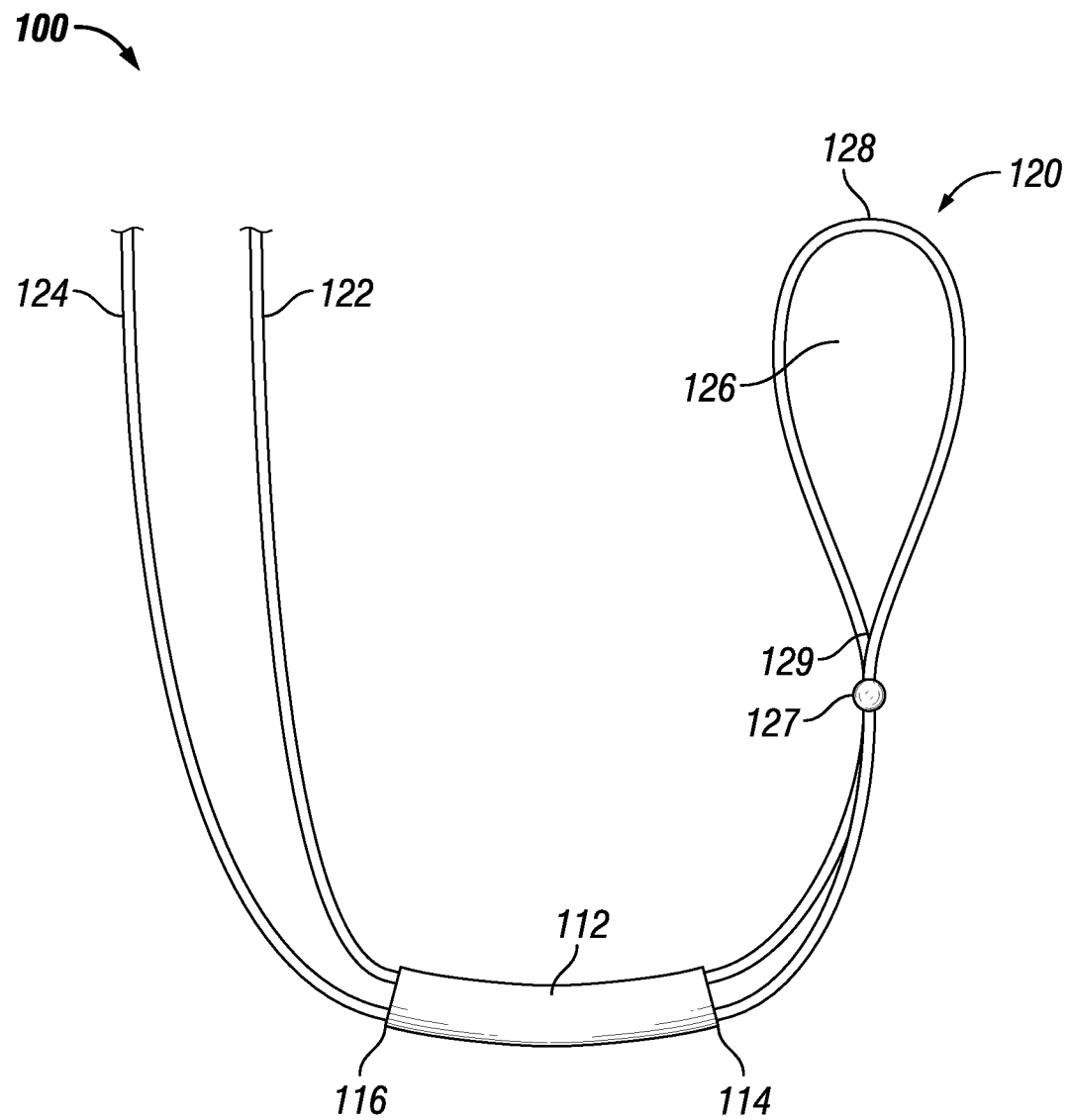
FIG. 2A illustrates another embodiment of a tissue fixation assembly.

FIG. 2A depicts an alternative embodiment fixation assembly 100. Fixation assembly 100 is similar to fixation assembly 10 in that it includes a filamentary sleeve 112 and length of filament 120, which can be the same as filamentary sleeve 12 and length of filament 20, respectively. However, fixation assembly 100 differs in that filament 120 is joined at a junction 127 to form a loop 126 that defines a loop-end of filament 120, an apex 128, and a crotch 129. Junction 127 may be formed by a splice, such as a Brummel splice, by braiding filament 120 together at the junction location, by mechanical means, such as a clamp, or by some other means as is known in the art.

Figure 2B:
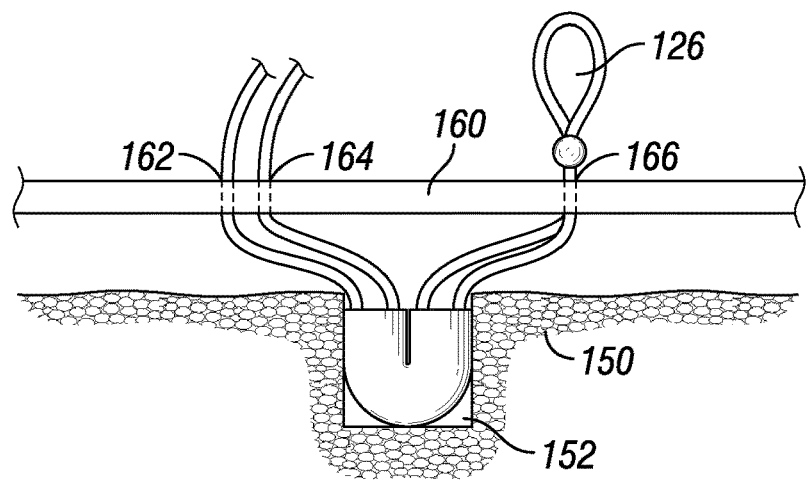
FIGS. 2B and 2C are schematic side views of a configuration of the tissue fixation assembly of FIG. 2A.
Figure 2C:
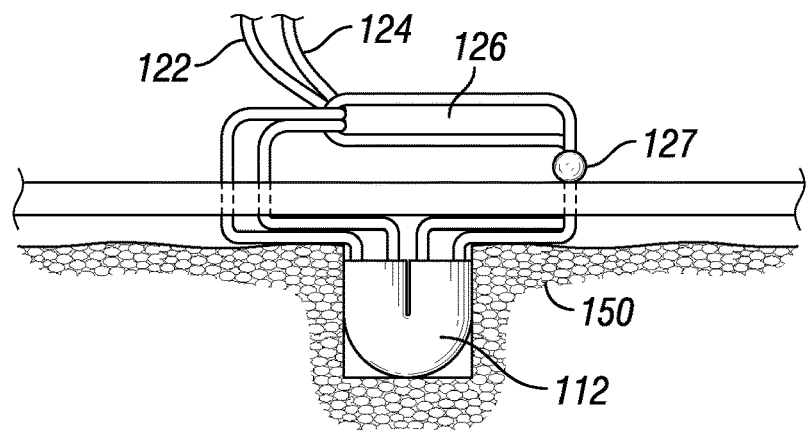
Figure 2D:
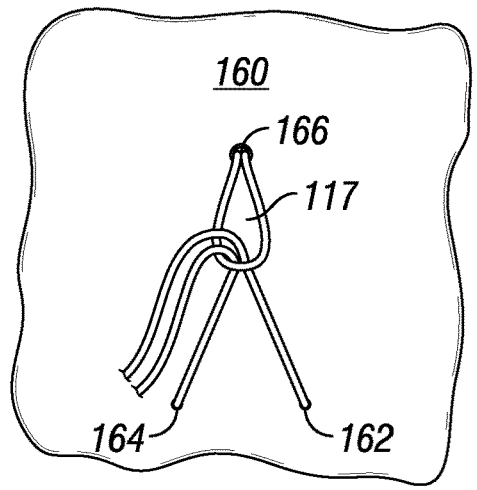
FIG. 2D is a schematic top view of the configuration of the fixation assembly of FIG. 2A.

FIGS. 2B-2D depict a method of using fixation assembly 100. The method of using fixation assembly 100 is similar to the method of using fixation assembly 10 in that sleeve 112 is inserted and anchored into a bone hole 152. Thereafter, first and second free ends 122, 124 of filament 120 are passed through tissue 160 at first and second tissue penetration locations 162, 164, respectively, while the loop-end is passed through a third tissue penetration location 166. Such penetration locations 162, 164, 166 may be arranged in various triangular patterns as previously described.

As shown in FIGS. 2B-2D, at least a portion of loop 126, and optionally all of the loop 126 and junction 127, is passed through tissue 160. In particular, as illustrated, when free ends 122 and 124 are tensioned, loop 126 remains above the tissue without reentering penetration 166. Junction 127 may be configured such that it collapses over penetration 166 or is otherwise structured so that it cannot be passed back through tissue 160. For example, junction 127 can have braiding or an additional sleeve/skirt attached to junction 127 that has a narrow profile while passing through tissue 160 in one direction, while collapsing and expanding when there is an attempted advancement back through tissue 160. In another example, a thermoreactive material, such as hydrogel or Nitinol can be applied at the location such that it expands upon the application of heat once passed through tissue 160. Such a configuration may assist in compression of the tissue, at location 166, against underlying bone.

In another embodiment, loop 126 and junction 127 may not completely exit penetration 166 or may be readily passed back into and through penetration 166. Thus, as free ends 122 and 124 are tensioned, a portion of loop 126 is pulled into sleeve 112 as another portion of loop 126 cinches down around free ends 122 and 124 resulting in a configuration that has the appearance of FIG. 1D.

Figure 3A:
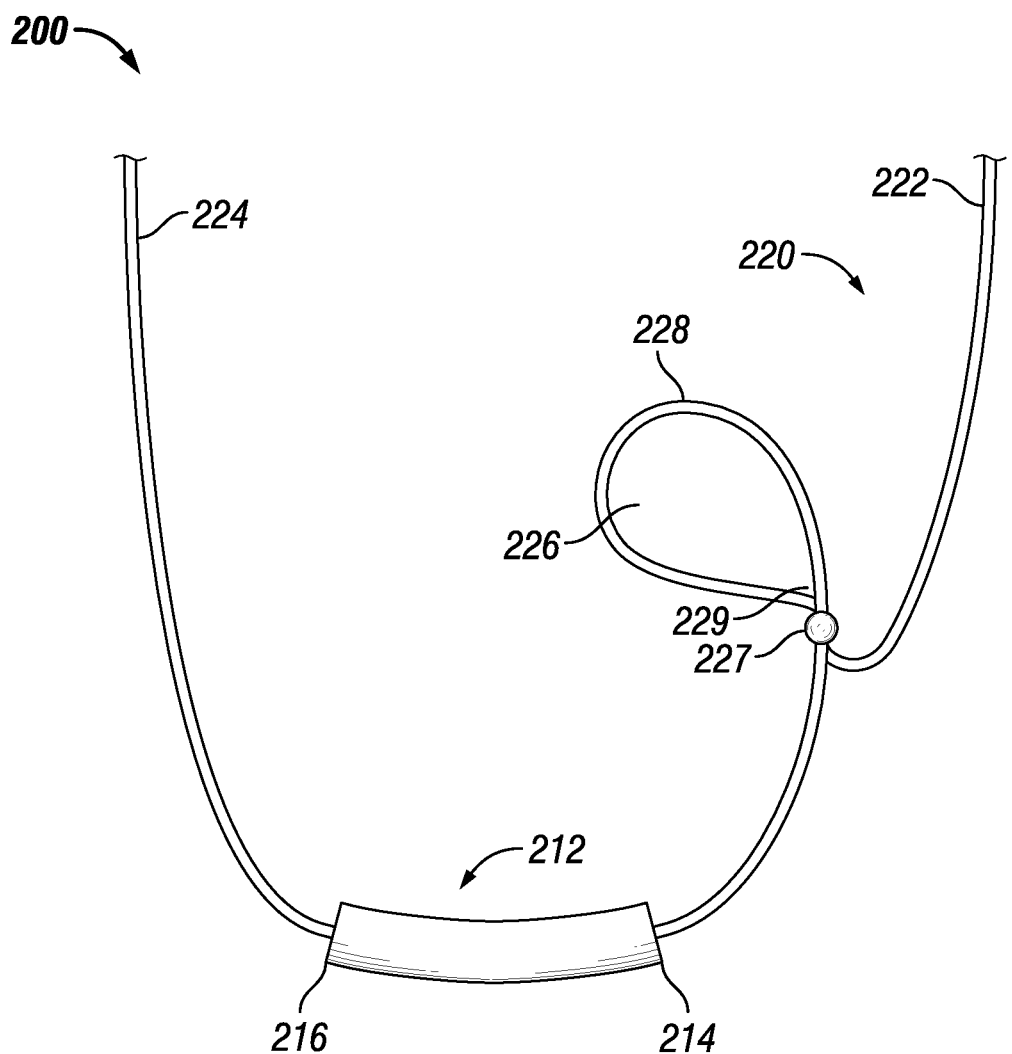
FIG. 3A illustrates a further embodiment of a tissue fixation assembly.

FIG. 3A depicts another fixation assembly embodiment 200. Fixation assembly 200 also includes a filamentary sleeve 212 and length of filament 220. Sleeve 212 may be the same as filamentary sleeve 12. Filament 220 may be similar to filament 120 such that filament 220 includes a junction forming a loop 226 that defines a loop-end of filament 220, a crotch 229 and an apex 228. Filament 220 also includes a first free end 222 and a second free end 224 that each extend from the junction. In some embodiments, first free end 222 may have a shorter length than second free end 224, a longer length than free end 224 or the same length as free end 224, but, regardless, both may have a length sufficient to be used in conjunction with an arthroscopic cannula. When sleeve 212 and filament 220 are assembled, second free end 224 passes through the passageway of sleeve 212 and out of the second end 216, while loop 226 and first free end 222 extend from the first end 214 of sleeve 212.

Figure 3B:
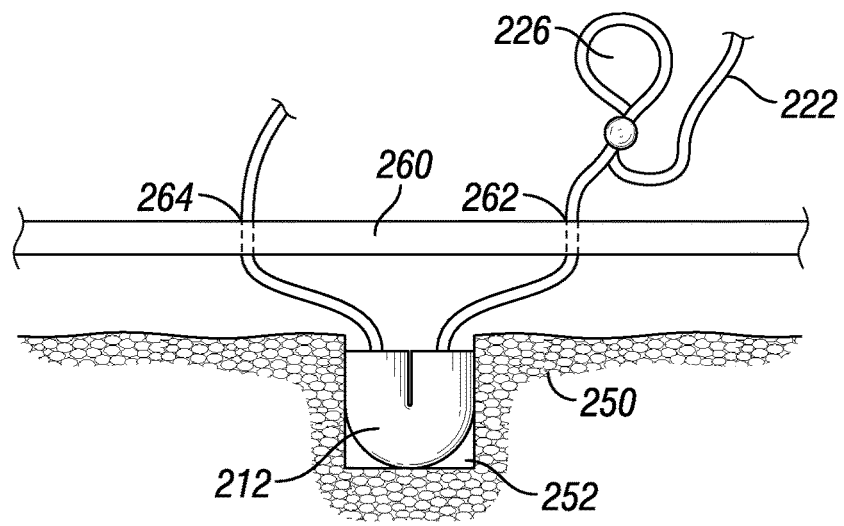
FIGS. 3B and 3C are schematic side views of a configuration of the tissue fixation assembly of FIG. 3A.
Figure 3C:
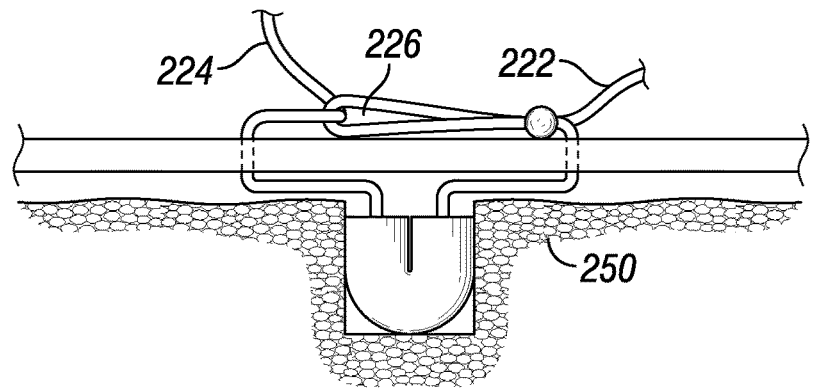

FIGS. 3B-3E depict one exemplary method embodiment of using fixation assembly 200. As shown in FIGS. 3B and 3C, a bone hole 252 is formed in bone 250, and filamentary sleeve 212 is inserted and anchored into bone hole 252. First free end 222 and loop 226 are passed through a first tissue penetration location 262, and second free end is passed through a second tissue penetration location 264. Thereafter, second free end 224 is advanced through loop 226 and tensioned. First free end 222 may also be tensioned simultaneously with the second free end 224 to help tension the structure and to help prohibit loop 226 and first free end 222 from being drawn through second penetration 262 during tensioning of second free end 264. As tension is applied, filament 220 compresses tissue 260 against bone 250.

Figure 3D:
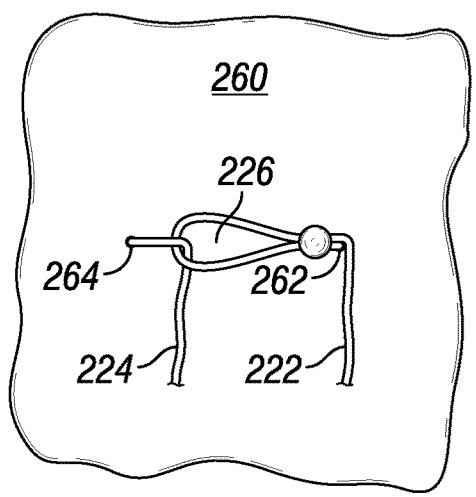
FIGS. 3D and 3E are schematic top views of the configuration of the tissue fixation assembly of FIG. 3A.
Figure 3E:
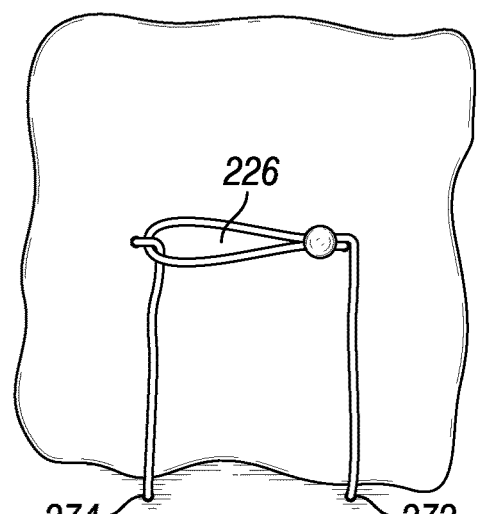

As shown in FIGS. 3D and 3E, tissue 260 may be a rotator cuff, and first and second penetrations 262, 264 may be aligned in an anterior/posterior direction. Second free end 224 extends from loop 226 at apex 228, first free end 222 extends from junction 227, and loop 226 extends along tissue 260 between first and second penetrations 262, 264. Thereafter, first and second free ends 222, 224 may be secured laterally to bone 250 via bone anchors 272 and 274, respectively. Bone anchors 272 and 274 may each be a filamentary anchor, such as sleeve 12, or a solid anchor as is known in the art. Alternatively, both the first and second free ends 222, 224 may be secured laterally to bone 250 via a single bone anchor (not shown). Therefore, as described, a surgical knot need not be applied.

Figure 4A:
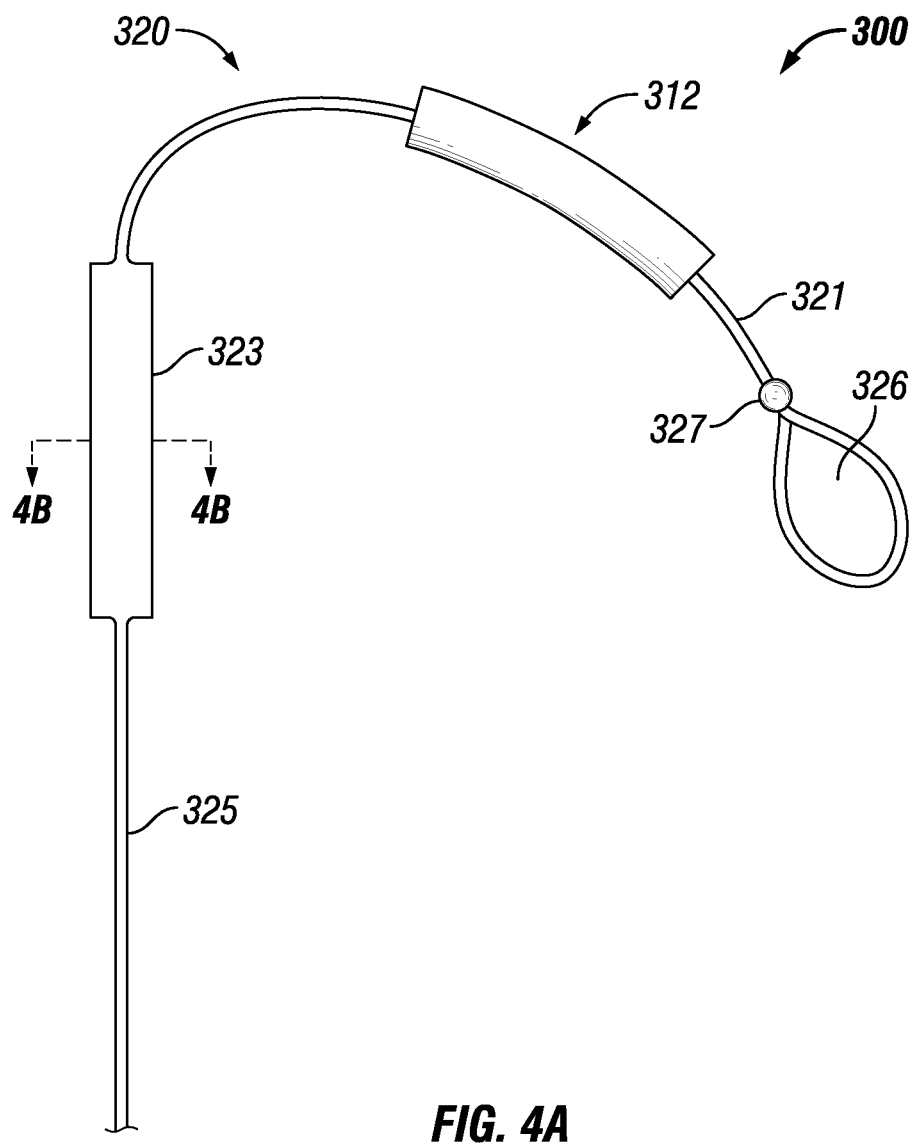
FIG. 4A illustrates yet another embodiment of a tissue fixation assembly.

FIG. 4A illustrates another fixation assembly embodiment, fixation assembly 300. Fixation assembly 300 includes a filamentary sleeve 312 and a length of filament 320. Filamentary sleeve 312 may be the same as sleeve 12.

Filament 320 includes a first end 321, a second end 325, and a tape portion 323 disposed between first and second ends 321, 325. First and second ends 321, 325 are joined to tape portion 323 either by being braided together as a single construct or are coupled by other means such as gluing, sewing, or welding together, for example. First end 321 of filament 320 includes a loop 326. Loop 326 may be formed as previously described, for example, by splicing filament 320 at junction 327 to form loop 326.

Figure 4B:
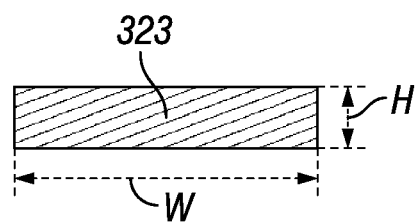
FIG. 4B is a cross-sectional schematic view of the tissue fixation assembly of FIG. 4A taken at 4B-4B.

Tape portion 323 has a generally flat cross-section that includes a height (h) and width (w), as shown in FIG. 4B. First and second ends 321, 325 preferably include a rounded cross-sectional profile having a diameter. Thus, as shown, filament 320 may have a round-flat-round configuration. The width of the tape portion 323 is preferably greater than the diameter of the first and second ends 321, 325, while the height of the tape portion 323 may be substantially equal to or less than the diameter of ends 321 and 325.

In one embodiment, filament 320 may have a round-flat configuration in which filament 320 would only be comprised of end 321 and flat portion 323. In such an embodiment, end 321 would form loop 326. In another embodiment, filament 320 may have a flat-round configuration in which filament 320 would only be comprised of flat portion 323 and end 325. In this embodiment, tape portion 323 would form loop 326. In a further embodiment, filament 320 may be flat along its entire length. In other words, in this example filament 320 may be comprised entirely of tape portion 323 with no rounded portions/ends. In yet another embodiment, first and second ends 322, 323 may have a rectangular cross-sectional profile in which the width of tape portion 323 may be greater than the width of the ends 321 and 325, and the height of the tape portion may be substantially equal to or less than the height of the tape portion. The flat profile and relatively large width of the tape portion may facilitate a broad compressive footprint and help reduce irritation of the tissue. Such filaments may have any configuration of round and/or flat portions as desired.

When assembled, sleeve 312 is preferably arranged about first end 321 such that first end 321 is at least partially disposed within the passageway of sleeve 312. In the embodiment shown in FIG. 4A, or other embodiments, such as a flat-round embodiment or entirely flat embodiment, sleeve 312 may be alternatively arranged about tape portion 323.

Figure 4C:
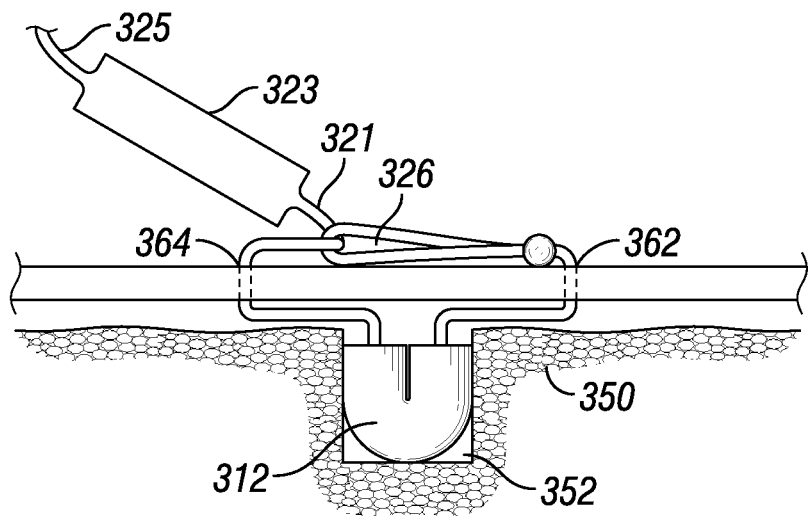
FIG. 4C is a schematic side view of a configuration of the tissue fixation assembly of FIG. 4B.
Figure 4D:
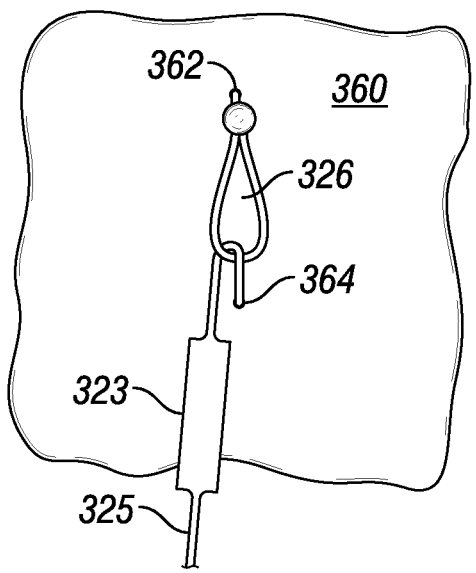
FIGS. 4D and 4E are schematic top views of the configuration of the tissue fixation assembly of FIG. 4A.
Figure 4E:
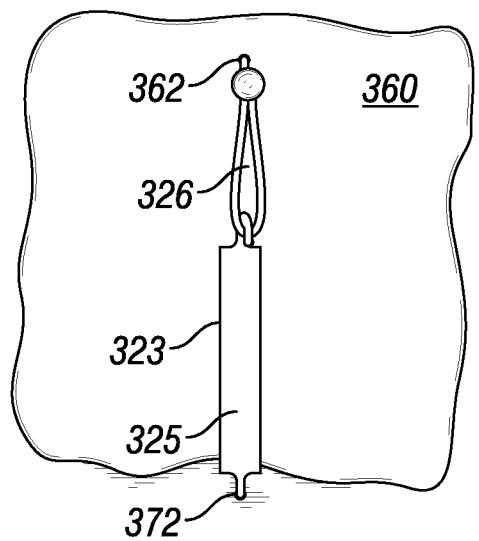

FIGS. 4C-4E depict an exemplary method of using fixation device 300. A bone hole 352 is formed in bone 350, and sleeve 312, which is slidably attached to first end 321, is inserted into bone hole 352, as shown in FIG. 4C. First and second ends 321, 325 are tensioned to seat sleeve 312 into an anchoring position. Loop 326 is at least partially passed through a first tissue penetration location 362, and second end 325 and tape portion 323 are passed through a second tissue penetration location 364. Second end 325 and tape portion 323 are advanced through the loop 326 such that loop 326 encompasses a portion of first end 321.

In an example of a rotator cuff, as illustrated in FIGS. 4D and 4E, second end 325 is tensioned and tape portion 323 is extended over tissue 360. Second end 325 is then attached to a bone anchor (filamentary or the like) and secured to bone 350. In this manner, tape portion 323 forms a broad compressive footprint to facilitate tissue adhesion to bone 350.

Figure 5A:
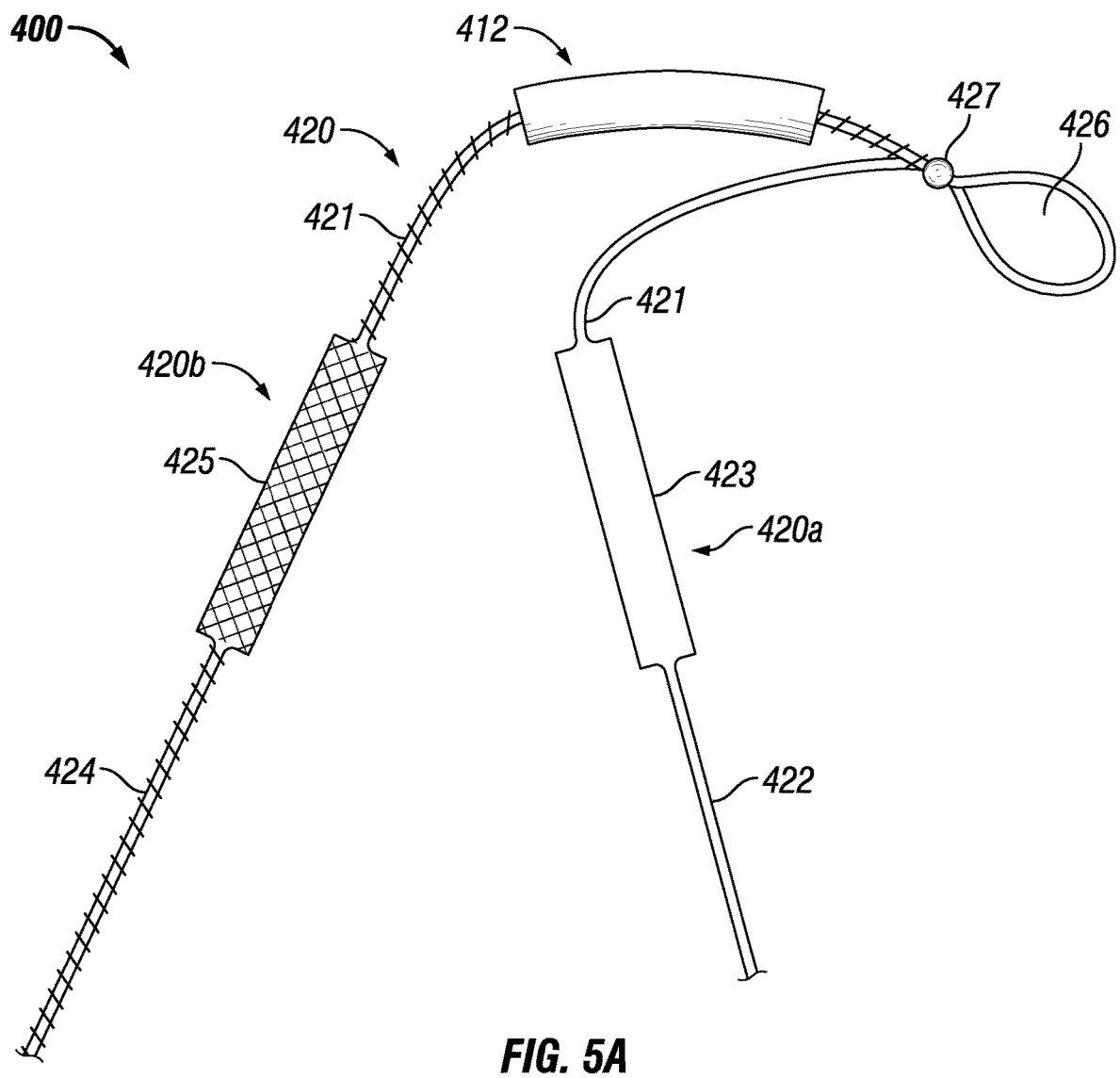
FIG. 5A illustrates still another embodiment of a tissue fixation assembly that includes a sleeve and a length of filament.

FIG. 5A depicts a further fixation assembly embodiment, fixation assembly 400. Fixation assembly 400 includes a filamentary sleeve 412 and a length of filament 420. Filamentary sleeve 412 may be the same as sleeve 12.

Figure 5B:
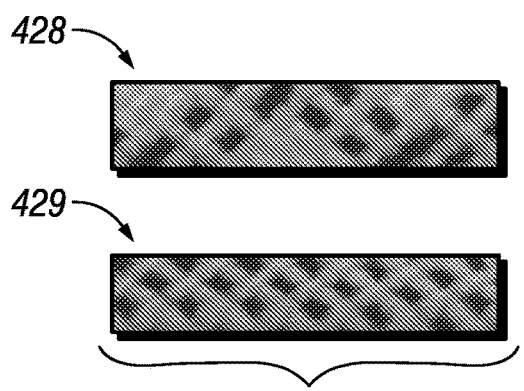
FIG. 5B illustrates exemplary braiding patterns of the length of filament of FIG. 5A.

Filament 420 is divided into a first segment 420*a* and a second segment 420*b* each having a distinctive braiding pattern. For example, first segment may have spiral braiding pattern 428, and second segment may have a speckled braiding pattern 429, as shown in FIG. 5B. However, it should be understood that filament 420 can have the same braiding pattern throughout, or a pattern along only one segment or along a portion of one or both segments, or the like.

The braiding pattern or patterns may be formed in any manner desired. For example, one or more fibers of a distinct color may be woven into the braid (as in FIG. 5B) to create a desired pattern along a portion, segment or the entirety of the filament. In another example, a surgical marker or pen may be used to mark a portion, segment or the entirety of the filament with a particular pattern, color or the like. For instance, a blue pen could be used to designate segment 420*a* while a red pen could be used to designate segment 420*b*. Such pattern or color differences can assist a surgeon in keeping track of the filament lengths during the surgical procedure.

Filament 420 includes a first end portion 422, a second end portion 424, an intermediate portion 421, a first tape portion 423, and a second tape portion 425. First tape portion 423 is disposed between first end 422 and intermediate portion 421, and the second tape portion 425 is disposed between the second end 424 and intermediate portion 421. A loop 426 is formed by intermediate portion 421, for example, by splicing filament 420 at a junction 427.

First segment 420*a* comprises loop 426, first end 422, first tape portion 423, and a length of intermediate portion 421 that extends from the junction 427 to the first tape portion 423. Second segment 420*b* comprises second end 424, second tape portion 425, and a length of intermediate portion 421 that extends from junction 427 to second tape portion 425.

Tape portions 423 and 425 are similar to tape portion 323. First end 422, second end 424, and intermediate portion 421 are similar to ends 321 and 325. Thus, filament 420 preferably has a round-flat-round-flat-round configuration. In other embodiments, filament 400 may have configurations as described with respect to filament 320. For example, filament 400 may have a round-flat-round, round-flat, flat-round, rectangular-flat-rectangular, entirely flat, or any other configuration as desired.

In addition, tape portions 423 and 425 may be joined to intermediate portion 421 and end portions 422 and 424 by being braided together as a single construct or coupled by other means such as gluing, sewing, or welding together, for example. First and second ends 422, 424 and intermediate portion 421 also have a corresponding height and width, or, alternatively, a diameter. The width of tape portions 423 and 425 are greater than the width/diameter of first and second ends 422, 424 and intermediate portion 421. When applied to tissue, tape portions 423 and 425 generally extend over soft tissue and compress the tissue against bone. The flat profile and relatively large width may facilitate a broad compressive footprint and may help reduce irritation of the tissue.

Sleeve 412 can be assembled with filament 420 in a similar fashion to fixation assembly 200, shown in FIG. 3A. For example, sleeve 412 may be positioned about a length of the intermediate portion 421 that extends between junction 427 and second tape portion 425, or, alternatively, between junction 427 and first tape portion 423. In some embodiments, depending on the configuration of filament 400, sleeve 412 may be positioned about tape portion 422 or 424.

Figure 5C:
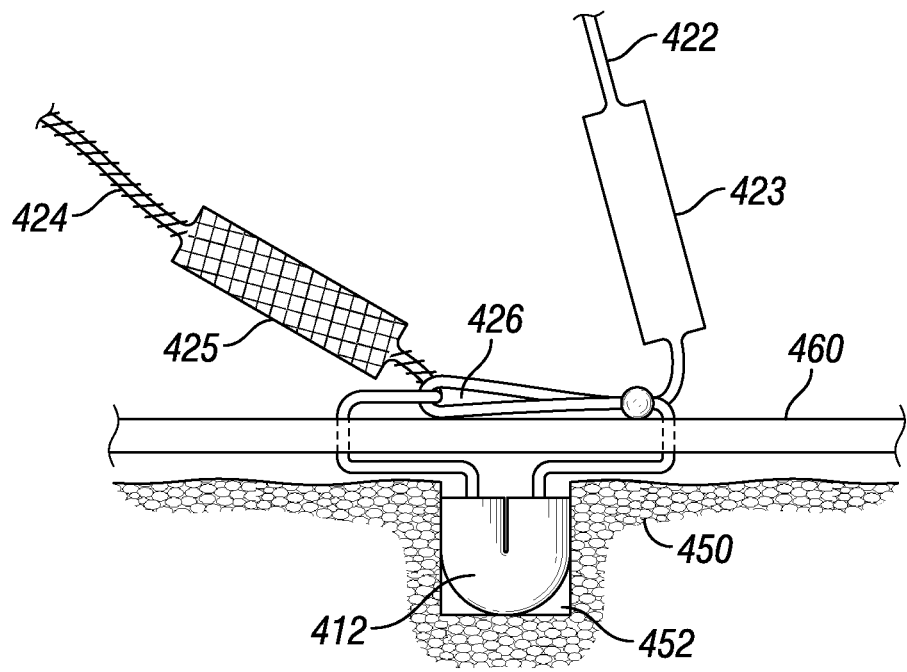
FIG. 5C is a schematic side view of a configuration of the tissue fixation assembly of FIG. 5A.
Figure 5D:
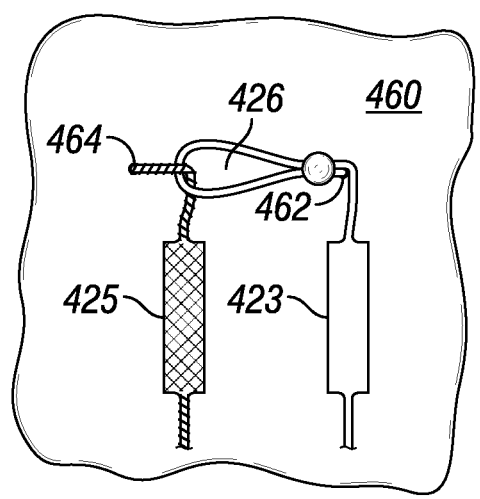
FIGS. 5D and 5E are schematic top views of a first arrangement of the tissue fixation assembly of FIG. 5A and configuration of FIG. 5C.
Figure 5E:
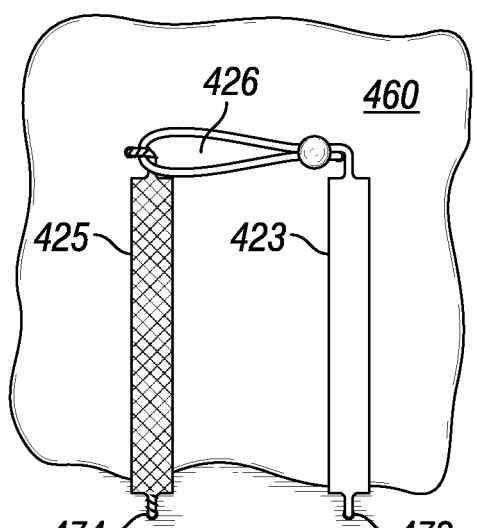

FIGS. 5C-5E depict one exemplary method of using fixation assembly 400, which is similar to the method of using fixation device 200, as shown in FIGS. 3B-3E. In this method, a bone hole 452 may be formed in bone 450 and sleeve 412 inserted into the bone hole 450, as shown in FIG. 5C. First end 422, first tape portion 423 and loop 426 are passed through a first tissue penetration location 462, and second end 424 and second tape portion 425 are passed through a second tissue penetration location 464. Second end 424 and second tape portion 425 are then passed through loop 426 and second end 424 and optionally first end 422 are tensioned.

In an example of a rotator cuff repair, such as a partial thickness tear, as illustrated in FIGS. 5D and 5E, first and second ends 422, 424 are tensioned in a medial/lateral direction. First end 422 and first tape portion 423 are advanced over tissue 460 and anchored to bone 450 with the bone anchor 472. Second end 424 and second tape portion 425 are also advanced over tissue 460 and anchored to bone 450 with bone anchor 474. In this manner, tape portions 423 and 425 may form a broad compressive footprint to facilitate tissue adhesion to bone 450. In an alternative embodiment, both first and second ends 422, 424 may be secured laterally to bone 450 via a single bone anchor (not shown).

Alternative configurations of filament 420 and sleeve 412 and methods of using same are envisioned. For example, filament 420 and sleeve 412 can be assembled and used in a similar fashion as fixation device 100, shown in FIG. 2A.

FIG. 6A depicts yet another fixation assembly embodiment 500. Fixation assembly 500 generally includes a first length of filament 520, a second length of filament 530 and three filamentary sleeves 512*a-c*. However, it should be understood that fixation assembly 500 can include any number of filamentary sleeves 512, such as one, two, three or four filamentary sleeves, for example. It should also be understood that any number of filaments may be utilized in fixation assembly 500, such as one, two, three, or four filaments, for example. Each of sleeves 512*a-c* may be the same as sleeve 12, described above. In addition, each length of filament 520, 530 may be the same as filament 20.

Continuing with the illustrated exemplary embodiment, once assembled, filaments 520 and 530 extend through each sleeve 512*a-c* such that first free ends 522 and 532 extend from third sleeve 512*c* and second free ends 524 and 534 extend from second sleeve 512*b*. In some embodiments, a single length of filament may be assembled with sleeves 512*a-c* in the same manner as filaments 20, 120, and 220 as shown in FIGS. 1A, 2A, and 3A.

Figure 6B:
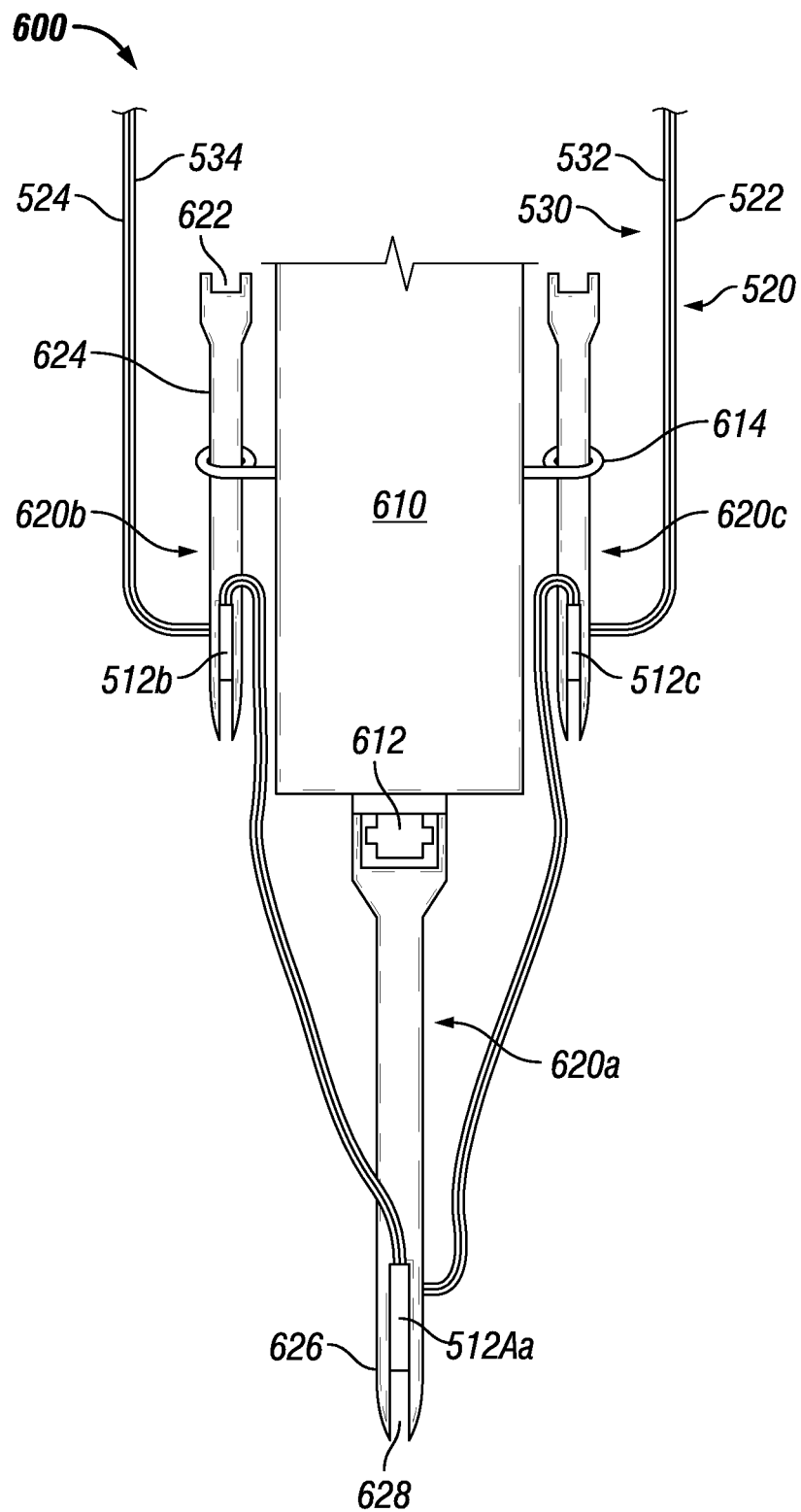
FIG. 6B illustrates one embodiment of an inserter device.

FIG. 6B depicts one embodiment of an inserter device 600, which can be implemented with fixation assembly 500. Inserter 600 generally includes a body 610, a head connector 612, retaining arms 614, and three removable heads 620*a-c*. However, it should be understood that any number of removable heads 620 may be utilized, which may largely depend on the number of sleeves 512 being implanted. For example, inserter device 600 may include one, two, three, or four removable heads 620.

Removable heads 620*a-c* each generally include a connector portion 622, an elongate shaft 624, and an insertion tip 626 having a retaining slot 628. Elongate shaft 624 may be sufficiently long to be implemented through an arthroscopic cannula. Each head 620 is capable of being attached and detached to the connector 612 via a quick-connect mechanism, which may include magnets, a ball detent, or the like. Insertion tip 626 may be sharpened to penetrate tissue and insert sleeve 512 into a preformed bone hole. In other embodiments, penetration end 626 may be sharpened to penetrate bone and tissue in the manner of a punch. Retaining slot 628 is configured to releasably hold sleeve 512 in a bent configuration while filaments 520 and 530 are slidably retained by each sleeve 512*a-c*. Optionally, an actuating arm or arms (not shown) can cover slot 628 during penetration of tissue and can be actuated so that it is moved out of the way during implantation of sleeve into bone. Retaining members 614 are attached to body 610 and configured to hold any of the removable heads 620*a-c*.

Inserter 600 and fixation assembly 500 may be preassembled, packaged, and delivered to the operating theater. Alternatively, inserter 600 and fixation assembly 500 may be packaged and delivered unassembled to the operating theater where assembly takes place. When assembled for use, first removable head 620*a* is attached to connector 612 and second and third removable heads 620*b*, 620*c* are retained by retaining members 614. Each head 620*a-c* includes a respective sleeve 512 located in respective slots 628 and each filament 520, 530 is disposed within each sleeve 512*a-c* such that first free ends 522 and 532 and second free ends 524 and 534 extend from removable heads 620*c* and 620*b*, respectively. Filaments 520 and 530 are slidable within sleeves 512*a-c* so that they may be tensioned during implantation of sleeves 512*a-c* as needed.

Figure 6C:
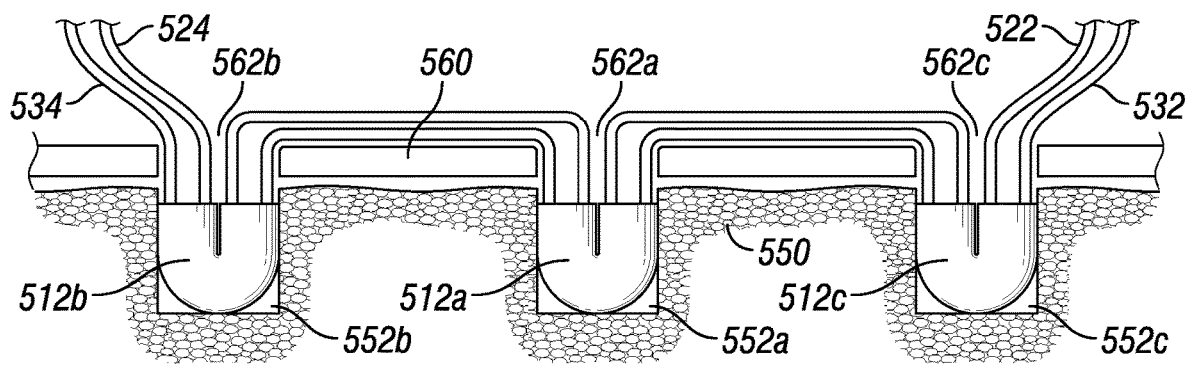
FIG. 6C is a schematic side view of an exemplary configuration of the tissue fixation assembly of FIG. 6A employing inserter device of FIG. 6B.
Figure 6D:
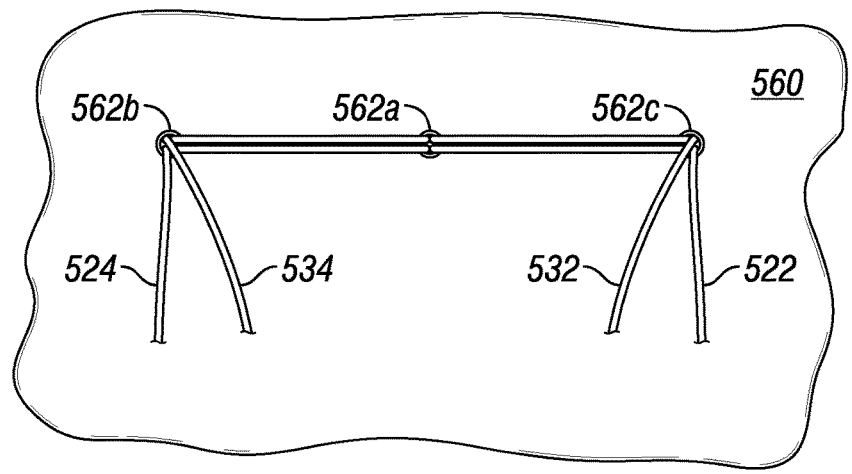
FIGS. 6D and 6E are schematic top views of the configuration of the tissue fixation assembly of FIGS. 6A and 6C.
Figure 6E:
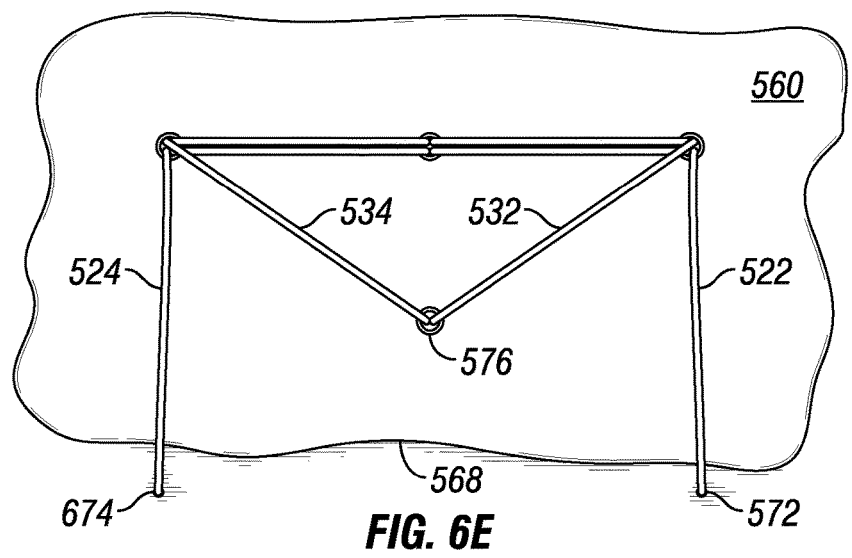

FIGS. 6C-6E depict one exemplary embodiment of a method of using inserter device 600 and fixation assembly 500. In this method, each sleeve 512*a-c* is generally inserted through tissue 560 and implanted into bone 550. However, it is envisioned that each sleeve 512*a-c* may be implanted into bone 550 and then a single length of filament having a loop may be passed through tissue 560 in a similar manner as that described with respect to FIGS. 1A-5E.

Prior to implantation, three bone holes 552*a-c*, one for each sleeve 512*a-c*, may be formed in bone 550 at desired locations. For example, in a rotator cuff reparation procedure, bone holes 552*a-c* may be formed in a medial row generally aligned in an anterior/posterior direction. Tissue 560 may then be tensioned and first head 620*a* containing first sleeve 512*a* is inserted through tissue 560 at first tissue penetration location 562*a*. Thereafter, insertion tip 626 and sleeve 512*a* are inserted into the first bone hole 552*a*, sleeve 512*a* is released therein, and head 620*a* is removed from the bone hole 552*a*. Filaments 520 and 530, which extend from first bone hole 552*a*, first penetration 562*a*, and through sleeves 512*b* and 512*c*, are tensioned to fully seat sleeve 512*a*.

Thereafter, first head 620*a* is detached from connector 612 and second head 620*b* retaining second sleeve 512*b* is attached to connector 612. Second head 620*b* is then inserted through tissue 560 at a second tissue penetration location 562*b*. Second sleeve 512*b* is inserted into second bone hole 552*b* and released therein. Second head 620*b* is removed from second bone hole 552*b* and second free ends 524 and 534 along with a portion of filaments 520 and 530 that extend between the first and second sleeves 512*a*, 512*b* are tensioned to fully seat sleeve 512*b*.

Thereafter, second head 620*b* is detached from connector 612 and third head 620*c* retaining third sleeve 512*c* is attached to connector 612. Third head 620*c* is then inserted through tissue 560 at a third tissue penetration location 562*c*. Third sleeve 512*c* is inserted into third bone hole 552*c* and released therein. Third head 620*c* is removed from third bone hole 552*c* and first free ends 522 and 532 along with a portion of filaments 520 and 530 that extend between the first and third sleeves 512*a*, 512*c* are tensioned to fully seat third sleeve 512*c*.

The operator retains control of first free ends 522 and 532 and second free ends 524 and 534. As illustrated in FIGS. 6D and 6E, these ends are then tensioned which cinches down the portions of filaments 520 and 530 that extend between each sleeve 512*a-c*. As this occurs, tissue 560 underlying these portions of filaments 520 and 530 is compressed against the underlying bone. The free ends 522, 524, 532, 534 are available to be attached to one or more bone anchors, filamentary or the like. For example, in a rotator cuff repair and as shown in FIG. 6E, first free end 522 and second free end 524 may be anchored via anchors 572 and 574, respectively, to the humerus beyond the lateral edge 568 of the tissue 560. Additionally, first free end 532 and second free end 534 may be anchored to the humerus through tissue 560 via anchor 576, as shown. While FIGS. 6D and 6E illustrate one example, other configurations may be formed dependent on the type of soft tissue, type of repair, number of filaments, and number of bone anchors.

Figure 7:
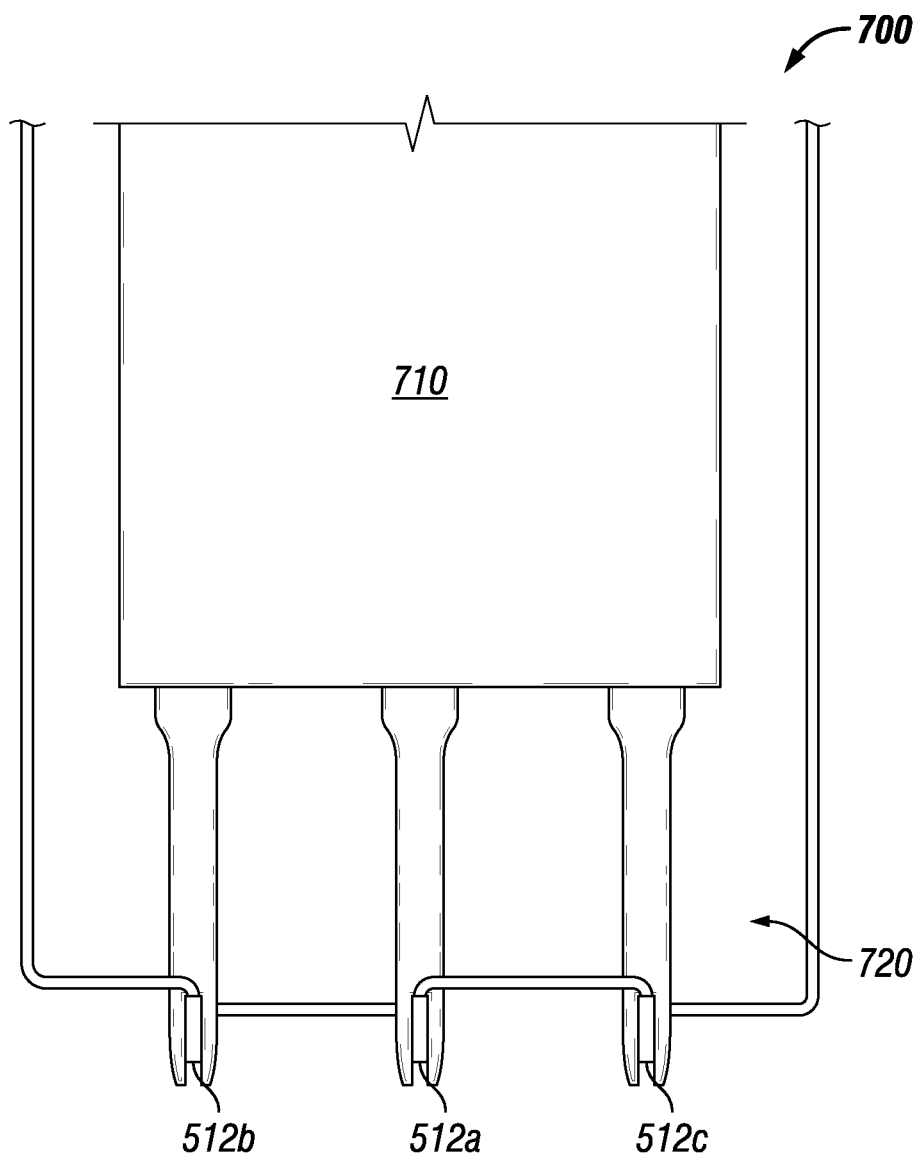
FIG. 7 illustrates an alternative embodiment inserter device.

FIG. 7 depicts an alternative inserter device 700, which may be utilized in conjunction with fixation assembly 500. Inserter device 700 is similar to inserter device 600 in that it includes a body 710 and a plurality of heads 720. In addition, each head 720 releasably retains a filamentary sleeve 512 while at least one filament extends through each sleeve. However, unlike inserter 600, each head 720 is attached to body 710 in a configuration for substantially simultaneous insertion of sleeves 512*a-c*. Thus, during operation, each head 512*a-c* concurrently punctures through tissue 560 and is advanced into their respective bone holes where sleeves 512*a-c* are deposited and anchored. It is envisioned that the body 710 could be adjusted, or otherwise, to adjust the spacing of the heads 720.

FIGS. 8A-8D depicts another inserter device embodiment 800. Inserter 800 generally includes an intermediate shaft 802, a first insertion end 810 disposed at one end of intermediate shaft 802, and a second insertion end 820 disposed at another end of intermediate shaft 802. Inserter 800 can be made of any biocompatible material, such as stainless steel or titanium.

Intermediate shaft 802 is elongate and may include a connection feature, such as through-hole 804, at a location along its length. Through-hole 804 may be dimensioned to receive a retaining mechanism, such as a retaining pin, for retaining externally connected devices, such as a suture cleat 840 (depicted in FIG. 10A), to intermediate shaft 802. Other retaining mechanisms and connecting features are also envisioned.

As illustrated in FIGS. 8C and 8D, first insertion end 810 generally includes an insertion shaft 816 and prongs 812 disposed at a terminal end of insertion shaft 816. Prongs 812 each have a penetrating tip 811, which may be sufficiently sharp to penetrate or pierce soft tissue. Penetrating tip 811 may also be sufficiently sharp and prongs 812 sufficiently rigid to penetrate cortical and/or cancellous bone. As shown, prongs 812 taper in at least two planes, which may provide rigidity and facilitate ease of penetration. However, it should be understood that the other tip configurations are envisioned. For example, prongs 812 may each have a dull tip, which can be used when a preformed hole in bone is provided. Alternatively, the tip may include a single prong or have a different feature for engaging or manipulating tissue.

Continuing with this embodiment, prongs 812 also define a recess 814 therebetween. Recess 814 defines a crotch 813 and is dimensioned to receive and retain a first anchor (not shown), such as a filamentary sleeve anchor 12. More particularly, recess 813 is dimensioned such that the first anchor can be placed in recess 814 and bent over crotch 813 so that the first anchor sits below penetrating tips 811. Another example of a filamentary sleeve anchor can include the Iconix® all-suture suture anchor system (Stryker Corporation, Kalamazoo, Mich.). Other examples of filamentary sleeve anchors that may be used in conjunction with inserter 800 are described in the heretofore referenced applications and patents incorporated by reference herein.

Insertion shaft 816 is dimensioned to fit within a bone hole of predetermined size. In addition, insertion shaft 816 has a length corresponding to a desired depth of the bone hole. Insertion shaft 816 has two indented surfaces 818 disposed on opposite sides thereof. Such indented surfaces 818 intersect recess 814. This allows for a filamentary sleeve anchor 12 to be folded over crotch 813 and for opposing ends of the sleeve anchor to extend along indented surfaces 818. Indented surfaces 818 help provide clearance space for the sleeve anchor so that, for example, when the sleeve anchor is coupled to first insertion end 810, first insertion end 810 and the anchor sleeve together have a more narrow width than without indented surfaces 818. Thus, together these can fit within a more narrow bone hole. In other words, indented surfaces 818 provide for a smaller profile of the inserter and anchor thereby allowing for a smaller bone hole. Indented surfaces 818 may be planar or may be concavely grooved, which may provide rigidity to insertion shaft 816 at this location.

A shoulder/collar 806 is disposed between intermediate shaft 802 and insertion shaft 816. Shoulder/collar 806 can generally include an abutment surface 807, a transverse through-hole 808 and longitudinally extending slots 809. Shoulder/collar 806 has a maximum cross-sectional dimension larger than a cross-sectional dimension of insertion shaft 816. As such, abutment surface 807 serves as a depth stop indicating to an operator when the appropriate insertion depth of insertion end 810 has been reached. Also, abutment surface 807 acts as an impact surface for a removable cap, as described in more detail below.

Transverse through-hole 808, if present, extends through the shoulder/collar 806 and is dimensioned to receive at least one filament therein. However, through-hole 808 can accommodate more than one filament. Longitudinally extending notches 809, if present, intersect transverse through-hole 808. Such notches 809 are formed to provide a gap for one or more filaments when a removable cap is connected to first insertion end 810, as described further below.

Second insertion end 820 is identical to first insertion end 810. In addition, a second shoulder/collar is disposed between intermediate shaft 802 and second insertion shaft 816 and is identical to first shoulder/collar 806 described above. Although, second insertion end 820 is preferably identical to first insertion end 810, it is contemplated that other embodiments of inserter 800 may include a second insertion end adapted for other anchor types. For example, first insertion end 810 may be configured to retain a filamentary sleeve anchor as described above, and second insertion end 820 may be configured to retain a hard anchor, in a manner known in the art. Even further, first and second insertion ends 810, 820 may each be configured to retain a hard anchor.

Figure 9:
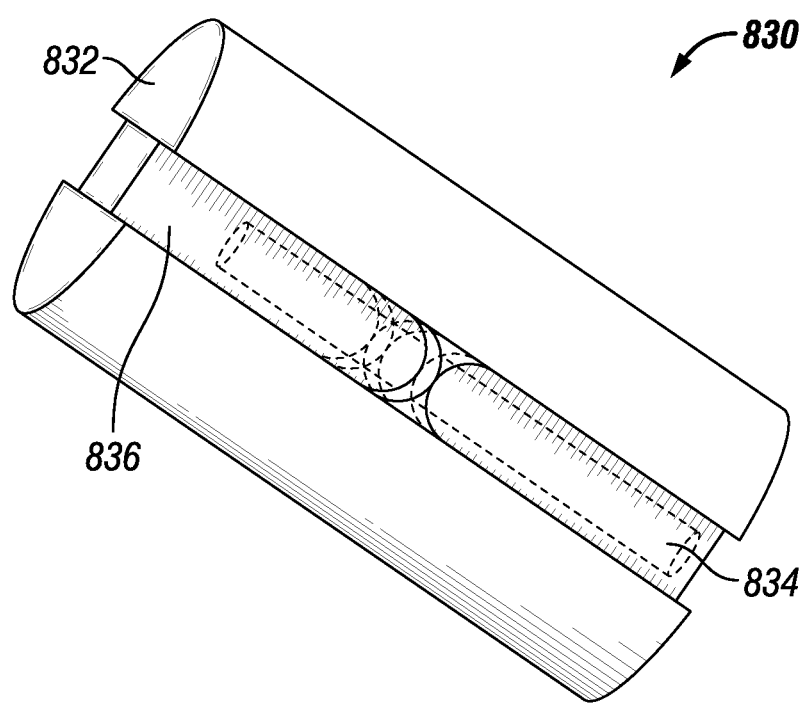
FIG. 9 is a perspective view of one embodiment of a cap.

FIG. 9 depicts one embodiment of a cap 830, which may be used in conjunction with inserter 800. Cap 830 is generally cylindrical and includes a planar impact surface 832 and a planar abutment surface 838 (see FIG. 10C) disposed at opposite ends of cap 830. A bore 834 extends through abutment surface 838 and into cap 830. As shown, bore 834 is a blind bore and, therefore, does not extend all the way through cap 830. However, in some embodiments, bore 834 can extend through the entirety of cap 830. Bore 834 is dimensioned to be longer than first and second insertion ends 810, 820. Bore 834 is also dimensioned to receive each of insertion ends 810, 820 therein, even when their respective bone anchors are retained thereon. Cap 830 may also include longitudinally extending grooves 836, which can be used as filamentary pathways to facilitate suture/filament management.

Figure 10A:
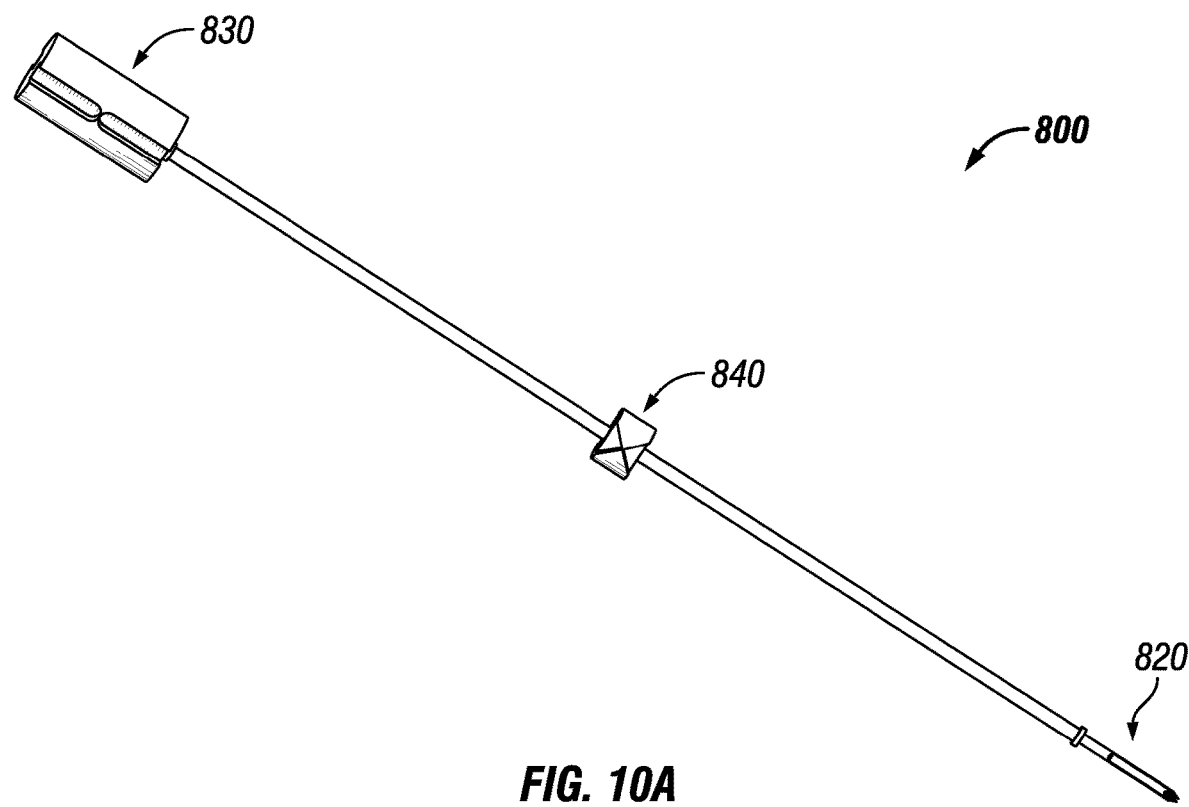
FIG. 10A is a perspective view of an assembly including the inserter of FIG. 8A and cap of FIG. 9.
Figure 10B:
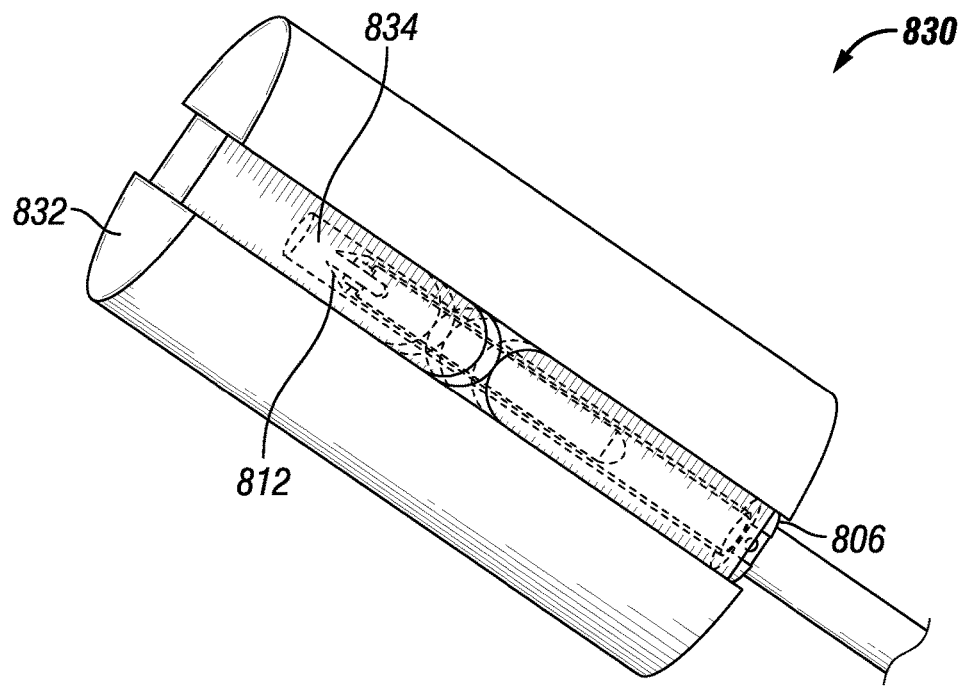
FIG. 10B is an enlarged side perspective view of the assembly of FIG. 10A.
Figure 10C:
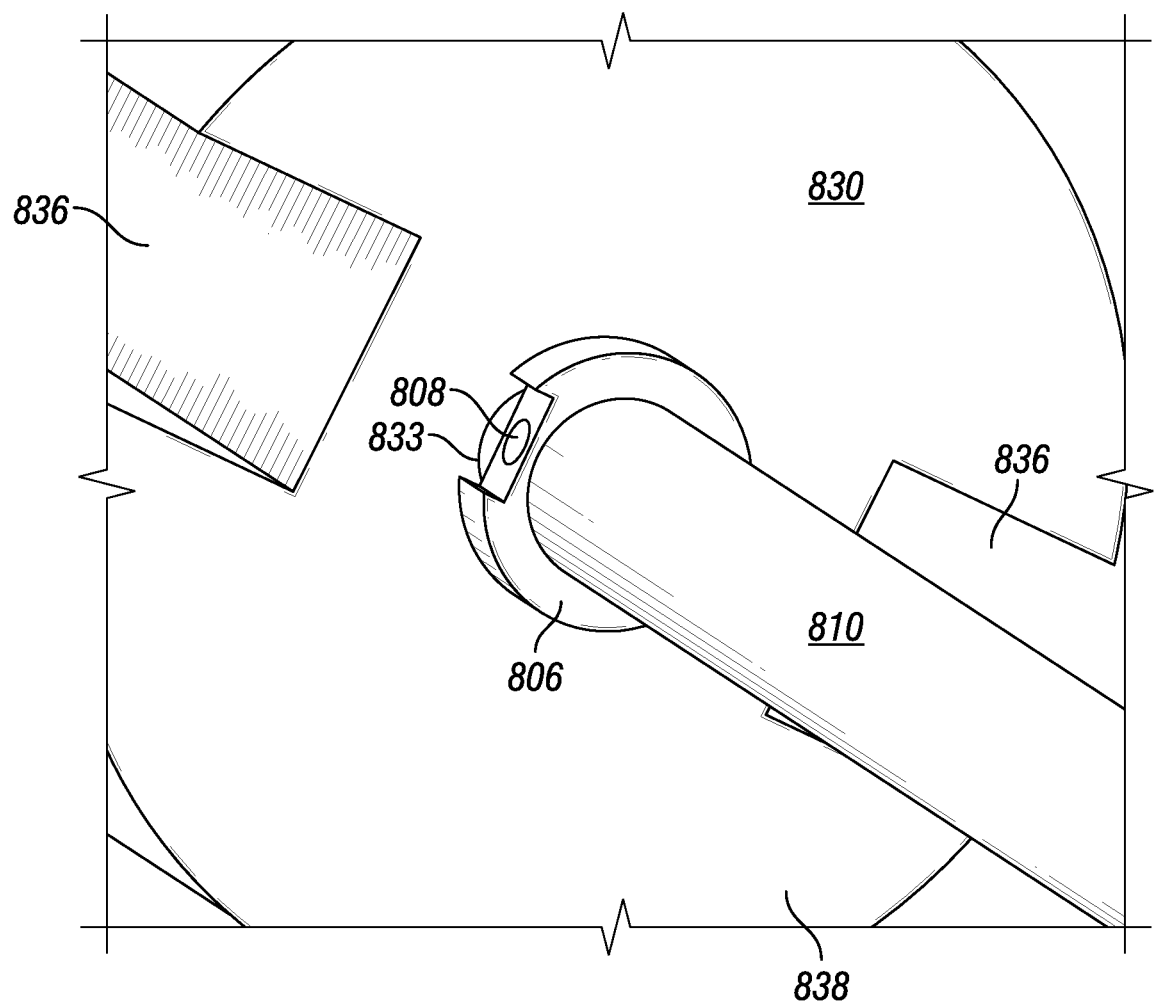
FIG. 10C is an enlarged bottom perspective view of the assembly of FIG. 10A.

FIGS. 10A-10C depict cap 830 assembled to the inserter 800 in an exemplary embodiment. In the assembly, first insertion end 810 extends into bore 834 and abutment surface 838 of cap 830 abuts abutment surface 807 of shoulder/collar 806. Such abutment surfaces 807, 838 may lie flush against each other to facilitate uniform impact distribution. Although insertion end 810 is depicted without a bone anchor, as mentioned above, cap 830 is capable of fitting over first insertion end 810 with a first bone anchor attached thereto.

Also, as best shown in FIG. 10B, when first insertion end 810 is disposed within bore 834, a space may exist between prongs 812 and an end of bore 834. This prevents prongs 812 from being damaged during impaction, as discussed further below.

Moreover, as best shown in FIG. 10C, when the respective abutment surfaces 807, 838 contact each other, a gap 833 may be formed by the longitudinally extending notches thereby exposing bore 834. Such gap 833 is sized to allow for one or more filaments to extend therethrough.

In one embodiment of a method of using inserter 800 and cap 830, inserter 800 may be provided preassembled with first and second filamentary bone anchors (not shown). In such a preassembled configuration, the first anchor may be disposed within recess 814 and bent over crotch 813 such that a first and second ends of the filamentary anchors extends along respective indented surfaces 818. The second bone anchor may be similarly situated on second insertion end 820. One or more filaments preferably connects to the first and second anchors such that the anchors are coupled to each other by the one or more filaments and such that a first end of the one or more filaments extends from the first anchor and a second end extends from the second anchor. Such anchor and filament arrangement may be similar to that shown in FIG. 6B. In addition, the one or more filaments can include one or more tape portions, such as with filaments 320 and 420 described above. Also, the one or more filaments can form adjustable or fixed loops, such that in assemblies 10, 100, 200, 300 and 400.

First insertion end 810 along with the first anchor are passed through an arthroscopic cannula (or incised tissue in open surgery). Penetrating tips 811 may then pierce through soft tissue, such as a rotator cuff, and be placed adjacent to bone (e.g., in a PASTA repair). When the desired location for anchor placement is determined, the operator impacts impact surface 832 of cap 830, which is extracorporeally located and disposed over second insertion end 820 and the second bone anchor. The force of the impacts is transferred from cap 830 to inserter 800 via the shoulder/collar 806. The operator continues to impact cap 830 until abutment surface 807 of shoulder/collar 806 contacts the bone and provides resistance to the operator indicating that the appropriate depth has been reached. In one embodiment, impaction of cap 830 penetrates bone without the use of a preformed hole. As such, penetrating tips 811 and the two-plane taper of penetrating tips 811 helps facilitate penetration. In an alternative embodiment, a preformed hole is provided, and impaction helps advance first insertion end 810 and the first bone anchor into the preformed hole. In the variation where the inserter is a self-tapping inserter, the crotch and recesses 814 and indented surfaces 818 may protect the implant from damage from contact with the bone.

With first insertion end 810 and the first anchor fully inserted into a bone hole, the operator removes first insertion end 810 from the bone hole. The tight fit and friction of the bone helps the first anchor slide through recess 814 and remain in the bone as first insertion end 810 is removed. The one or more filaments extending from the anchor are tensioned to expand and fully seat the first filamentary sleeve anchor. Slack in the one or more filaments may be provided as needed.

First insertion end 810 is removed from the patient via the arthroscopic cannula. Cap 830 is removed from second insertion end 820 and the second bone anchor and placed over first insertion end 810. Second insertion end 820 and the second bone anchor are passed through the arthroscopic cannula. Soft tissue is penetrated by second insertion end 820, and impact surface 832 of the cap 830 is impacted in the same manner as when implanting the first anchor. Once second insertion end 820 and the second bone anchor are fully inserted into bone, second insertion end 820 is removed while the second bone anchor remains within the bone hole. The one or more filaments are tensioned to fully seat the anchor. The resulting anchor and filament arrangement may be similar to that shown in FIGS. 6C and 6D, with the exception that the tissue is anchored by two anchors rather than three.

Although inserter 800 is described in conjunction with cap 830 for its use, it should be understood that in some embodiments, inserter 800 may be used without a cap. For example, prongs 812 may have a dull flat surface and be used to insert filamentary sleeves in preformed bone holes. A mallet may be used to strike the end of such prongs to assist in inserting the anchors into the bone holes.

Inserter 800 provides significant benefits, which includes a construction that allows for preassembly of two bone anchors with filaments. This facilitates quick implantation of the bone anchors and ease of use, particularly by reducing suture management responsibilities of the operator.

Although it has been described that the first and second insertion ends penetrate soft tissue prior to impaction into bone, it should be understood that inserter 800 can be used to implant anchors and filaments under tissue without penetrating such tissue.

In still other embodiments, insertion devices such as those discussed above can be used with alternative suture and/or suture anchor structures. Such alternative structures, some of which are described above, may be useful in certain surgical methods and techniques.

FIGS. 11A-14 depict an inserter assembly 1010 according to another embodiment of the present disclosure. Inserter assembly 1010 generally includes a handle 1020, first inserter 1030, second inserter 1050, cap 1040, and sleeve 1060.

Figure 12A:
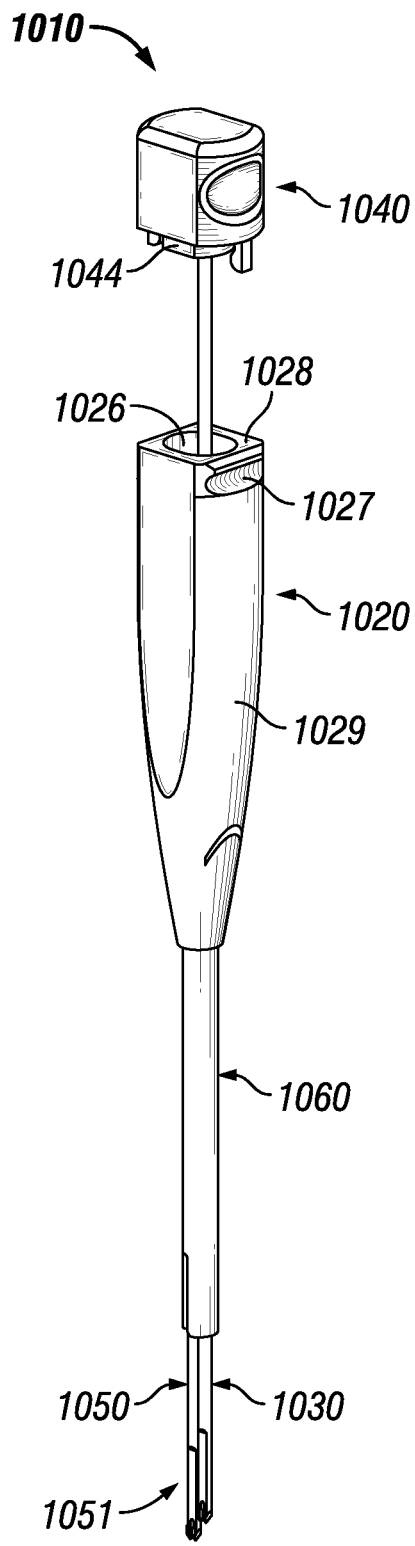
FIG. 12A is a perspective view of the inserter assembly of FIG. 11A being depicted in one stage of a transition phase thereof.

The handle 1020 includes a handle body 1029 which defines a passageway that extends entirely through the body 1029 in a proximal-distal direction. The cross-sectional dimension of the passageway generally increases in the distal direction which forms at least two distally facing surfaces 1021 and 1023, as best shown in FIG. 12C. A longitudinal slot 1025 extending through a proximal end of the handle body 1029 intersects the passageway along a portion of the length of the handle body 1029, as best shown in FIG. 13B, so as to receive a pin 1036 that extends from the first inserter 1030. An engagement feature 1024 is disposed within the handle 1020 adjacent the passageway so as to interface with the sleeve 1060 when disposed in the passageway (see FIG. 12C). As shown in the depicted embodiment, the engagement feature 1024 is a ball assembly of a ball-detent mechanism. However, the engagement feature 1024 can be a user actuated pin or some other feature known in the art for selectively retaining a moving component.

The handle body 1029 also defines exterior features. For example, one or more suture cleats 1022 (see FIG. 12B) are disposed on an outer surface between the proximal and distal ends of the handle body 1029. These cleats 1022 are configured to temporarily retain a suture/filament which may pass through bone anchors mounted to the inserters 1030, 1050, as described below. The handle body 1029 also includes a proximal impact surface 1028 which may be impacted when the cap 1040 is not connected to handle body 1029. A socket 1026 may extend distally into the impact surface 1028 and may have a non-circular geometry to match a distal projection 1044 of the cap 1040 while prohibiting the cap 1040 from rotating therein, as shown in FIG. 12A. The handle body 1029 also includes grooves 1027 at the proximal end that can be engaged by the cap 1040, such as by engagement members 1042, to temporarily lock the cap 1040 to the handle body 1029. Wings (not shown) may extend from the sides of handle body 1029 to provide further grip to the user and to provide additional cleats or filament retaining structures.

The first inserter or removable inserter 1030 is defined by an elongate shaft. An insertion end 1031 is located at a distal end of the elongate shaft, as best shown in FIGS. 11B and 11C. The insertion end 1031 includes prongs or penetrating tips 1032 that are separated by a recess 1034. The penetrating tips 1032 are sufficiently sharp to penetrate or pierce soft tissue. Penetrating tips 1032 may also be sufficiently sharp and sufficiently rigid to penetrate cortical and/or cancellous bone. As shown, tips 1032 taper in at least two planes, which may provide rigidity and facilitate ease of penetration. However, it should be understood that other tip configurations are envisioned. For example, tips 1032 may each have a dull end, which can be used when a preformed hole in bone is provided. Alternatively, the insertion end 1031 may include a single penetrating tip or have a different feature for engaging or manipulating tissue.

Recess 1034 defines a crotch 1037 and is dimensioned to receive and retain a first anchor, such as filamentary sleeve anchor 12. More particularly, recess 1034 is dimensioned such that the first anchor can be placed in recess 1034 and bent over the crotch 1037 so that the first anchor sits proximal relative to penetrating tips 1034. Another example of a filamentary sleeve anchor can include the Iconix® all-suture suture anchor system (Stryker Corporation, Kalamazoo, Mich.). Other examples of filamentary sleeve anchors that may be used in conjunction with inserter 1030 are described in the heretofore referenced applications and patents incorporated by reference herein. Also, it should be understood that while insertion end 1031 is particularly configured to retain a soft, filamentary anchor, it is contemplated that the insertion end may be configured to retain a hard anchor as known in the art.

Insertion end 1031 also has two indented surfaces 1033 disposed on opposite sides thereof. Such indented surfaces intersect recess 1037. This allows for a filamentary sleeve anchor to be folded over crotch 1037 and for opposing ends of the sleeve anchor to extend along indented surfaces 1033. Indented surfaces 1033 help provide clearance space for the sleeve anchor so that, for example, when the sleeve anchor is coupled to first insertion end 1031, first insertion 1031 end and the anchor sleeve together have a narrower width than without indented surfaces 1033. Thus, together these can fit within a narrower bone hole. In other words, indented surfaces 1033 provide for a smaller profile of the inserter 1030 and anchor thereby allowing for a smaller bone hole. Indented surfaces 1033 may be planar or may be concavely grooved, which may provide rigidity to inserter 1030 at this location.

The cap 1040 is secured to the proximal end of inserter 1030. The cap 1040 may include a distal projection 1044 configured to be received by the socket 1026 of handle body 1029. In addition, cap 1040 includes one or more engagement members 1042 that can engage handle body 1029 to temporarily secure cap 1040 to the handle body 1029. In the depicted embodiment such engagement members 1042 are in the form of flexible fingers that project distally and are capable of snapping into grooves 1027.

A coupling pin 1036 extends from the first inserter 1030 in a direction transverse to a longitudinal axis of inserter 1030. Pin 1036 is disposed between cap 1040 and insertion end 1031 and is located closer to cap 1040 than the insertion end 1031. Coupling pin 1036 helps prevent inserter 1030 from rotating when disposed within handle body 1029 and also helps secure inserter 1030 to sleeve 1060, as described below.

The second inserter or fixed inserter 1050 is similar to first inserter 1030 in that it is defined by an elongate shaft with a distal insertion end 1051 that is configured to retain a filamentary sleeve anchor, such as anchor 12. However, second inserter 1050 differs from first inserter 1030 in that second inserter 1050 has a shorter length than first inserter 1030. In addition second inserter 1050 does not include a coupling pin or cap.

Figure 12B:
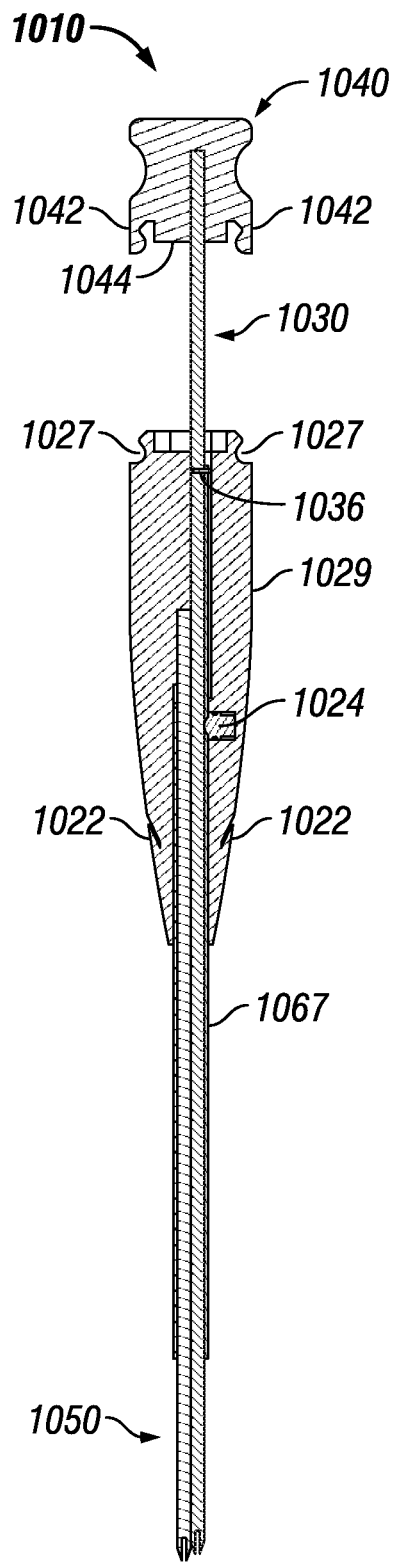
FIG. 12B is a cross-sectional view taken of the inserter of FIG. 12A taken along a midline thereof.
Figure 12C:
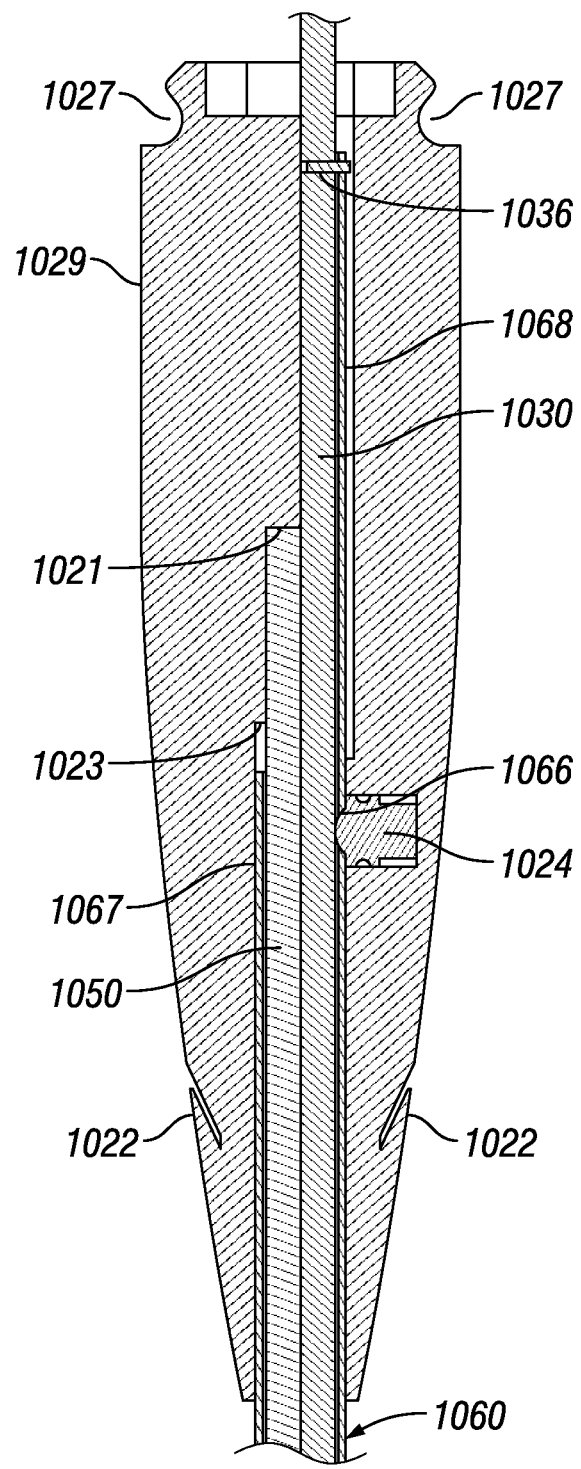
FIG. 12C is an enhanced view of FIG. 12B.

The sleeve 1060 defines a passageway extending therethrough in the proximal-distal direction and is sized to receive first and second inserters 1030, 1050, as best shown in FIGS. 12A and 12B. Sleeve 1060 includes a cylindrical portion 1067 and semicylindrical portion 1068 projecting proximally from the cylindrical portion 1067 (best shown in FIG. 12C). However, such portions 1067, 1068 may have other shapes, such as ovular or rectangular geometries, than cylindrical geometries. Such configuration helps sleeve 1060 conform to the change in cross-sectional dimension of the passageway of the handle body 1029. A transverse opening 1064 extends through opposite sides of the sleeve 1060 at the distal end thereof. This opening 1064 generally aligns with the insertion end 1051 of the second inserter 1050 when the second inserter 1050 is disposed within the sleeve 1060 and helps provide relief for a bone anchor connected to second insertion end 1051. In addition, when an anchor is mounted to second insertion end 1051, a filament may extend through the anchor. Transverse opening 1064 provides a passageway through which such filament can extend. In this regard, the filament would extend through transverse opening 1064 at both sides of sleeve 1060 and extend along the length of sleeve 1060 toward handle 1020. However, it should be noted that in some embodiments the filament can extend through sleeve 1060 rather than outside of sleeve 1060.

A notch 1069 extends into the proximal end of the sleeve 1060. Notch 1069, as shown in FIG. 11E, is key-hole shaped and is sized to receive the coupling pin 1036 in an interference fit manner so that the pin and slot connection releasably connects sleeve 1060 to inserter 1030. In this regard, the interference fit provides a secure connection between first inserter 1030 and sleeve 1060, but when sufficient force is provided, pin 1036 can be released from notch 1069 in a proximal direction thereby disconnecting sleeve 1060 from first inserter 1030.

When assembled, the inserter assembly 1010 generally has a first insertion configuration and a second insertion configuration. Assembly 1010 goes through a transition phase which is characterized by multiple stages when transitioning between the first and second configurations, as is described below.

Figure 11A:
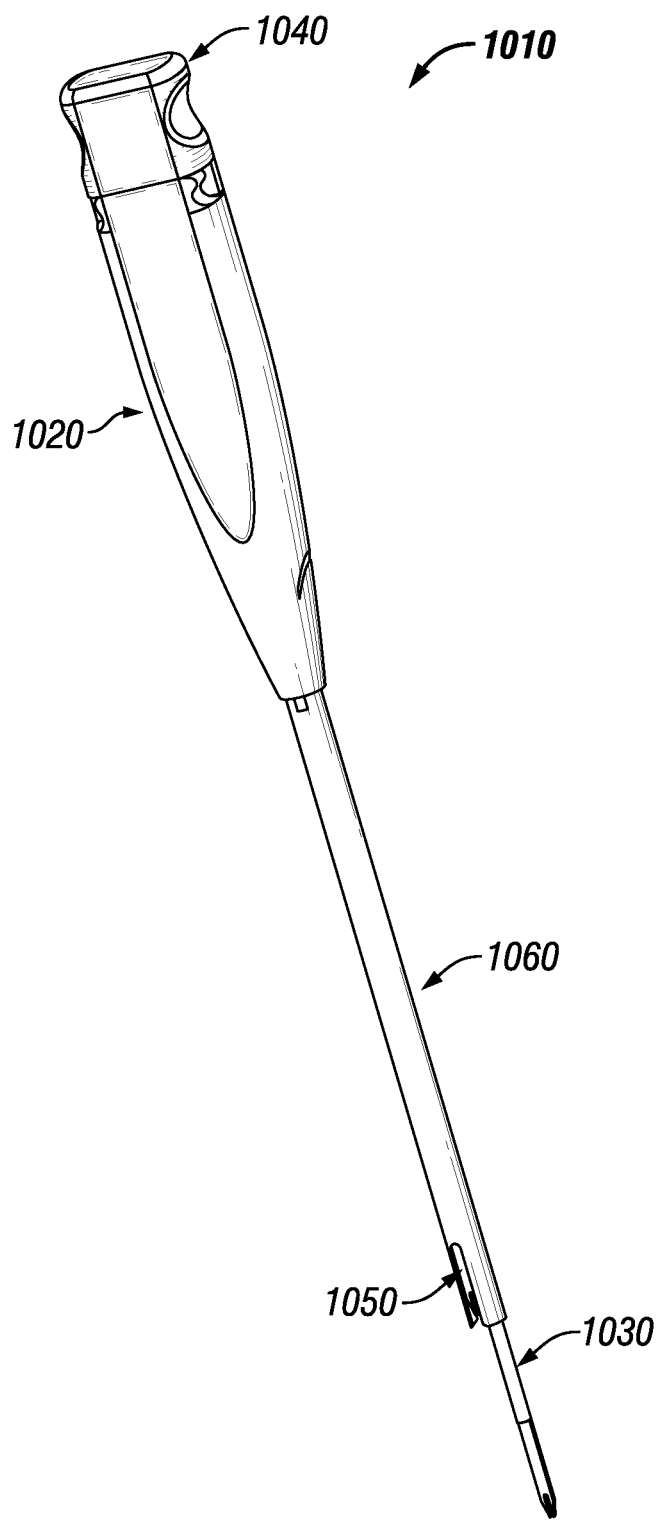
FIG. 11A is a perspective view of an inserter assembly according to another embodiment of the present disclosure being depicted in a first insertion configuration.

In the first insertion configuration, as depicted in FIGS. 11A-11E, assembly 1010 is configured to implant a first anchor which is mounted to the first insertion end 1031 of first inserter 1030. In this regard, sleeve 1060 is slidably disposed within the passageway of handle body 1029, and first and second inserters 1030, 1050 extend through the passageway of handle body 1029 and also through the passageway of sleeve 1060 so that sleeve 1060 surrounds respective portions of inserters 1030 and 1050. First inserter 1030 is connected to cap 1040 which is removably connected to the proximal end of handle body 1029, as shown in FIG. 11A. Coupling pin 1036 is attached to notch 1069 of sleeve 1060, and ball assembly 1024 does not engage detent 1066, but rather slidably contacts an outer surface of sleeve 1060, as depicted in FIG. 11D. The connection of cap 1040 to handle 1020 and the pin 1036 to the notch 1069 helps constrain the sleeve 1060 and first inserter 1030 from movement within and relative to handle body 1029.

Also in the first insertion configuration, second inserter 1050 is fixedly connected or secured to handle body 1029 which prevents inserter 1050 from moving relative to handle 1020. In this regard, second inserter 1050 is generally connected to the first distally facing surface 1021, which helps provide an abutment during impaction, which is illustrated in FIG. 12C.

In addition, the first insertion end 1031 of first inserter 1030 extends further from the handle body 1029 than second insertion 1051 end of second inserter 1050. This allows first inserter 1030 to deliver a first anchor into bone without obstruction by second inserter 1050. In addition, second insertion end 1051 is generally disposed within sleeve 1060 so that a terminal end 1062 of sleeve 1060 is located in a first position which is at about the same position distally as the second insertion end 1051, if not more distal than second insertion end 1051. Terminal end 1062 is also positioned more proximal than first insertion 1031 end and is located along the length of first inserter 1030 so as to act as a depth stop during insertion of a first anchor. In other words, in the first configuration of assembly 1010, terminal end 1062 of sleeve 1060 is spaced a predetermined distance from first insertion end 1031 so that when first inserter 1030 is inserted into bone up to terminal end 1062 of sleeve 1060, the insertion end 1031 is located at the desired depth in the bone. This may be particularly useful during arthroscopic surgery in which inserters 1030, 1050 and sleeve 1060 are passed through an arthroscopic cannula and the operator's vision of the same may be obscured. In this regard, abutment of bone with sleeve 1060 may provide tactile feedback to the operator indicating to the operator that the appropriate penetration depth has been achieved. Further, such positioning may also serve to protect the second anchor on second insertion end 1051 during insertion of the first anchor.

When transitioning from the first configuration to the second configuration, assembly 1010 generally goes through three different stages. In the first stage, cap 1040 is disconnected from the proximal end of handle body 1029. This allows first inserter 1030 to move proximally within and relative to handle body 1029. Also, in this stage coupling pin 1036 remains connected to sleeve 1060, which allows sleeve 1060 to move proximally in conjunction with first inserter 1030.

In the second stage, as depicted in FIGS. 12A-12C, first inserter 1030 is moved proximally relative to its position in the first configuration. In addition, the sleeve 1060, which remains connected to first inserter 1030, is also moved proximally from its first position to a second position. In the second position, the ball assembly 1024 engages detent 1066 of sleeve 1060. Thus, in the second stage of the transition phase, sleeve 1060 is connected to both the first inserter 1030 and handle body 1029, as best shown in FIG. 12C. Also, as is depicted in FIGS. 12A and 12B, the movement of sleeve 1060 into the second position exposes second insertion end 1051 of second inserter 1050. In this regard, terminal end 1062 of sleeve 1060 in the second position is located along the length of second inserter 1050 and relative to second insertion end 1051 so as to operate as a depth stop when inserting a second bone anchor via second inserter 1050. Thus, sleeve 1060 can be moved from a first position in which sleeve 1060 operates as a depth stop for first inserter 1030 to a second position in which sleeve 1060 operates a depth stop for second inserter 1050.

In the third stage of the transition phase, as depicted in FIGS. 13A and 13B, coupling pin 1036 of first inserter 1030 is disengaged from sleeve 1060 while the sleeve 1060 remains in the second position. This generally occurs when a sufficient force pulling on cap 1040 overcomes the connection between pin 1036 and notch 1069. Sleeve 1060 is prevented from being pulled out of handle body 1029 by the ball-detent engagement mechanism 1024, 1066 and also by the second distal facing surface 1023. As such, pin 1036 slides out of notch 1069 and slides out of longitudinal slot 1025 of handle body 1029, as shown. Thus, in the third stage, sleeve 1060 is releasably connected to the handle body 1029 and constrained in the second position via the engagement mechanism 1024, 1066. Also, first inserter 1030 is freed from sleeve 1060 and is unconstrained so as to be removable from handle 1020.

Figure 14:
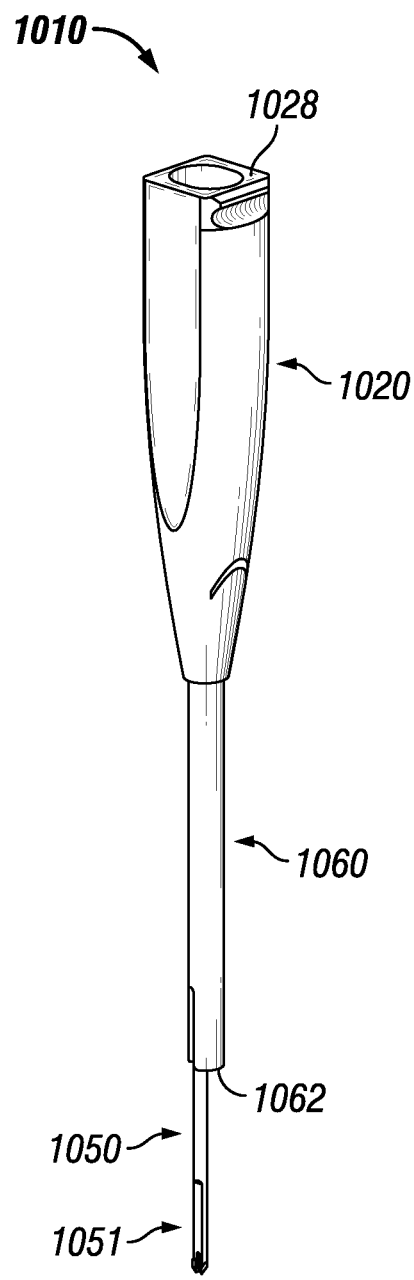
FIG. 14 is a perspective view of the inserter assembly of FIG. 11A being depicted in a second insertion configuration.

The third stage of the transition phase leads to the second insertion configuration, which is illustrated in FIG. 14. In the second insertion configuration, inserter assembly 1010 is configured to insert a second anchor into bone. In this regard, first inserter 1030 is completely removed from handle 1020. Cap 1040, which can be used to impact first inserter into bone, is also removed from handle 1020 which allows impact surface 1028 of handle 1020 to be used to impact second inserter 1050 into bone. Sleeve 1060 is connected to handle body 1029 in the second position exposing second insertion end 1051 and whatever anchor is mounted thereto. Terminal end 1062 of the sleeve 1060 is positioned relative to second insertion end 1051 so as to operate as a depth stop.

In a method of use, inserter assembly 1010 is utilized to repair soft tissue, such as a rotator cuff, glenoid labrum, acetabular labrum, meniscus, soft tissue in smaller joints such as in the hand, foot, ankle, or wrist, and the like. In an exemplary method, as is now described, the inserter assembly is utilized to repair a torn rotator cuff. Inserter assembly 1010 may be provided to an operator preloaded with bone anchors, such as filamentary anchor 12. In this regard, inserter assembly may be provided in the first insertion configuration (see FIGS. 11A-11D) with a first anchor mounted on the first insertion end 1031 and a second anchor mounted on the second insertion end 1051. These anchors may be bent over respective crotches of the insertion ends 1031, 1051 so that respective ends of the anchors face a proximal direction toward handle 1020. One or more lengths of filament, such as filament 20, extend through both anchors while the anchors are mounted to their respective inserters 1030, 1050 (see, for example, assembly 610 of FIG. 6B). The one or more filaments may engage the cleats 1022 in order to retain the anchors and filament in the desired configuration.

With assembly 1010 in the first configuration and loaded with two anchors, the operator places the first insertion end 1031 of first inserter 1030 adjacent the tissue to be repaired. This may be performed through an arthroscopic cannula or via open surgery. Once the penetration location is identified, the operator impacts cap 1040 which pierces the soft tissue and penetrates bone. The operator continues to impact cap 1040 until terminal end 1062 of sleeve 1060 abuts the bone/tissue indicating that the appropriate penetration depth has been achieved. The operator may then seat the first anchor within the bone hole formed by first insertion end 1031 by pulling the assembly 1010 proximally and tensioning the filament.

Thereafter, the assembly is transitioned to the second insertion configuration. This may be achieved while the assembly extends through the arthroscopic cannula and placed adjacent the repair site. It should be noted that as this transition occurs, the first anchor, which is secured to the bone, is also connected to the second anchor, which is connected to the second inserter 1050, via the one or more filaments. As described above, assembly 1010 goes through several stages of a transition phase to transition from the first insertion configuration to the second insertion configuration. In this regard, the operator detaches cap 1040 from handle body 1029 and moves first inserter 1030 proximally through handle body 1029. As this occurs, sleeve 1060 also moves proximally which unsheathes second insertion end 1051 and the second anchor mounted thereto.

The operator continues to move first inserter 1030 through handle body 1029 until sleeve abuts distally facing surface 1023 and ball assembly 1024 engages detent 1066 of sleeve 1060, which secures sleeve to handle 1020 (see FIGS. 12A-12C). The operator may then apply sufficient force to first inserter 1030 to disconnect pin 1036 from notch 1069 in a proximal direction (see FIGS. 13A-13B). First inserter 1030 is then removed from the proximal end of assembly 1010. Once first inserter 1030 is completely removed, assembly 1010 is in the second insertion configuration (see FIG. 14). The operator then places second insertion end 1051 adjacent the tissue to be repaired in a location offset from the first anchor. Impact surface 1028 is then impacted so as to penetrate the tissue and underlying bone with second inserter 1050. Impact surface 1028 is impacted until terminal end 1062 of sleeve 1060 abuts the tissue and bone, which may be felt by the operator. The operator then seats the second anchor within the hole formed by second insertion end 1051 by pulling assembly 1010 proximally and tensioning the filament. Thereafter, assembly 1010 may be removed from the patient and the filament may be unsecured from the cleats 1022 for further use. The end result may be similar to the implanted configuration shown in FIGS. 6C and 6D with the difference being that there would be two implanted anchors, rather than the three depicted.

Although assembly 1010 has been described as being particularly suitable for implantation of soft, filamentary anchors, it should be understood that assembly could also operate to implant hard anchors where inserters 1030, 1050 are configured to retain hard anchors. The general operation, including the transition from the first insertion configuration to the second configuration, would remain the same.

In addition, assembly 1010 may be utilized in conjunction with standard filament or filament that has round and flat portions, such as filament 320, for example. In this regard, assembly 1010 may be preloaded with a first and second anchor and a filament that extends through both anchors. Such filament may have a flat portion, such as tape portion 323, disposed between the two anchors so that when the anchors are implanted, the flat portion spans the implanted anchors helping to compress the damaged tissue to bone.

Figure 15C:
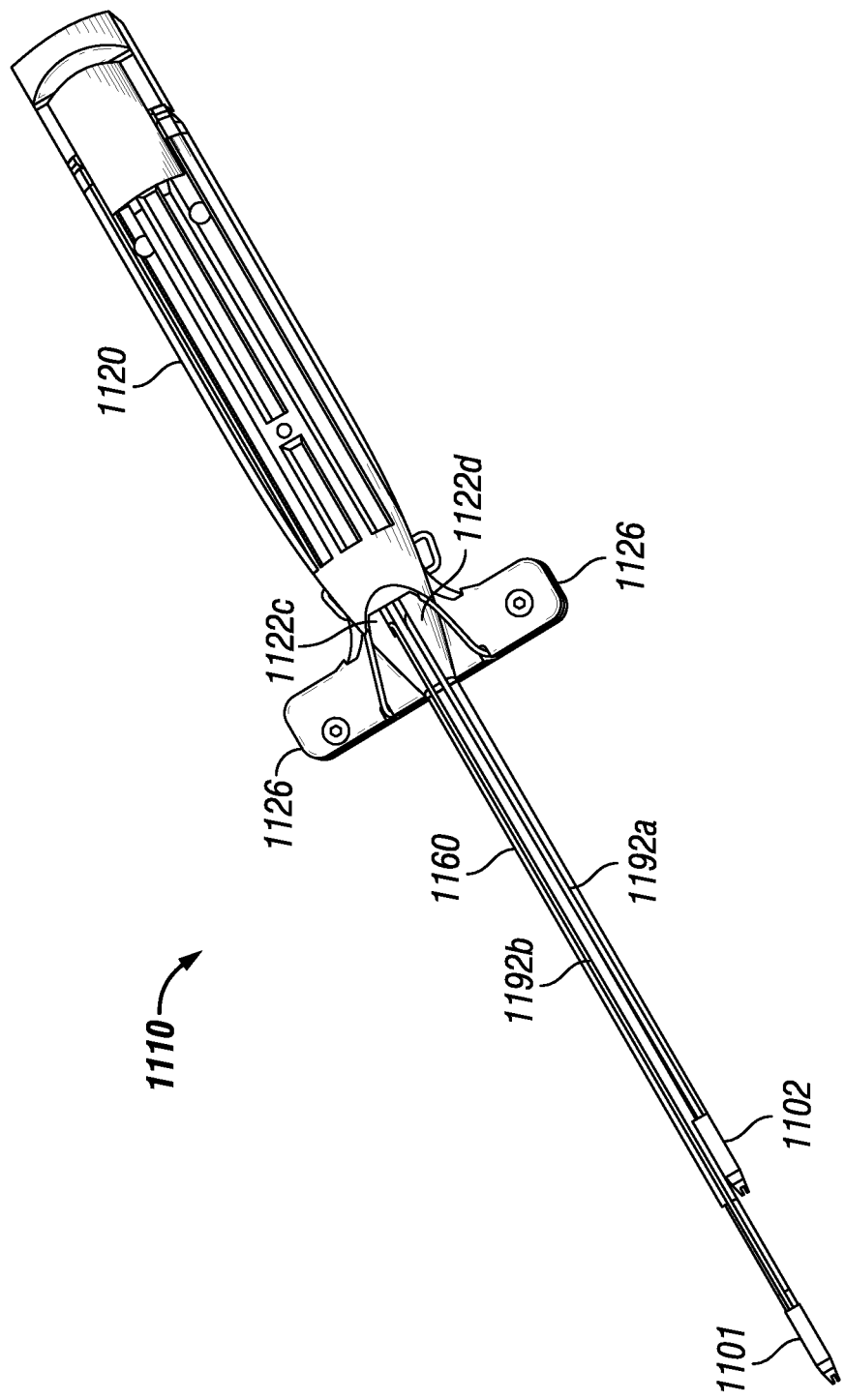
FIG. 15C is rear perspective view of the inserter assembly of FIG. 15A.

FIGS. 15A-15C depict an inserter assembly 1110 according to an even further embodiment of the present disclosure. Assembly 1110 is similar to assembly 1010 in that it includes a first inserter 1130, second inserter 1150, handle 1120, sleeve 1160, and cap 1140. Also, similar to assembly 1010, first inserter 1130 is connected to cap 1140 and is removable from handle 1120, and second inserter 1150 is fixedly connected to handle 1120. However, assembly 1110 differs from assembly 1010 with regard to handle 1120 and its filament management features.

Handle 1120 includes wings 1126 that extend outwardly from a distal end thereof. Such wings 1126 include tapered notches 1128 that are configured to retain a filament. In addition, a front side of handle 1120 includes two channels 1121a-b extending into an outer surface thereof and also extending in a proximal-distal direction from a distal end of the handle (best shown in FIGS. 15A and 15B). These channels 1121a-b diverge and turn along a circular route so that they intersect themselves. This forms a first and second cleat or full-circle cleats 1122a-b for retaining a portion of a filament.

A rear side of handle 1120 also includes channels 1122c-d that extend into an outer surface thereof and extend in a proximal-distal direction from a distal end of the handle 1120. These channels 1122c-d also diverge but do not circle back to intersect themselves. This forms a third and fourth cleat or cantilevered cleats 1122c-d for retaining a portion of a filament.

FIGS. 15A-15C also depict a filament and anchor assembly in one embodiment configuration as mounted to assembly 1110. As shown, a first anchor 1101 is mounted to first inserter 1130, and a second anchor 1102 is mounted to second inserter 1150. A single length of filament 1190 extends through both anchors 1101, 1102. However, it should be understood that multiple filaments can extend through such anchors in a similar fashion, and is generally preferable. However, one filament is depicted as a visualization aid.

Referring to FIG. 15C, free ends 1192a-b of filament 1190 extend along a rear side of sleeve 1160 and external thereto in a proximal direction. Free ends 1192a-b extend through channels 1122c-d and turn laterally so as to be hooked by cleats 1122c-d. Free ends 1192a-b extend toward respective wings 1126 and engage notches 1128 so that they are retained therein (best shown in FIG. 15B).

At the front side of assembly 1110, a loop end 1196 of filament extends along sleeve 1160 and external thereto in a proximal direction away from anchors 1101 and 1102. Loop end 1196 is the portion of filament 1190 that extends between anchors 1101 and 1102. Adjacent segments 1191a-b of loop end 1196 extend through channels 1121a-b and wrap around cleats 1122a-b. The very end of loop end 1196 projects from handle 1120. This allows an operator to tug loop end 1196 distally to release loop end 1196 from cleats. In this regard, handle 1120 provides quick and easy release of filament.

Figures 16A, 16B:
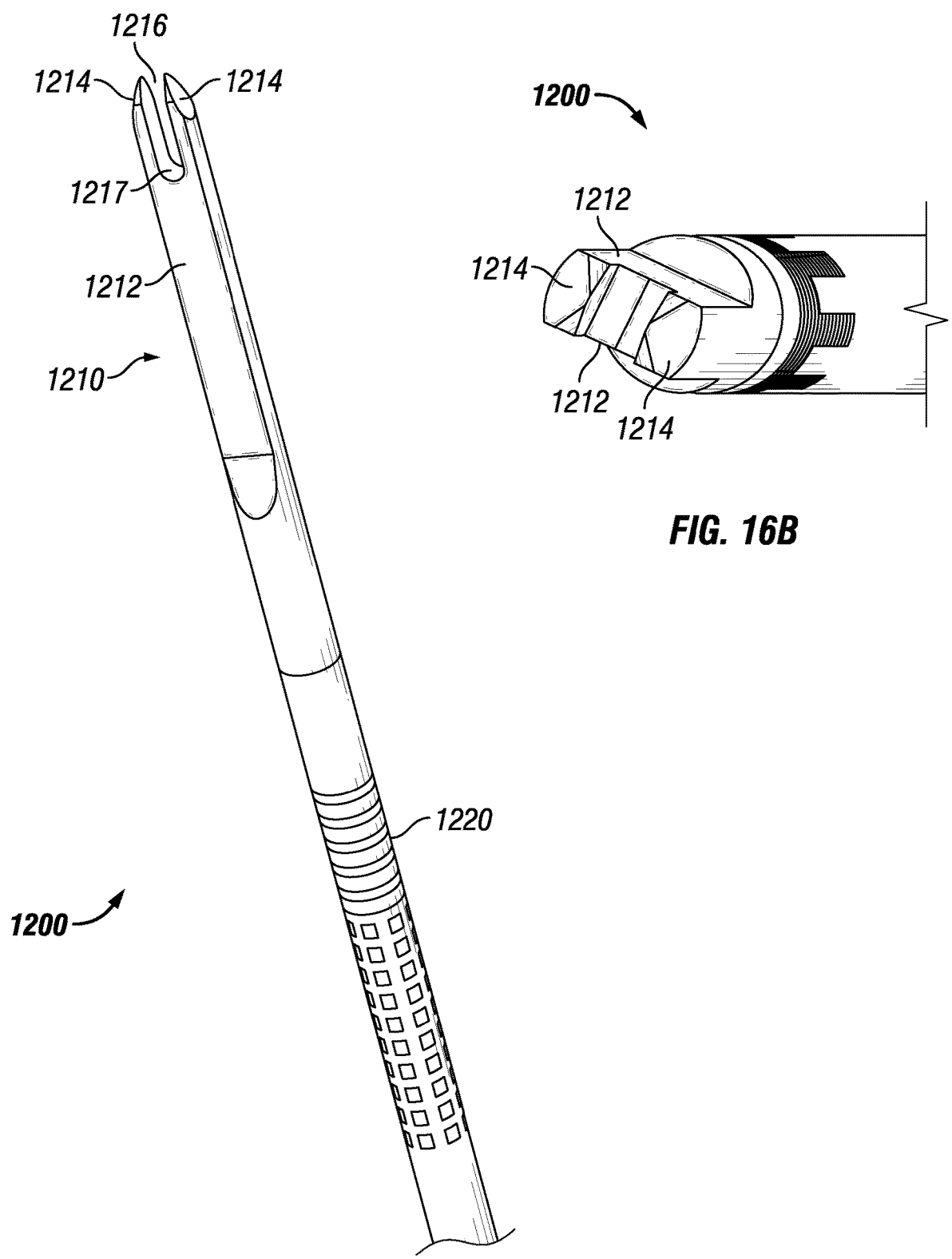
FIG. 16A is a front perspective view of an inserter according to another embodiment of the present disclosure.
FIG. 16B is a top perspective view of the inserter of FIG. 16A.

FIGS. 16A and 16B depict an inserter 1200 according to another embodiment of the present disclosure. Inserter 1200 can be utilized in assembly 1010 as both first and second inserters 1030 and 1050. Inserter 1200 can also be utilized with assembly 1110 and in the other inserter assemblies described further below. Inserter 1200 is defined by an elongate shaft which has indicia 1220, such as laser etched indicia, located along its length to help indicate penetration depth of inserter 1200. An insertion end 1210 is located at a distal end of the elongate shaft. Insertion end 1210 includes prongs or penetrating tips 1214 that are separated by a recess 1216. Penetrating tips 1214 are sufficiently sharp to penetrate or pierce soft tissue. Penetrating tips 1214 may also be sufficiently sharp and sufficiently rigid to penetrate cortical and/or cancellous bone. As shown, tips 1214 taper in at least two planes and, as such, are defined by one or more tapered surfaces.

Recess 1216 defines a crotch 1217 and is dimensioned to receive and retain a bone anchor, such as filamentary sleeve anchor 12. More particularly, recess 1216 is dimensioned such the anchor can be placed in recess 1216 and bent over crotch 1217 so that the anchor sits proximal relative to penetrating tips 1214.

Insertion end 1210 also has two indented surfaces 1212 disposed on opposite sides thereof. Such indented surfaces 1212, as shown, are planar surfaces that extend distally toward the terminal, distal end of inserter 1200. In this regard, indented surfaces 1212 intersect recess 1216 and the tapered surfaces of tapered tips 1214. This is in contrast to inserter end 1031, as shown in FIGS. 11B and 11C, in which indented surfaces 1033 terminate at radially extending projections prior to reaching tips 1032. Indented surfaces 1212 help reduce the profile of insertion end 1210 so that a relatively small hole may be utilized for implantation of a bone anchor.

Figure 17A:
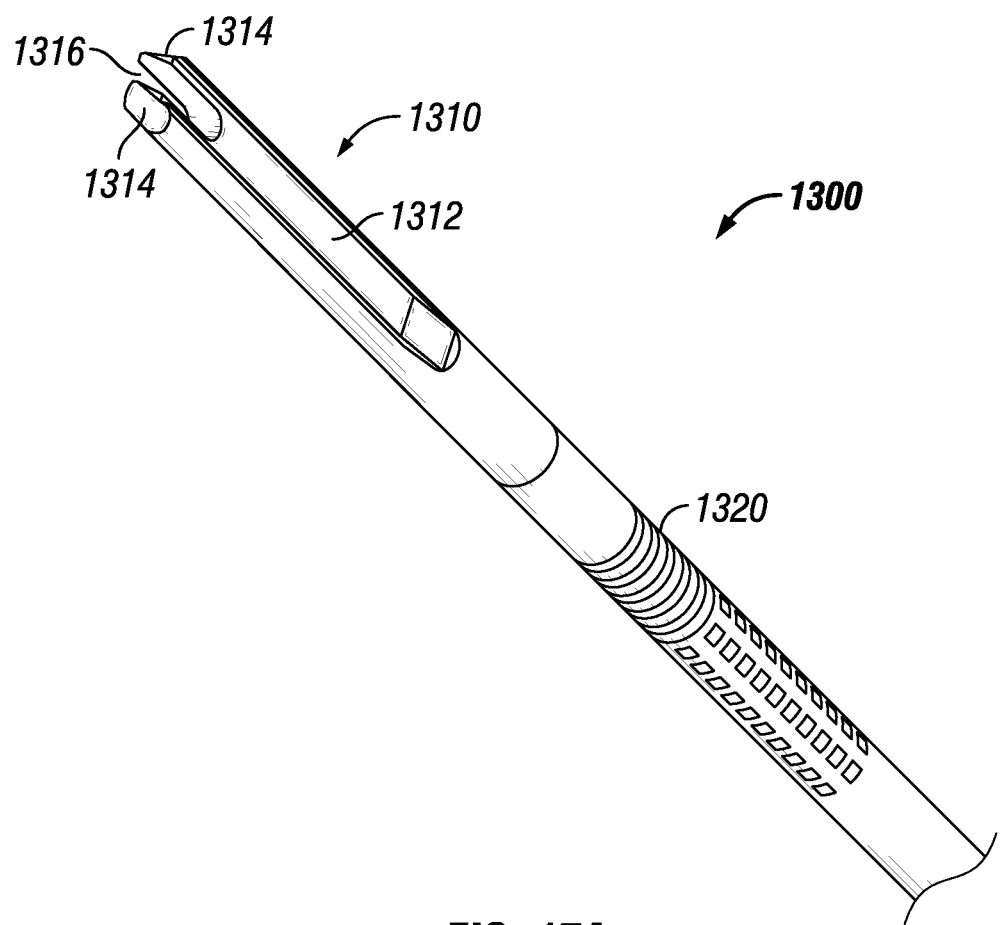
FIG. 17A is a front perspective view of an inserter according to yet another embodiment of the present disclosure.
Figure 17B:
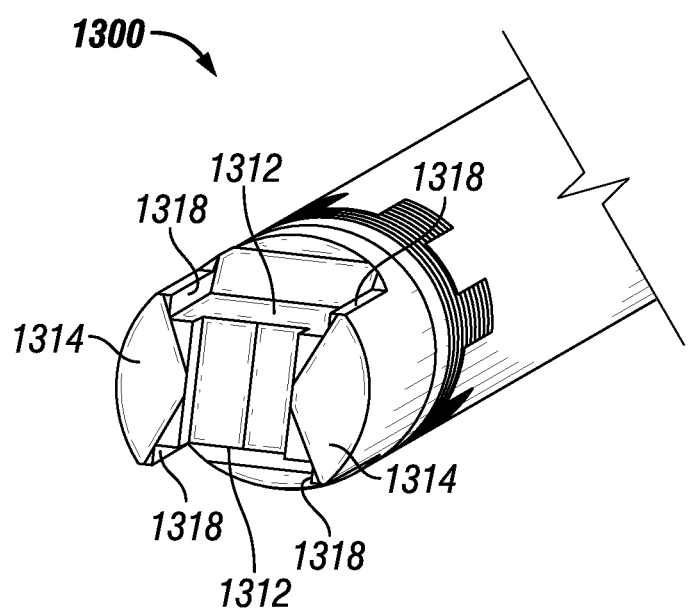
FIG. 17B is a top perspective view of the inserter of FIG. 17A.

FIGS. 17A and 17B depict an inserter 1300 according to an addition embodiment of the disclosure. Inserter 1300 is similar to inserter 1200 in that it is defined by an elongate shaft and includes an insertion end 1320 having indented surfaces 1312 and penetrating tips 1314 separated by a recess 1316. However, inserter 1300 differs from inserter 1200, in that insertion end 1320 has an I-beam configuration. In this regard, flanges 1318 flank indented surfaces 1312 and extend radially outwardly therefrom. This forms a recessed space between flanges 1318 which can receive a portion of a filamentary anchor, such as anchor 12. In this regard, flanges 1318 help provide stiffness to penetrating tips 1314 for penetration into bone, while also providing a reduced profile for inserting an anchor into a relatively small bone hole.

FIG. 18 depicts an inserter assembly 1410 in a first insertion configuration according to a further embodiment of the present disclosure. Assembly 1410 is similar to assembly 1010 in that it includes a handle 1420, a first inserter 1430, a second inserter 1450, and a cap 1440. In addition, as with assembly 1010, first inserter 1430 is attached to cap 1440 and is removable from handle body 1429, and second inserter 1450 is fixedly connected to handle body 1429 so that second inserter 1450 is immovable relative to handle body 1429. However, unlike assembly 1010, assembly 1410 does not include a sleeve, such as sleeve 1060, and handle 1420 includes wings 1426. Wings 1426 are similar to wings 1126 in that they have notches 1428 to assist in filament management.

Although assembly 1410 does not have a sleeve to act as a depth stop as described above in relation to assembly 1010, inserters 1430 and 1450 each include indicia 1432, 1452, respectively, along their length that indicate depth level, which can be observed arthroscopically relative to a bone or tissue surface. In this regard, in a method of operation, first inserter 1430 with a first anchor mounted thereto is impacted through soft tissue into bone until a surface of the bone or tissue aligns with the indicia 1432. The first anchor is then seated into an opening formed by first inserter 1430 via tensioning of a filament coupled to the first anchor after the anchor is implanted into the opening and first inserter 1430 is removed from the opening. Thereafter, cap 1440 is disengaged from a proximal end of handle body 1429, and first inserter 1430 is advanced proximally out of handle body 1429. After first inserter 1430 is removed from handle body 1429, assembly 1410 is in a second insertion configuration (not shown) for inserting a second anchor mounted to second inserter 1450. Second inserter 1450 is then impacted through soft tissue into bone at a location offset from the implanted first anchor until indicia 1452 disposed on second inserter 1450 align with a surface of bone or tissue. The second anchor is then seated within the opening formed by second inserter 1450.

FIG. 19 depicts an inserter assembly 1510 according to an additional embodiment of the present disclosure. Assembly 1510 is similar to assembly 1010 in that it includes a handle 1520, first inserter 1530, second inserter 1550, cap 1540, and sleeve 1560. However, assembly 1510 differs with regard to its sleeve engagement mechanism 1524, which, as depicted, is a constant force spring. As previously described, assembly 1010 utilizes ball assembly 1024 located in handle 1020 to connect handle 1020 to sleeve 1060. First inserter 1030, which connects to sleeve 1060 via pin 1036 and slot 1069, allows sleeve 1060 to be moved from a first position to a second position where the ball-detent mechanism 1024, 1066 is actuated to connect handle 1020 to sleeve 1060.

In contrast, constant force spring 1524 is disposed within a recess 1523 in handle 1520 and includes a free end 1525 that is connected to a proximal end of sleeve 1560. Constant force spring 1524 applies a constant force on sleeve 1560 in the proximal direction. In a first position, sleeve 1560 is at its distal most extent relative to inserters 1530 and 1550. In this position, a pin 1536 extending from first inserter 1530 abuts the proximal end of sleeve 1560 which pushes sleeve 1560 against the bias of spring 1524. Additionally, cap 1540 can be secured to the proximal end of handle body 1520. When cap 1540 is secured, first inserter 1530 via pin 1536 holds sleeve in the first position in which sleeve 1560 acts as a depth stop for first inserter 1530.

In a second position, cap 1540 is disengaged from handle body 1520 and first inserter 1530 is removed from handle 1520 which also removes the counterforce to spring 1524. As such, sleeve 1560 is able to automatically retract into handle body 1520 in the proximal direction and into a second position in which sleeve 1560 acts as a depth stop for second inserter 1550. A distally facing surface 1523 within handle body 1529 prevents sleeve 1560 from retracting any further beyond the second position.

A method of operation of assembly 1510 is similar to that of assembly 1010. In this regard, first inserter 1530 is impacted into bone until the bone or tissue contacts sleeve 1560 so as to implant a first anchor. First inserter 1530 is removed from handle 1520, and sleeve 1560 automatically retracts into its second position where it abuts distally facing surface 1523. Second inserter 1550 is then impacted into bone until the bone or tissue contacts sleeve 1560 so as to implant a second anchor into the bone.

Figure 20A:
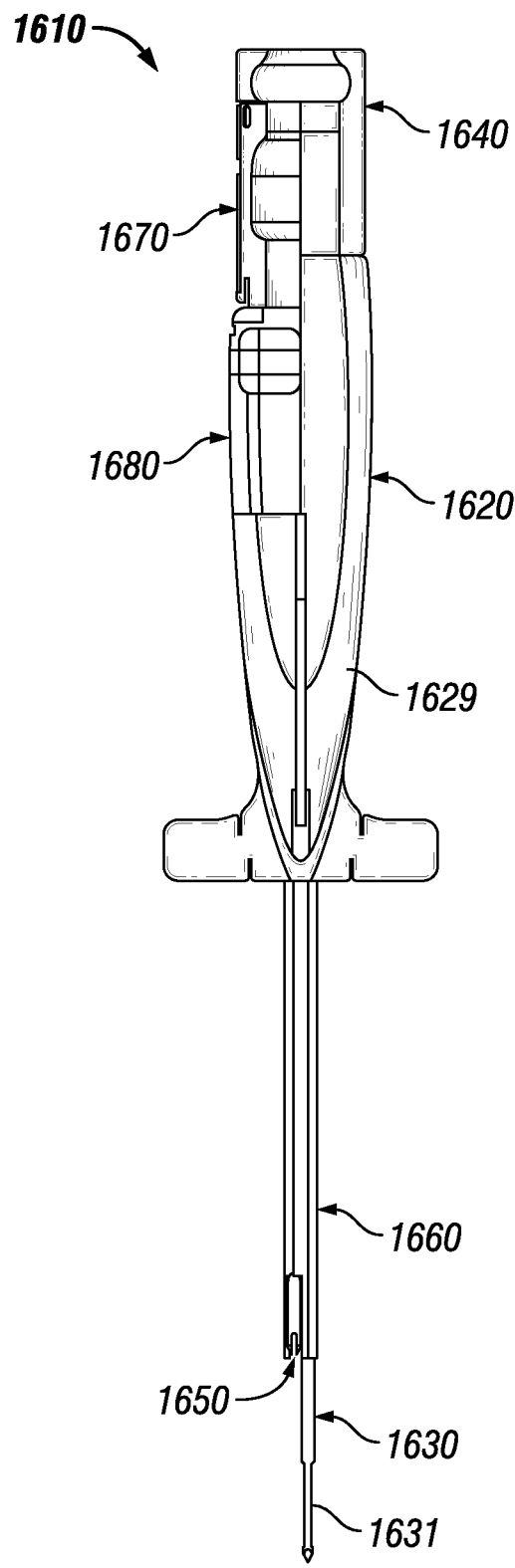
FIG. 20A is a front view of an inserter assembly according to yet another embodiment of the present disclosure being depicted in a first insertion configuration.
Figure 20B:
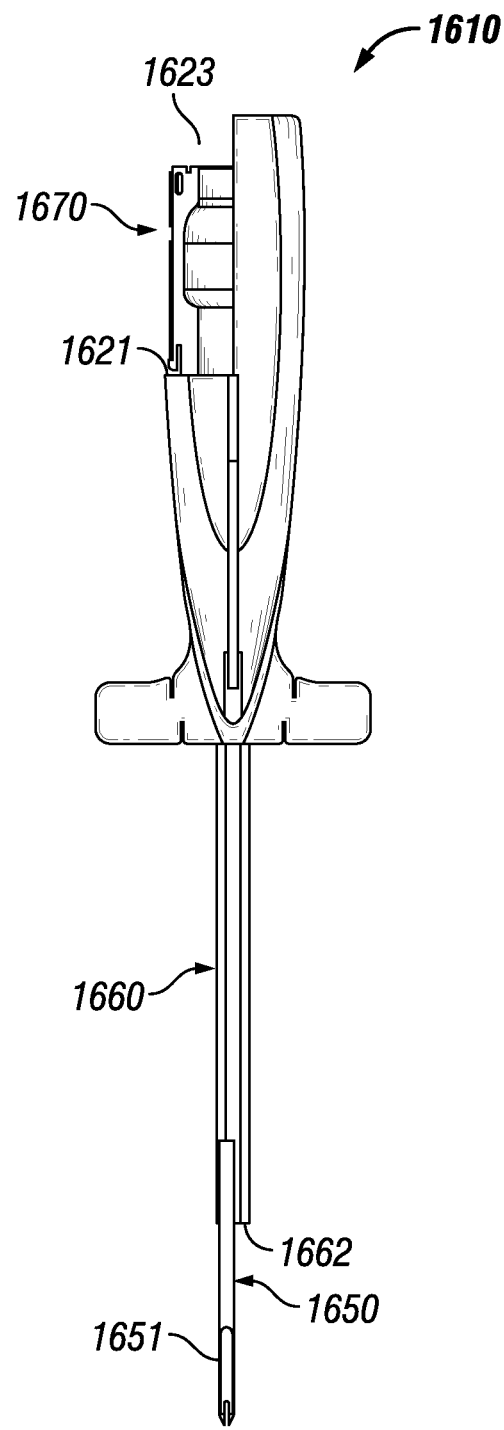
FIG. 20B is a front view of the inserter assembly of FIG. 20A being depicted in a second insertion configuration.

FIGS. 20A and 20B depict an inserter assembly 1610 according to yet another embodiment of the present disclosure. Assembly 1610 includes a handle 1620, a first inserter 1630, a second inserter 1650, a first cap 1640, a second cap 1670, a sleeve 1660, and a pull tab 1680. First inserter 1630 is connected to first cap 1640 at its proximal end. Second inserter 1650 is connected to second cap 1670 at its proximal end. Similar to assembly 1010, first inserter 1630 is longer than second inserter 1650, and first inserter 1630 is removable from handle body 1629. However, unlike assembly 1010, second inserter 1650 is moveable relative to handle body 1629 and may also be removable therefrom. Also, unlike assembly 1010, sleeve 1660 is fixedly connected to an interior of handle body 1629.

Handle 1620 is comprised of a handle body 1629 and a pull tab 1680 that can be removed from a side of handle 1620. Tab 1680 may connect to handle 1620 via a rail (not shown) that extends from a distal end of tab 1680 which engages a slot (not shown) in handle 1620, for example, so that tab 1680 can be pulled laterally away from handle 1620. Pull tab 1680 forms part of a passageway that receives second inserter 1650. First cap 1640 has an L-shape so as to make space for second cap 1670, as shown in FIG. 20A.

FIG. 20A depicts assembly 1610 in a first insertion configuration. In the first insertion configuration, first and second inserters 1630, 1650 extend through handle 1620 and sleeve 1660 so that first inserter 1630 extends more distally than second inserter 1650. A terminal end 1662 of sleeve 1660 is positioned relative to a first insertion end 1631 of first inserter 1630 a predetermined distance so that sleeve 1660 can act as a depth stop for first inserter 1630. Also, a second insertion end 1651 of second inserter 1650 is disposed within a passageway of sleeve 1660. Pull tab 1680 is connected to handle 1620 and second cap 1670 of second inserter 1650 is stacked onto pull tab 1680 at a proximal location relative thereto. First cap 1640 is connected to handle 1620 at a proximal end thereof and also stacked onto second cap 1670.

FIG. 20B depicts assembly 1610 in a second insertion configuration. In the second insertion configuration, first inserter 1630 is removed which exposes a proximal end of second cap 1670. In addition, pull tab 1680 is removed from handle 1620 which allows second cap 1670 to move proximally into a recess 1623. Although a proximal surface of cap 1670 is depicted as being distal to a proximal surface of handle body 1629, it should be understood that such surfaces can be flush in some embodiments. Positioning of second cap 1670 in recess 1623 also positions second insertion end 1651 of second inserter 1650 more distally than when assembly 1610 is in the first insertion configuration. In this regard, second insertion end 1651 is unsheathed from sleeve 1660. Also, terminal end 1662 of sleeve 1660 is positioned a predetermined distance from second insertion end 1651 so as to act as a depth stop for second inserter 1650.

In a method of operation of assembly 1610, an operator impacts first inserter 1630 through tissue into underlying bone to implant an anchor mounted thereto. Once the first anchor is implanted, first cap 1640 is disconnected from handle 1620 and first inserter 1630 is removed from handle body 1629. Tab 1680 is also removed by pulling tab 1680 laterally away from handle 1620. Second cap 1670 is slid into handle recess 1623 which exposes second insertion end 1651 and an anchor mounted thereto. Second cap 1670 is connected to handle 1620 so as to hold second inserter 1650 in place during insertion. Operator then impacts second inserter 1650 through tissue and into bone offset from the first anchor. Impaction may be performed on a proximal surface of second cap 1670 and/or on a proximal end of handle body 1629. Once the second anchor is implanted, assembly 1610 can be removed from the patient.

Although the invention herein has been described with reference to particular embodiments, it is to be understood that these embodiments are merely illustrative of the principles and applications of the present invention. It is therefore to be understood that numerous modifications may be made and are encouraged to be made to the illustrative embodiments and that other arrangements may be devised without departing from the spirit and scope of the present invention as defined by the appended claims.

The invention claimed is:

1. An inserter assembly for inserting anchors into bone, comprising:
a handle having a handle body;
a sleeve partially disposed within the handle body and having a passageway extending through the sleeve in a proximal-distal direction;
a first inserter partially disposed within the handle body and passageway of the sleeve, the first inserter being configured to retain a first anchor for insertion thereof into bone; and
a second inserter partially disposed within the handle body and passageway of the sleeve, the first inserter being configured to retain a second anchor for insertion thereof into bone,
wherein the inserter assembly has a first configuration in which the sleeve is connected to the first inserter so that the first inserter and sleeve are moveable together relative to the handle body, and a second configuration in which the sleeve is connected to the handle body and disconnected from the first inserter so that the first inserter is moveable relative to the sleeve.

2. The assembly of claim 1, wherein the handle includes a first engagement feature adjacent a passageway that is defined by the handle body, and the sleeve includes a second engagement feature and is disposed within the passageway of the handle body, the first and second engagement features being configured to interface so as to hold the sleeve in releasable connection with the handle body while in the second configuration.

3. The assembly of claim 2, wherein the first and second engagement features comprise a ball detent mechanism.

4. The assembly of claim 1, wherein the sleeve includes a notch extending into a proximal end thereof, and the first inserter includes a pin extending outwardly therefrom, the notch and pin being correspondingly sized so as to provide an interference fit therebetween for releasably connecting the sleeve to the first inserter.

5. The assembly of claim 1, wherein the first inserter is removable from the handle body and the second inserter is fixedly secured to the handle body.

6. The assembly of claim 5, wherein in the first configuration, the first inserter extends further from the handle body in a proximal-distal direction than the second inserter.

7. The assembly of claim 1, wherein the first inserter includes a cap releasably connectable to a proximal end of the handle body.

8. The assembly of claim 1, wherein the sleeve operates as a depth stop for both the first and second inserters when in the first and second configurations, respectively.

9. The inserter of claim 1, wherein the first and second inserters each include an insertion end configured to penetrate at least one of soft tissue and bone.

10. An inserter assembly for inserting anchors into bone, comprising:
a handle having a handle body;
a first inserter disposed within the handle body and being fixedly connected thereto, the first inserter having an insertion end configured to retain a first anchor for insertion thereof into bone; and
a second inserter slidably disposed within the handle body and having an insertion end configured to retain a second anchor for insertion thereof into bone.

11. The assembly of claim 10, further comprising a sleeve slidably disposed within the handle body and releasably connected to the second inserter.

12. The assembly of claim 11, wherein the sleeve extends from a distal end of the handle body and has a terminal end that is disposed more proximal than the insertion end of the first inserter and more distal than the insertion end of the second inserter when the assembly is in a first configuration, and is disposed more proximal than the insertion end of the second inserter when the assembly is in a second configuration.

13. The assembly of claim 11, wherein the first inserter is removable from the handle body.

14. The assembly of claim 11, wherein the sleeve is releasably connectable to the handle body.

15. The assembly of claim 14, wherein the sleeve is releasably connected to the first inserter via a pin extending from the first inserter into a notch at a proximal end of the sleeve.

16. An inserter assembly for soft tissue repair, comprising:
an inserter handle having a handle body;
a first inserter slidably disposed within the handle body and having an insertion end extending distally from the handle body;
a first anchor defining a passageway extending therethrough and being mounted to the insertion end of the first inserter for insertion thereof into bone;
a second inserter fixedly connected to the handle body and having an insertion end extending distally from the handle body;
a second anchor defining a passageway extending therethrough and being mounted to the insertion end of the second inserter for insertion thereof into bone; and
a sleeve slidably disposed within the handle body and positioned about respective portions of the first and second inserters, the sleeve being moveable relative to the second inserter between a first and second position.

17. The assembly of claim 16, wherein the first and second anchors are filamentary sleeves.

18. The assembly of claim 16, wherein in the first position, a terminal end of the sleeve is located further from the handle body in a proximal-distal direction than the insertion end of the second inserter, and in the second position the terminal end of the sleeve is located closer to the handle body in the proximal-distal direction than the insertion end of the second inserter.

19. The assembly of claim 18, wherein:
in the first position, the terminal end of the sleeve is positioned closer to the handle body in the proximal-distal direction than the insertion end of the first inserter and is positioned along the length of the first inserter relative to the insertion end of the first inserter so as to operate as a depth stop upon insertion of the first anchor into bone, and
in the second position, the terminal end of the sleeve is positioned along the length of the second inserter relative to the insertion end of the second inserter so as to operate a depth stop upon insertion of the second anchor into bone.

20. The assembly of claim 19, wherein:
the first inserter further includes a cap connected to a proximal end thereof and is releasably connectable to a proximal end of the handle body,
the handle includes a retaining member disposed within the handle body and adjacent to the sleeve,
the sleeve includes a recess disposed along its length and configured to engage the retaining member so as to releasably connect the sleeve to the handle,
when the cap is connected to the handle body, the sleeve is in the first position, and
when the cap retaining member engages the recess of the sleeve, the sleeve is in the second position.

\* \* \* \* \*